US009187534B2

(12) United States Patent
Derouazi et al.

(10) Patent No.: US 9,187,534 B2
(45) Date of Patent: Nov. 17, 2015

(54) MULTI-EPITOPIC VACCINE

(75) Inventors: Madiha Sabiha Derouazi, Grand-Saconnex (CH); Paul R. Walker, Viry (FR); Pierre-Yves Dietrich, St Julien en Genevois (FR)

(73) Assignees: UNIVERSITE DE GENEVE, Geneva 4 (CH); HOPITAUX UNIVERSITAIRES DE GENEVE, Geneva 14 (CH)

( * ) Notice: Subject to any disclaimer, the term of this patent is extended or adjusted under 35 U.S.C. 154(b) by 71 days.

(21) Appl. No.: 13/415,877

(22) Filed: Mar. 9, 2012

(65) Prior Publication Data

US 2012/0231030 A1 Sep. 13, 2012

Related U.S. Application Data

(60) Provisional application No. 61/451,615, filed on Mar. 11, 2011.

(51) Int. Cl.
| | |
|---|---|
| C07K 14/005 | (2006.01) |
| A61K 39/12 | (2006.01) |
| C07K 14/77 | (2006.01) |
| C07K 14/47 | (2006.01) |
| C12N 9/86 | (2006.01) |
| A61K 39/00 | (2006.01) |

(52) U.S. Cl.
CPC ........... *C07K 14/005* (2013.01); *A61K 39/0005* (2013.01); *A61K 39/0011* (2013.01); *A61K 39/12* (2013.01); *C07K 14/4748* (2013.01); *C07K 14/77* (2013.01); *C12N 9/86* (2013.01); *A61K 39/00* (2013.01); *A61K 2039/5158* (2013.01); *A61K 2039/6075* (2013.01); *A61K 2039/70* (2013.01); *C07K 2319/00* (2013.01); *C07K 2319/10* (2013.01); *C12N 2710/16222* (2013.01); *C12N 2710/16233* (2013.01); *C12N 2710/16241* (2013.01); *C12N 2760/10022* (2013.01); *C12N 2760/10034* (2013.01)

(58) Field of Classification Search
CPC .............. A61K 2039/5158; A61K 2039/6075; A61K 2039/70; A61K 2039/525; A61K 2039/5154; A61K 39/00; A61K 39/0005; A61K 39/0011; A61K 39/12; A61K 39/60; A61K 39/6075; A61K 39/005; C07K 14/05; C07K 14/005; C07K 14/77; C07K 14/4748; C07K 14/01; C07K 14/163; C07K 2319/00; C07K 2319/10; C07K 14/004

See application file for complete search history.

(56) References Cited

U.S. PATENT DOCUMENTS

| | | | |
|---|---|---|---|
| 2008/0044407 A1* | 2/2008 | Strome et al. .............. | 424/130.1 |
| 2012/0052080 A1* | 3/2012 | Okada ........................ | 424/184.1 |
| 2012/0214744 A1* | 8/2012 | Bourdoulous et al. ....... | 514/19.4 |
| 2012/0231030 A1* | 9/2012 | Derouazi et al. ............ | 424/192.1 |
| 2013/0116201 A1* | 5/2013 | Lenormand ........ | A61K 38/1709 514/21.2 |

FOREIGN PATENT DOCUMENTS

| | | | |
|---|---|---|---|
| WO | WO 01/51673 A2 | * | 7/2001 |
| WO | WO 2011/101332 A1 | * | 8/2011 |
| WO | WO 2011/135222 | | 11/2011 |
| WO | WO 2011/135222 A2 | * | 11/2011 |
| WO | WO2011/135222 A2 | * | 11/2011 |

OTHER PUBLICATIONS

NCBI Reference sequence YP_401673.1, last update Nov. 5, 2013.*
Rothe et al., J Biol Chem 2010; 285:20224-33.*
Rosenzweig et al., Blood 2001; 97:1951-59.*
McPherson et al., Immunol 2003; 110:386-96.*
Rothe & Lenormand, Curr Protoc Protein Sci 2008; 54:18.11.1-18.11.29.*
Tacken et al., J. Immunol., 2008; 180:7687-96.*
Duchardt et al., Traffic, 2007; 8:848-66.*
Lu et al., J. Immunol., 2004; 172:4575-82.*
Voskens et al., Head & Neck, 2012; 34:1734-46.*
Durantez, M. et al. "Induction of Multiepitopic and Long-Lasting Immune Responses Against Tumour Antigens by Immunization with Peptides, DNA and Recombinant Adenoviruses Expressing Minigenes" *Scandinavian Journal of Immunology*, 2008, pp. 80-89, vol. 69.
Mateo, L. et al. "An HLA-A2 Polyepitope Vaccine for Melanoma Immunotherapy" *The Journal of Immunology*, 1999, pp. 4058-4063, vol. 163.
Tine, J. A. et al. "Enhanced multiepitope-based vaccines elicit CD8+cytotoxic T cells against both immunodominant and cryptic epitopes" *Vaccine*, 2005, pp. 1085-1091, vol. 23.
Waeckerle-Men, Y. et al. "Dendritic cell-based multi-epitope immunotherapy of hormone-refractory prostate carcinoma" *Cancer Immunology Immunotherapy*, 2006, pp. 1524-1533, vol. 55.
Ishioka, G. Y. et al. "Utilization of MHC Class I Transgenic Mice for Development of Minigene DNA Vaccines Encoding Multiple HLA-Restricted CTL Epitopes" *The Journal of Immunology*, 1999, pp. 3915-3925, vol. 162.

(Continued)

*Primary Examiner* — Sheela J Huff
*Assistant Examiner* — Jessica H Roark
(74) *Attorney, Agent, or Firm* — Saliwanchik, Lloyd & Eisenschenk

(57) ABSTRACT

The present invention relates to isolated polypeptides comprising: (i) a protein transduction domain consisting of ZEBRA or a fragment thereof that retains the capacity of internalization, (ii) at least one CD4+ epitope; and (iii) at least one CD8+ epitope. It also relates to antigen presenting cells loaded with said polypeptides, and the use thereof in immunotherapy including prevention and/or treatment of cancers or infectious diseases.

14 Claims, 10 Drawing Sheets

(56) References Cited

OTHER PUBLICATIONS

Scardino, A. et al. "A Polyepitope DNA Vaccine Targeted to Her-2/ErbB-2 Elicits a Broad Range of Human and Murine CTL Effectors to Protect against Tumor Challenge" *Cancer Research*, 2007, pp. 7028-7036, vol. 67, No. 14.

Thomson, S. A. et al. "Recombinant Polyepitope Vaccines for the Delivery of Multiple CD8 Cytotoxic T Cell Epitopes" *The Journal of Immunology*, 1996, pp. 822-826, vol. 157.

Thomson, S. A. et al. "Minimal epitopes expressed in a recombinant polyepitope protein are processed and presented to $CD8^+$ cytotoxic T cells: Implications for vaccine design" *Proceedings of the National Academy of Sciences USA*, Jun. 1995, pp. 5845-5849, vol. 92.

Anton, L. et al. "MHC Class I—Associated Peptides Produced from Endogenous Gene Products with Vastly Different Efficiencies" *The Journal of Immunology*, 1997, pp. 2535-2542, vol. 158.

Van Montfoort, N. et al. "Antigen storage compartments in mature dendritic cells facilitate prolonged cytotoxic T lymphocyte cross-priming capacity" *Proceedings of the National Academy of Sciences*, Apr. 21, 2009, pp. 6730-6735, vol. 106, No. 16.

Brooks, N. A. et al. "Cell-penetrating peptides: Application in vaccine delivery" *Biochimica et Biophysica Acta*, 2010, pp. 25-34, vol. 1805.

Rothe, R. et al. "Characterization of the Cell-penetrating Properties of the Epstein-Barr Virus Zebra *trans*-Activator" *The Journal of Biological Chemistry*, Jun. 25, 2010, pp. 20224-20233, vol. 285, No. 26.

Rothe, Romy, Thesis entitled "Caractérisation de la propriété de la protéine Zebra du virus Epstein-Barr à pénétrer dans les cellules" *Universite De Grenoble*, Jun. 2, 2010, pp. 1-156.

Stubbs, A. C, et al. "Whole recombinant yeast vaccine activates dendritic cells and elicits protective cell-mediated immunity" *Nature Medicine*, May 2001, pp. 625-629, vol. 7, No. 5.

Derouazi, M. et al. "Towards an Efficient DC Vaccine by Antigenic Protein Loading Using a Novel Protein Transduction Domain" Poster at $11^{th}$ International Symposium on Dendritic Cells in Fundamental and Clinical Immunology, Universite De Geneve, 2010, p. 1.

Tünnemann, G. et al. "Cargo-dependent mode of uptake and bioavailability of TAT-containing proteins and peptides in living cells" *The FASEB Journal*, Sep. 2006, pp. 1775-1784, vol. 20.

Derouazi, M., et al., "Novel Cell-Penetrating Peptide-Based Vaccine Induces Robust CD4+ and CD8+ T Cell-Mediated Antitumor Immunity," *Cancer Research*, Jun. 26, 2015, pp. OF1-OF12.

\* cited by examiner

SEQUENCE LISTING

```
<160> NUMBER OF SEQ ID NOS: 272

<210> SEQ ID NO 1
<211> LENGTH: 978
<212> TYPE: DNA
<213> ORGANISM: artificial
<220> FEATURE:
<223> OTHER INFORMATION: ZEBRA-beta-lactamase

<400> SEQUENCE: 1
gatatacata tgcatcatca tcatcatcat catcacaagc gatacaagaa tcgggtggct      60
tccagaaaat gccgggccaa gtttaagcaa ctgctgcagc actaccgtga ggtcgctgct     120
gccaaatcat ctgaaaatga caggctgcgc ctcctgttga agcagatgtg cctcgaggac     180
ccagaaacgc tggtgaaagt aaaagatgct gaagatcagt tgggtgcacg agtgggttac     240
atcgaactgg atctcaacag cggtaagatc cttgagagtt ttcgccccga agaacgtttt     300
ccaatgatga gcacttttaa agttctgcta tgtggcgcgg tattatcccg tattgacgcc     360
gggcaagagc aactcggtcg ccgcatacac tattctcaga atgacttggt tgagtactca     420
ccagtcacag aaaagcatct tacggatggc atgacagtaa gagaattatg cagtgctgcc     480
ataaccatga gtgataacac tgcggccaac ttacttctga caacgatcgg aggaccgaag     540
gagctaaccg cttttttgca caacatgggg gatcatgtaa ctcgccttga tcgttgggaa     600
ccggagctga atgaagccat accaaacgac gagcgtgaca ccacgatgcc tgtagcaatg     660
gcaacaacgt tgcgcaaact attaactggc gaactactta ctctagcttc ccggcaacaa     720
ttaatagact ggatggaggc ggataaagtt gcaggaccac ttctgcgctc ggcccttccg     780
gctggctggt ttattgctga taaatctgga gccggtgagc gtgggtctcg cggtatcatt     840
gcagcactgg ggccagatgg taagccctcc cgtatcgtag ttatctacac gacggggagt     900
caggcaacta tggatgaacg aaatagacag atcgctgaga taggtgcctc actgattaag     960
cattggtaag gatcctaa                                                   978

<210> SEQ ID NO 2
<211> LENGTH: 322
<212> TYPE: PRT
<213> ORGANISM: artificial
<220> FEATURE:
<223> OTHER INFORMATION: ZEBRA-beta-lactamase

<400> SEQUENCE: 2

Asp Ile His Met His His His His His His His Lys Arg Tyr Lys
1               5                   10                  15

Asn Arg Val Ala Ser Arg Lys Cys Arg Ala Lys Phe Lys Gln Leu Leu
            20                  25                  30
```

```
Gln His Tyr Arg Glu Val Ala Ala Lys Ser Ser Glu Asn Asp Arg
     35                  40                  45
Leu Arg Leu Leu Leu Lys Gln Met Cys Leu Glu Asp Pro Glu Thr Leu
 50                  55                  60
Val Lys Val Lys Asp Ala Glu Asp Gln Leu Gly Ala Arg Val Gly Tyr
 65                  70                  75                  80
Ile Glu Leu Asp Leu Asn Ser Gly Lys Ile Leu Glu Ser Phe Arg Pro
                 85                  90                  95
Glu Glu Arg Phe Pro Met Met Ser Thr Phe Lys Val Leu Leu Cys Gly
                100                 105                 110
Ala Val Leu Ser Arg Ile Asp Ala Gly Gln Glu Gln Leu Gly Arg Arg
            115                 120                 125
Ile His Tyr Ser Gln Asn Asp Leu Val Glu Tyr Ser Pro Val Thr Glu
        130                 135                 140
Lys His Leu Thr Asp Gly Met Thr Val Arg Glu Leu Cys Ser Ala Ala
145                 150                 155                 160
Ile Thr Met Ser Asp Asn Thr Ala Ala Asn Leu Leu Leu Thr Thr Ile
                165                 170                 175
Gly Gly Pro Lys Glu Leu Thr Ala Phe Leu His Asn Met Gly Asp His
            180                 185                 190
Val Thr Arg Leu Asp Arg Trp Glu Pro Glu Leu Asn Glu Ala Ile Pro
        195                 200                 205
Asn Asp Glu Arg Asp Thr Thr Met Pro Val Ala Met Ala Thr Thr Leu
    210                 215                 220
Arg Lys Leu Leu Thr Gly Glu Leu Leu Thr Leu Ala Ser Arg Gln Gln
225                 230                 235                 240
Leu Ile Asp Trp Met Glu Ala Asp Lys Val Ala Gly Pro Leu Leu Arg
                245                 250                 255
Ser Ala Leu Pro Ala Gly Trp Phe Ile Ala Asp Lys Ser Gly Ala Gly
            260                 265                 270
Glu Arg Gly Ser Arg Gly Ile Ile Ala Ala Leu Gly Pro Asp Gly Lys
        275                 280                 285
Pro Ser Arg Ile Val Val Ile Tyr Thr Thr Gly Ser Gln Ala Thr Met
    290                 295                 300
Asp Glu Arg Asn Arg Gln Ile Ala Glu Ile Gly Ala Ser Leu Ile Lys
305                 310                 315                 320
His Trp

<210> SEQ ID NO 3
<211> LENGTH: 576
<212> TYPE: DNA
<213> ORGANISM: artificial
<220> FEATURE:
<223> OTHER INFORMATION: ZEBRA-OVA

<400> SEQUENCE: 3
gatatacata tgcatcatca tcatcatcat catcacaagc gatacaagaa tcgggtggct      60
tccagaaaat gccgggccaa gtttaagcaa ctgctgcagc actaccgtga ggtcgctgct     120
gccaaatcat ctgaaaatga caggctgcgc ctcctgttga agcagatgtg cctcgaggat     180
gaagtctcag gccttgagca gcttgagagt ataatcaact ttgaaaaact gactgaatgg     240
accagttcta atgttatgga agagaggaag atcaaagtgt acttacctcg catgaagatg     300
gaggaaaaat acaacctcac atctgtctta atggctatgg cattactga  cgtgtttagc     360
```

```
tcttcagcca atctgtctgg catctcctca gcagagagcc tgaagatatc tcaagctgtc    420
catgcagcac atgcagaaat caatgaagca ggcagagagg tggtagggtc agcagaggct    480
ggagtggatg ctgcaagcgt ctctgaagaa tttagggctg accatccatt cctcttctgt    540
atcaagcaca tcgcaaccaa cgcctaagga tcctaa                              576
```

```
<210> SEQ ID NO 4
<211> LENGTH: 188
<212> TYPE: PRT
<213> ORGANISM: artificial
<220> FEATURE:
<223> OTHER INFORMATION: ZEBRA-OVA

<400> SEQUENCE: 4
```

```
Asp Ile His Met His His His His His His His Lys Arg Tyr Lys
1               5                   10                  15

Asn Arg Val Ala Ser Arg Lys Cys Arg Ala Lys Phe Lys Gln Leu Leu
                20                  25                  30

Gln His Tyr Arg Glu Val Ala Ala Ala Lys Ser Ser Glu Asn Asp Arg
            35                  40                  45

Leu Arg Leu Leu Leu Lys Gln Met Cys Leu Glu Asp Glu Val Ser Gly
50                  55                  60

Leu Glu Gln Leu Glu Ser Ile Ile Asn Phe Glu Lys Leu Thr Glu Trp
65                  70                  75                  80

Thr Ser Ser Asn Val Met Glu Glu Arg Lys Ile Lys Val Tyr Leu Pro
                85                  90                  95

Arg Met Lys Met Glu Glu Lys Tyr Asn Leu Thr Ser Val Leu Met Ala
            100                 105                 110

Met Gly Ile Thr Asp Val Phe Ser Ser Ala Asn Leu Ser Gly Ile
        115                 120                 125

Ser Ser Ala Glu Ser Leu Lys Ile Ser Gln Ala Val His Ala Ala His
130                 135                 140

Ala Glu Ile Asn Glu Ala Gly Arg Glu Val Val Gly Ser Ala Glu Ala
145                 150                 155                 160

Gly Val Asp Ala Ala Ser Val Ser Glu Glu Phe Arg Ala Asp His Pro
                165                 170                 175

Phe Leu Phe Cys Ile Lys His Ile Ala Thr Asn Ala
            180                 185
```

```
<210> SEQ ID NO 5
<211> LENGTH: 482
<212> TYPE: DNA
<213> ORGANISM: artificial
<220> FEATURE:
<223> OTHER INFORMATION: ZEBRA-MultiE

<400> SEQUENCE: 5
```

```
tatgcatcat catcatcatc atcatcacaa gcgatacaag aatcgggtgg cttccagaaa     60
atgccgggcc aagtttaagc aactgctgca gcactaccgt gaggtcgctg ctgccaaatc    120
atctgaaaat gacaggctgc gcctcctgtt gaagcagatg tgcaagcttg agcaactgga    180
atccatcatc aactttgaga actgacggga gtggaccgaa agcctgaaga ttagccaggc    240
cgtgcacgct gcgcatgcgg aaatcaacga agcgggtcgt gaggtcgtcg gtgttggcgc    300
actggagggc tctcgtaatc aagactggcg gggcgtgccg cgctgtggta tgtacggtct    360
gaatggtccg gacatttaca aaggcgttta tcagttcaaa agcgttgagt ttgatatgag    420
ccatctgatt actagcatta aggcggtgta taacttcgca acctgcggta tcttggccta    480
``` ac                                                                  482

<210> SEQ ID NO 6
<211> LENGTH: 159
<212> TYPE: PRT
<213> ORGANISM: artificial
<220> FEATURE:
<223> OTHER INFORMATION: ZEBRA-MultiE

<400> SEQUENCE: 6

Met His His His His His His His Lys Arg Tyr Lys Asn Arg Val
1               5                   10                  15

Ala Ser Arg Lys Cys Arg Ala Lys Phe Lys Gln Leu Leu Gln His Tyr
            20                  25                  30

Arg Glu Val Ala Ala Ala Lys Ser Ser Glu Asn Asp Arg Leu Arg Leu
        35                  40                  45

Leu Leu Lys Gln Met Cys Lys Leu Glu Gln Leu Glu Ser Ile Ile Asn
    50                  55                  60

Phe Glu Lys Leu Thr Glu Trp Thr Glu Ser Leu Lys Ile Ser Gln Ala
65                  70                  75                  80

Val His Ala Ala His Ala Glu Ile Asn Glu Ala Gly Arg Glu Val Val
                85                  90                  95

Gly Val Gly Ala Leu Glu Gly Ser Arg Asn Gln Asp Trp Leu Gly Val
            100                 105                 110

Pro Arg Cys Gly Met Tyr Gly Leu Asn Gly Pro Asp Ile Tyr Lys Gly
        115                 120                 125

Val Tyr Gln Phe Lys Ser Val Glu Phe Asp Met Ser His Leu Ile Thr
    130                 135                 140

Ser Ile Lys Ala Val Tyr Asn Phe Ala Thr Cys Gly Ile Leu Ala
145                 150                 155

<210> SEQ ID NO 7
<211> LENGTH: 135
<212> TYPE: DNA
<213> ORGANISM: artificial
<220> FEATURE:
<223> OTHER INFORMATION: ZEBRA fragment

<400> SEQUENCE: 7
aagcgataca agaatcgggt ggcttccaga aaatgccggg ccaagtttaa gcaactgctg      60
cagcactacc gtgaggtggc tgctgccaaa tcatctgaaa atgacaggct gcgcctcctg     120
ttgaagcaga tgtgc                                                      135

<210> SEQ ID NO 8
<211> LENGTH: 45
<212> TYPE: PRT
<213> ORGANISM: artificial
<220> FEATURE:
<223> OTHER INFORMATION: ZEBRA fragment

<400> SEQUENCE: 8

Lys Arg Tyr Lys Asn Arg Val Ala Ser Arg Lys Cys Arg Ala Lys Phe
1               5                   10                  15

Lys Gln Leu Leu Gln His Tyr Arg Glu Val Ala Ala Ala Lys Ser Ser
            20                  25                  30

Glu Asn Asp Arg Leu Arg Leu Leu Leu Lys Gln Met Cys
        35                  40                  45

```
<210> SEQ ID NO 9
<211> LENGTH: 9
<212> TYPE: PRT
<213> ORGANISM: Artificial sequence
<220> FEATURE:
<223> OTHER INFORMATION: chronic myeloid leukemia tumor antigen

<400> SEQUENCE: 9

Ser Ser Lys Ala Leu Gln Arg Pro Val
1               5

<210> SEQ ID NO 10
<211> LENGTH: 9
<212> TYPE: PRT
<213> ORGANISM: Artificial Sequence
<220> FEATURE:
<223> OTHER INFORMATION: chronic myeloid leukemia tumor antigen

<400> SEQUENCE: 10

Gly Phe Lys Gln Ser Ser Lys Ala Leu
1               5

<210> SEQ ID NO 11
<211> LENGTH: 17
<212> TYPE: PRT
<213> ORGANISM: Artificial Sequence
<220> FEATURE:
<223> OTHER INFORMATION: chronic myeloid leukemia tumor antigen

<400> SEQUENCE: 11

Ala Thr Gly Phe Lys Gln Ser Ser Lys Ala Leu Gln Arg Pro Val Ala
1               5                   10                  15

Ser

<210> SEQ ID NO 12
<211> LENGTH: 9
<212> TYPE: PRT
<213> ORGANISM: Artificial Sequence
<220> FEATURE:
<223> OTHER INFORMATION: acute lymphoblastic leukemia tumor antigen

<400> SEQUENCE: 12

Arg Ile Ala Glu Cys Ile Leu Gly Met
1               5

<210> SEQ ID NO 13
<211> LENGTH: 15
<212> TYPE: PRT
<213> ORGANISM: Artificial Sequence
<220> FEATURE:
<223> OTHER INFORMATION: acute lymphoblastic leukemia tumor antigen

<400> SEQUENCE: 13

Ile Gly Arg Ile Ala Glu Cys Ile Leu Gly Met Asn Pro Ser Arg
1               5                   10                  15

<210> SEQ ID NO 14
<211> LENGTH: 9
<212> TYPE: PRT
<213> ORGANISM: Artificial Sequence
<220> FEATURE:
<223> OTHER INFORMATION: glioma tumor antigen

<400> SEQUENCE: 14

Leu Glu Glu Lys Lys Gly Asn Tyr Val
1               5
```

<210> SEQ ID NO 15
<211> LENGTH: 9
<212> TYPE: PRT
<213> ORGANISM: Artificial Sequence
<220> FEATURE:
<223> OTHER INFORMATION: coiled-coil domain containing 110 (KM-HN-1)
      tumor antigen

<400> SEQUENCE: 15

Asn Tyr Asn Asn Phe Tyr Arg Phe Leu
1               5

<210> SEQ ID NO 16
<211> LENGTH: 10
<212> TYPE: PRT
<213> ORGANISM: Artificial Sequence
<220> FEATURE:
<223> OTHER INFORMATION: coiled-coil domain containing 110 (KM-HN-1)
      tumor antigen

<400> SEQUENCE: 16

Glu Tyr Ser Lys Glu Cys Leu Lys Glu Phe
1               5                   10

<210> SEQ ID NO 17
<211> LENGTH: 9
<212> TYPE: PRT
<213> ORGANISM: Artificial Sequence
<220> FEATURE:
<223> OTHER INFORMATION: coiled-coil domain containing 110 (KM-HN-1)
      tumor antigen

<400> SEQUENCE: 17

Glu Tyr Leu Ser Leu Ser Asp Lys Ile
1               5

<210> SEQ ID NO 18
<211> LENGTH: 11
<212> TYPE: PRT
<213> ORGANISM: Artificial Sequence
<220> FEATURE:
<223> OTHER INFORMATION: cancer/testis antigen 2 (LAGE-1) tumor antigen

<400> SEQUENCE: 18

Met Leu Met Ala Gln Glu Ala Leu Ala Phe Leu
1               5                   10

<210> SEQ ID NO 19
<211> LENGTH: 9
<212> TYPE: PRT
<213> ORGANISM: Artificial Sequence
<220> FEATURE:
<223> OTHER INFORMATION: cancer/testis antigen 2 (LAGE-1) tumor antigen

<400> SEQUENCE: 19

Ser Leu Leu Met Trp Ile Thr Gln Cys
1               5

<210> SEQ ID NO 20
<211> LENGTH: 10
<212> TYPE: PRT
<213> ORGANISM: Artificial Sequence
<220> FEATURE:
<223> OTHER INFORMATION: cancer/testis antigen 2 (LAGE-1) tumor antigen

<400> SEQUENCE: 20

Leu Ala Ala Gln Glu Arg Arg Val Pro Arg

<210> SEQ ID NO 21
<211> LENGTH: 9
<212> TYPE: PRT
<213> ORGANISM: Artificial Sequence
<220> FEATURE:
<223> OTHER INFORMATION: cancer/testis antigen 2 (LAGE-1) tumor antigen

<400> SEQUENCE: 21

Glu Leu Val Arg Arg Ile Leu Ser Arg
1               5

<210> SEQ ID NO 22
<211> LENGTH: 9
<212> TYPE: PRT
<213> ORGANISM: Artificial Sequence
<220> FEATURE:
<223> OTHER INFORMATION: cancer/testis antigen 2 (LAGE-1) tumor antigen

<400> SEQUENCE: 22

Ala Pro Arg Gly Val Arg Met Ala Val
1               5

<210> SEQ ID NO 23
<211> LENGTH: 14
<212> TYPE: PRT
<213> ORGANISM: Artificial Sequence
<220> FEATURE:
<223> OTHER INFORMATION: cancer/testis antigen 2 (LAGE-1) tumor antigen

<400> SEQUENCE: 23

Ser Leu Leu Met Trp Ile Thr Gln Cys Phe Leu Pro Val Phe
1               5                   10

<210> SEQ ID NO 24
<211> LENGTH: 20
<212> TYPE: PRT
<213> ORGANISM: Artificial Sequence
<220> FEATURE:
<223> OTHER INFORMATION: cancer/testis antigen 2 (LAGE-1) tumor antigen

<400> SEQUENCE: 24

Gln Gly Ala Met Leu Ala Ala Gln Glu Arg Arg Val Pro Arg Ala Ala
1               5                   10                  15

Glu Val Pro Arg
            20

<210> SEQ ID NO 25
<211> LENGTH: 18
<212> TYPE: PRT
<213> ORGANISM: Artificial Sequence
<220> FEATURE:
<223> OTHER INFORMATION: cancer/testis antigen 2 (LAGE-1) tumor antigen

<400> SEQUENCE: 25

Ala Ala Asp His Arg Gln Leu Gln Leu Ser Ile Ser Ser Cys Leu Gln
1               5                   10                  15

Gln Leu

<210> SEQ ID NO 26
<211> LENGTH: 22
<212> TYPE: PRT
<213> ORGANISM: Artificial Sequence
<220> FEATURE:
<223> OTHER INFORMATION: cancer/testis antigen 2 (LAGE-1) tumor antigen -continued

```
<400> SEQUENCE: 26

Cys Leu Ser Arg Arg Pro Trp Lys Arg Ser Trp Ser Ala Gly Ser Cys
1               5                   10                  15

Pro Gly Met Pro His Leu
            20

<210> SEQ ID NO 27
<211> LENGTH: 13
<212> TYPE: PRT
<213> ORGANISM: Artificial Sequence
<220> FEATURE:
<223> OTHER INFORMATION: cancer/testis antigen 2 (LAGE-1) tumor antigen

<400> SEQUENCE: 27

Ile Leu Ser Arg Asp Ala Ala Pro Leu Pro Arg Pro Gly
1               5                   10

<210> SEQ ID NO 28
<211> LENGTH: 14
<212> TYPE: PRT
<213> ORGANISM: Artificial Sequence
<220> FEATURE:
<223> OTHER INFORMATION: cancer/testis antigen 2 (LAGE-1) tumor antigen

<400> SEQUENCE: 28

Ala Gly Ala Thr Gly Gly Arg Gly Pro Arg Gly Ala Gly Ala
1               5                   10

<210> SEQ ID NO 29
<211> LENGTH: 9
<212> TYPE: PRT
<213> ORGANISM: Artificial Sequence
<220> FEATURE:
<223> OTHER INFORMATION: melanoma antigen family A, 1 (MAGE-A1) tumor
      antigen

<400> SEQUENCE: 29

Glu Ala Asp Pro Thr Gly His Ser Tyr
1               5

<210> SEQ ID NO 30
<211> LENGTH: 9
<212> TYPE: PRT
<213> ORGANISM: Artificial Sequence
<220> FEATURE:
<223> OTHER INFORMATION: melanoma antigen family A, 1 (MAGE-A1) tumor
      antigen

<400> SEQUENCE: 30

Lys Val Leu Glu Tyr Val Ile Lys Val
1               5

<210> SEQ ID NO 31
<211> LENGTH: 9
<212> TYPE: PRT
<213> ORGANISM: Artificial Sequence
<220> FEATURE:
<223> OTHER INFORMATION: melanoma antigen family A, 1 (MAGE-A1) tumor
      antigen

<400> SEQUENCE: 31

Ser Leu Phe Arg Ala Val Ile Thr Lys
1               5

<210> SEQ ID NO 32
```

```
<211> LENGTH: 10
<212> TYPE: PRT
<213> ORGANISM: Artificial Sequence
<220> FEATURE:
<223> OTHER INFORMATION: melanoma antigen family A, 1 (MAGE-A1) tumor
      antigen

<400> SEQUENCE: 32

Glu Val Tyr Asp Gly Arg Glu His Ser Ala
1               5                   10

<210> SEQ ID NO 33
<211> LENGTH: 9
<212> TYPE: PRT
<213> ORGANISM: Artificial Sequence
<220> FEATURE:
<223> OTHER INFORMATION: melanoma antigen family A, 1 (MAGE-A1) tumor
      antigen

<400> SEQUENCE: 33

Arg Val Arg Phe Phe Phe Pro Ser Leu
1               5

<210> SEQ ID NO 34
<211> LENGTH: 10
<212> TYPE: PRT
<213> ORGANISM: Artificial Sequence
<220> FEATURE:
<223> OTHER INFORMATION: melanoma antigen family A, 1 (MAGE-A1) tumor
      antigen

<400> SEQUENCE: 34

Arg Glu Pro Val Thr Lys Ala Glu Met Leu
1               5                   10

<210> SEQ ID NO 35
<211> LENGTH: 9
<212> TYPE: PRT
<213> ORGANISM: Artificial Sequence
<220> FEATURE:
<223> OTHER INFORMATION: melanoma antigen family A, 1 (MAGE-A1) tumor
      antigen

<400> SEQUENCE: 35

Asp Pro Ala Arg Tyr Glu Phe Leu Trp
1               5

<210> SEQ ID NO 36
<211> LENGTH: 11
<212> TYPE: PRT
<213> ORGANISM: Artificial Sequence
<220> FEATURE:
<223> OTHER INFORMATION: melanoma antigen family A, 1 (MAGE-A1) tumor
      antigen

<400> SEQUENCE: 36

Ile Thr Lys Lys Val Ala Asp Leu Val Gly Phe
1               5                   10

<210> SEQ ID NO 37
<211> LENGTH: 9
<212> TYPE: PRT
<213> ORGANISM: Artificial Sequence
<220> FEATURE:
<223> OTHER INFORMATION: melanoma antigen family A, 1 (MAGE-A1) tumor
      antigen

<400> SEQUENCE: 37
```

Ser Ala Phe Pro Thr Thr Ile Asn Phe
1               5

<210> SEQ ID NO 38
<211> LENGTH: 9
<212> TYPE: PRT
<213> ORGANISM: Artificial Sequence
<220> FEATURE:
<223> OTHER INFORMATION: melanoma antigen family A, 1 (MAGE-A1) tumor
      antigen

<400> SEQUENCE: 38

Ser Ala Tyr Gly Glu Pro Arg Lys Leu
1               5

<210> SEQ ID NO 39
<211> LENGTH: 15
<212> TYPE: PRT
<213> ORGANISM: Artificial Sequence
<220> FEATURE:
<223> OTHER INFORMATION: melanoma antigen family A, 1 (MAGE-A1) tumor
      antigen

<400> SEQUENCE: 39

Thr Ser Cys Ile Leu Glu Ser Leu Phe Arg Ala Val Ile Thr Lys
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: melanoma antigen family A, 1 (MAGE-A1) tumor
      antigen

<400> SEQUENCE: 40

Pro Arg Ala Leu Ala Glu Thr Ser Tyr Val Lys Val Leu Glu Tyr
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: melanoma antigen family A, 1 (MAGE-A1) tumor
      antigen

<400> SEQUENCE: 41

Phe Leu Leu Leu Lys Tyr Arg Ala Arg Glu Pro Val Thr Lys Ala Glu
1               5                   10                  15

<210> SEQ ID NO 42
<211> LENGTH: 12
<212> TYPE: PRT
<213> ORGANISM: Artificial Sequence
<220> FEATURE:
<223> OTHER INFORMATION: melanoma antigen family A, 1 (MAGE-A1) tumor
      antigen

<400> SEQUENCE: 42

Glu Tyr Val Ile Lys Val Ser Ala Arg Val Arg Phe
1               5                   10

<210> SEQ ID NO 43
<211> LENGTH: 10
<212> TYPE: PRT
<213> ORGANISM: Artificial Sequence
<220> FEATURE:

```
<223> OTHER INFORMATION: melanoma antigen family A, 2 (MAGE-A2) tumor
      antigen

<400> SEQUENCE: 43

Tyr Leu Gln Leu Val Phe Gly Ile Glu Val
1               5                   10

<210> SEQ ID NO 44
<211> LENGTH: 9
<212> TYPE: PRT
<213> ORGANISM: Artificial Sequence
<220> FEATURE:
<223> OTHER INFORMATION: melanoma antigen family A, 2 (MAGE-A2) tumor
      antigen

<400> SEQUENCE: 44

Glu Tyr Leu Gln Leu Val Phe Gly Ile
1               5

<210> SEQ ID NO 45
<211> LENGTH: 9
<212> TYPE: PRT
<213> ORGANISM: Artificial Sequence
<220> FEATURE:
<223> OTHER INFORMATION: melanoma antigen family A, 2 (MAGE-A2) tumor
      antigen

<400> SEQUENCE: 45

Glu Gly Asp Cys Ala Pro Glu Glu Lys
1               5

<210> SEQ ID NO 46
<211> LENGTH: 14
<212> TYPE: PRT
<213> ORGANISM: Artificial Sequence
<220> FEATURE:
<223> OTHER INFORMATION: melanoma antigen family A, 2 (MAGE-A2) tumor
      antigen

<400> SEQUENCE: 46

Leu Leu Lys Tyr Arg Ala Arg Glu Pro Val Thr Lys Ala Glu
1               5                   10

<210> SEQ ID NO 47
<211> LENGTH: 9
<212> TYPE: PRT
<213> ORGANISM: Artificial Sequence
<220> FEATURE:
<223> OTHER INFORMATION: melanoma antigen family A, 3 (MAGE-A3) tumor
      antigen

<400> SEQUENCE: 47

Glu Val Asp Pro Ile Gly His Leu Tyr
1               5

<210> SEQ ID NO 48
<211> LENGTH: 9
<212> TYPE: PRT
<213> ORGANISM: Artificial Sequence
<220> FEATURE:
<223> OTHER INFORMATION: melanoma antigen family A, 3 (MAGE-A3) tumor
      antigen

<400> SEQUENCE: 48

Phe Leu Trp Gly Pro Arg Ala Leu Val
1               5
```

```
<210> SEQ ID NO 49
<211> LENGTH: 9
<212> TYPE: PRT
<213> ORGANISM: Artificial Sequence
<220> FEATURE:
<223> OTHER INFORMATION: melanoma antigen family A, 3 (MAGE-A3) tumor
      antigen

<400> SEQUENCE: 49

Lys Val Ala Glu Leu Val His Phe Leu
1               5

<210> SEQ ID NO 50
<211> LENGTH: 9
<212> TYPE: PRT
<213> ORGANISM: Artificial Sequence
<220> FEATURE:
<223> OTHER INFORMATION: melanoma antigen family A, 3 (MAGE-A3) tumor
      antigen

<400> SEQUENCE: 50

Thr Phe Pro Asp Leu Glu Ser Glu Phe
1               5

<210> SEQ ID NO 51
<211> LENGTH: 9
<212> TYPE: PRT
<213> ORGANISM: Artificial Sequence
<220> FEATURE:
<223> OTHER INFORMATION: melanoma antigen family A, 3 (MAGE-A3) tumor
      antigen

<400> SEQUENCE: 51

Val Ala Glu Leu Val His Phe Leu Leu
1               5

<210> SEQ ID NO 52
<211> LENGTH: 10
<212> TYPE: PRT
<213> ORGANISM: Artificial Sequence
<220> FEATURE:
<223> OTHER INFORMATION: melanoma antigen family A, 3 (MAGE-A3) tumor
      antigen

<400> SEQUENCE: 52

Met Glu Val Asp Pro Ile Gly His Leu Tyr
1               5                   10

<210> SEQ ID NO 53
<211> LENGTH: 9
<212> TYPE: PRT
<213> ORGANISM: Artificial Sequence
<220> FEATURE:
<223> OTHER INFORMATION: melanoma antigen family A, 3 (MAGE-A3) tumor
      antigen

<400> SEQUENCE: 53

Ala Glu Leu Val His Phe Leu Leu Leu
1               5

<210> SEQ ID NO 54
<211> LENGTH: 9
<212> TYPE: PRT
<213> ORGANISM: Artificial Sequence
<220> FEATURE:
<223> OTHER INFORMATION: melanoma antigen family A, 3 (MAGE-A3) tumor
      antigen

<400> SEQUENCE: 54
```

Trp Gln Tyr Phe Phe Pro Val Ile Phe
1               5

<210> SEQ ID NO 55
<211> LENGTH: 16
<212> TYPE: PRT
<213> ORGANISM: Artificial Sequence
<220> FEATURE:
<223> OTHER INFORMATION: melanoma antigen family A, 3 (MAGE-A3) tumor
      antigen

<400> SEQUENCE: 55

Lys Lys Leu Leu Thr Gln His Phe Val Gln Glu Asn Tyr Leu Glu Tyr
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: melanoma antigen family A, 3 (MAGE-A3) tumor
      antigen

<400> SEQUENCE: 56

Ala Cys Tyr Glu Phe Leu Trp Gly Pro Arg Ala Leu Val Glu Thr Ser
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: melanoma antigen family A, 3 (MAGE-A3) tumor
      antigen

<400> SEQUENCE: 57

Arg Lys Val Ala Glu Leu Val His Phe Leu Leu Leu Lys Tyr Arg
1               5                   10                  15

<210> SEQ ID NO 58
<211> LENGTH: 12
<212> TYPE: PRT
<213> ORGANISM: Artificial Sequence
<220> FEATURE:
<223> OTHER INFORMATION: melanoma antigen family A, 3 (MAGE-A3) tumor
      antigen

<400> SEQUENCE: 58

Val Ile Phe Ser Lys Ala Ser Ser Ser Leu Gln Leu
1               5                   10

<210> SEQ ID NO 59
<211> LENGTH: 15
<212> TYPE: PRT
<213> ORGANISM: Artificial Sequence
<220> FEATURE:
<223> OTHER INFORMATION: melanoma antigen family A, 3 (MAGE-A3) tumor
      antigen

<400> SEQUENCE: 59

Val Phe Gly Ile Glu Leu Met Glu Val Asp Pro Ile Gly His Leu
1               5                   10                  15

<210> SEQ ID NO 60
<211> LENGTH: 15
<212> TYPE: PRT
<213> ORGANISM: Artificial Sequence -continued

```
<220> FEATURE:
<223> OTHER INFORMATION: melanoma antigen family A, 3 (MAGE-A3) tumor
      antigen

<400> SEQUENCE: 60

Gly Asp Asn Gln Ile Met Pro Lys Ala Gly Leu Leu Ile Ile Val
 1               5                  10                  15

<210> SEQ ID NO 61
<211> LENGTH: 15
<212> TYPE: PRT
<213> ORGANISM: Artificial Sequence
<220> FEATURE:
<223> OTHER INFORMATION: melanoma antigen family A, 3 (MAGE-A3) tumor
      antigen

<400> SEQUENCE: 61

Thr Ser Tyr Val Lys Val Leu His His Met Val Lys Ile Ser Gly
 1               5                  10                  15

<210> SEQ ID NO 62
<211> LENGTH: 16
<212> TYPE: PRT
<213> ORGANISM: Artificial Sequence
<220> FEATURE:
<223> OTHER INFORMATION: melanoma antigen family A, 3 (MAGE-A3) tumor
      antigen

<400> SEQUENCE: 62

Arg Lys Val Ala Glu Leu Val His Phe Leu Leu Leu Lys Tyr Arg Ala
 1               5                  10                  15

<210> SEQ ID NO 63
<211> LENGTH: 9
<212> TYPE: PRT
<213> ORGANISM: Artificial Sequence
<220> FEATURE:
<223> OTHER INFORMATION: melanoma antigen family A, 4 (MAGE-A4) tumor
      antigen

<400> SEQUENCE: 63

Glu Val Asp Pro Ala Ser Asn Thr Tyr
 1               5

<210> SEQ ID NO 64
<211> LENGTH: 10
<212> TYPE: PRT
<213> ORGANISM: Artificial Sequence
<220> FEATURE:
<223> OTHER INFORMATION: melanoma antigen family A, 4 (MAGE-A4) tumor
      antigen

<400> SEQUENCE: 64

Gly Val Tyr Asp Gly Arg Glu His Thr Val
 1               5                  10

<210> SEQ ID NO 65
<211> LENGTH: 9
<212> TYPE: PRT
<213> ORGANISM: Artificial Sequence
<220> FEATURE:
<223> OTHER INFORMATION: melanoma antigen family A, 4 (MAGE-A4) tumor
      antigen

<400> SEQUENCE: 65

Asn Tyr Lys Arg Cys Phe Pro Val Ile
 1               5
```

<210> SEQ ID NO 66
<211> LENGTH: 8
<212> TYPE: PRT
<213> ORGANISM: Artificial Sequence
<220> FEATURE:
<223> OTHER INFORMATION: melanoma antigen family A, 4 (MAGE-A4) tumor
      antigen

<400> SEQUENCE: 66

Ser Glu Ser Leu Lys Met Ile Phe
1               5

<210> SEQ ID NO 67
<211> LENGTH: 9
<212> TYPE: PRT
<213> ORGANISM: Artificial Sequence
<220> FEATURE:
<223> OTHER INFORMATION: melanoma antigen family A, 6 (MAGE-A6) tumor
      antigen

<400> SEQUENCE: 67

Met Val Lys Ile Ser Gly Gly Pro Arg
1               5

<210> SEQ ID NO 68
<211> LENGTH: 9
<212> TYPE: PRT
<213> ORGANISM: Artificial Sequence
<220> FEATURE:
<223> OTHER INFORMATION: melanoma antigen family A, 6 (MAGE-A6) tumor
      antigen

<400> SEQUENCE: 68

Glu Val Asp Pro Ile Gly His Val Tyr
1               5

<210> SEQ ID NO 69
<211> LENGTH: 9
<212> TYPE: PRT
<213> ORGANISM: Artificial Sequence
<220> FEATURE:
<223> OTHER INFORMATION: melanoma antigen family A, 6 (MAGE-A6) tumor
      antigen

<400> SEQUENCE: 69

Ile Ser Gly Gly Pro Arg Ile Ser Tyr
1               5

<210> SEQ ID NO 70
<211> LENGTH: 9
<212> TYPE: PRT
<213> ORGANISM: Artificial Sequence
<220> FEATURE:
<223> OTHER INFORMATION: melanoma antigen family A, 9 (MAGE-A9) tumor
      antigen

<400> SEQUENCE: 70

Ala Leu Ser Val Met Gly Val Tyr Val
1               5

<210> SEQ ID NO 71
<211> LENGTH: 9
<212> TYPE: PRT
<213> ORGANISM: Artificial Sequence
<220> FEATURE:
<223> OTHER INFORMATION: melanoma antigen family A, 10 (MAGE-A10) tumor
      antigen

```
<400> SEQUENCE: 71

Gly Leu Tyr Asp Gly Met Glu His Leu
1               5

<210> SEQ ID NO 72
<211> LENGTH: 9
<212> TYPE: PRT
<213> ORGANISM: Artificial Sequence
<220> FEATURE:
<223> OTHER INFORMATION: melanoma antigen family A, 12 (MAGE-A12) tumor
      antigen

<400> SEQUENCE: 72

Val Arg Ile Gly His Leu Tyr Ile Leu
1               5

<210> SEQ ID NO 73
<211> LENGTH: 15
<212> TYPE: PRT
<213> ORGANISM: Artificial Sequence
<220> FEATURE:
<223> OTHER INFORMATION: melanoma antigen family A, 12 (MAGE-A12) tumor
      antigen

<400> SEQUENCE: 73

Arg Glu Pro Phe Thr Lys Ala Glu Met Leu Gly Ser Val Ile Arg
1               5                   10                  15

<210> SEQ ID NO 74
<211> LENGTH: 14
<212> TYPE: PRT
<213> ORGANISM: Artificial Sequence
<220> FEATURE:
<223> OTHER INFORMATION: melanoma antigen family A, 12 (MAGE-A12) tumor
      antigen

<400> SEQUENCE: 74

Ala Glu Leu Val His Phe Leu Leu Leu Lys Tyr Arg Ala Arg
1               5                   10

<210> SEQ ID NO 75
<211> LENGTH: 13
<212> TYPE: PRT
<213> ORGANISM: Artificial Sequence
<220> FEATURE:
<223> OTHER INFORMATION: melanoma antigen family C, 1 (MAGE-C1) tumor
      antigen

<400> SEQUENCE: 75

Ser Ser Ala Leu Leu Ser Ile Phe Gln Ser Ser Pro Glu
1               5                   10

<210> SEQ ID NO 76
<211> LENGTH: 9
<212> TYPE: PRT
<213> ORGANISM: Artificial Sequence
<220> FEATURE:
<223> OTHER INFORMATION: melanoma antigen family C, 1 (MAGE-C1) tumor
      antigen

<400> SEQUENCE: 76

Ser Phe Ser Tyr Thr Leu Leu Ser Leu
1               5

<210> SEQ ID NO 77
<211> LENGTH: 9
<212> TYPE: PRT
```

-continued

```
<213> ORGANISM: Artificial Sequence
<220> FEATURE:
<223> OTHER INFORMATION: melanoma antigen family C, 1 (MAGE-C1) tumor
      antigen

<400> SEQUENCE: 77

Val Ser Ser Phe Phe Ser Tyr Thr Leu
1               5

<210> SEQ ID NO 78
<211> LENGTH: 10
<212> TYPE: PRT
<213> ORGANISM: Artificial Sequence
<220> FEATURE:
<223> OTHER INFORMATION: melanoma antigen family C, 2 (MAGE-C2) tumor
      antigen

<400> SEQUENCE: 78

Leu Leu Phe Gly Leu Ala Leu Ile Glu Val
1               5                   10

<210> SEQ ID NO 79
<211> LENGTH: 9
<212> TYPE: PRT
<213> ORGANISM: Artificial Sequence
<220> FEATURE:
<223> OTHER INFORMATION: melanoma antigen family C, 2 (MAGE-C2) tumor
      antigen

<400> SEQUENCE: 79

Ala Leu Lys Asp Val Glu Glu Arg Val
1               5

<210> SEQ ID NO 80
<211> LENGTH: 9
<212> TYPE: PRT
<213> ORGANISM: Artificial Sequence
<220> FEATURE:
<223> OTHER INFORMATION: melanoma antigen family C, 2 (MAGE-C2) tumor
      antigen

<400> SEQUENCE: 80

Ser Glu Ser Ile Lys Lys Lys Val Leu
1               5

<210> SEQ ID NO 81
<211> LENGTH: 10
<212> TYPE: PRT
<213> ORGANISM: Artificial Sequence
<220> FEATURE:
<223> OTHER INFORMATION: cancer/testis antigen 1B (NY-ESO 1/ LAGE-2)
      tumor antigen

<400> SEQUENCE: 81

Ala Ser Gly Pro Gly Gly Gly Ala Pro Arg
1               5                   10

<210> SEQ ID NO 82
<211> LENGTH: 10
<212> TYPE: PRT
<213> ORGANISM: Artificial Sequence
<220> FEATURE:
<223> OTHER INFORMATION: cancer/testis antigen 1B (NY-ESO 1/ LAGE-2)
      tumor antigen

<400> SEQUENCE: 82

Thr Val Ser Gly Asn Ile Leu Thr Ile Arg
1               5                   10
```

<210> SEQ ID NO 83
<211> LENGTH: 13
<212> TYPE: PRT
<213> ORGANISM: Artificial Sequence
<220> FEATURE:
<223> OTHER INFORMATION: cancer/testis antigen 1B (NY-ESO 1/ LAGE-2)
      tumor antigen

<400> SEQUENCE: 83

Ala Pro Arg Gly Pro His Gly Gly Ala Ala Ser Gly Leu
1               5                   10

<210> SEQ ID NO 84
<211> LENGTH: 9
<212> TYPE: PRT
<213> ORGANISM: Artificial Sequence
<220> FEATURE:
<223> OTHER INFORMATION: cancer/testis antigen 1B (NY-ESO 1/ LAGE-2)
      tumor antigen

<400> SEQUENCE: 84

Met Pro Phe Ala Thr Pro Met Glu Ala
1               5

<210> SEQ ID NO 85
<211> LENGTH: 12
<212> TYPE: PRT
<213> ORGANISM: Artificial Sequence
<220> FEATURE:
<223> OTHER INFORMATION: cancer/testis antigen 1B (NY-ESO 1/ LAGE-2)
      tumor antigen

<400> SEQUENCE: 85

Lys Glu Phe Thr Val Ser Gly Asn Ile Leu Thr Ile
1               5                   10

<210> SEQ ID NO 86
<211> LENGTH: 9
<212> TYPE: PRT
<213> ORGANISM: Artificial Sequence
<220> FEATURE:
<223> OTHER INFORMATION: cancer/testis antigen 1B (NY-ESO 1/ LAGE-2)
      tumor antigen

<400> SEQUENCE: 86

Leu Ala Met Pro Phe Ala Thr Pro Met
1               5

<210> SEQ ID NO 87
<211> LENGTH: 9
<212> TYPE: PRT
<213> ORGANISM: Artificial Sequence
<220> FEATURE:
<223> OTHER INFORMATION: cancer/testis antigen 1B (NY-ESO 1/ LAGE-2)
      tumor antigen

<400> SEQUENCE: 87

Ala Arg Gly Pro Glu Ser Arg Leu Leu
1               5

<210> SEQ ID NO 88
<211> LENGTH: 25
<212> TYPE: PRT
<213> ORGANISM: Artificial Sequence
<220> FEATURE:
<223> OTHER INFORMATION: cancer/testis antigen 1B (NY-ESO 1/ LAGE-2)
      tumor antigens -continued

<400> SEQUENCE: 88

Leu Leu Glu Phe Tyr Leu Ala Met Pro Phe Ala Thr Pro Met Glu Ala
1               5                   10                  15

Glu Leu Ala Arg Arg Ser Leu Ala Gln
            20                  25

<210> SEQ ID NO 89
<211> LENGTH: 12
<212> TYPE: PRT
<213> ORGANISM: Artificial Sequence
<220> FEATURE:
<223> OTHER INFORMATION: cancer/testis antigen 1B (NY-ESO 1/ LAGE-2)
      tumor antigen

<400> SEQUENCE: 89

Glu Phe Tyr Leu Ala Met Pro Phe Ala Thr Pro Met
1               5                   10

<210> SEQ ID NO 90
<211> LENGTH: 25
<212> TYPE: PRT
<213> ORGANISM: Artificial Sequence
<220> FEATURE:
<223> OTHER INFORMATION: cancer/testis antigen 1B (NY-ESO 1/ LAGE-2)
      tumor antigen

<400> SEQUENCE: 90

Pro Gly Val Leu Leu Lys Glu Phe Thr Val Ser Gly Asn Ile Leu Thr
1               5                   10                  15

Ile Arg Leu Thr Ala Ala Asp His Arg
            20                  25

<210> SEQ ID NO 91
<211> LENGTH: 12
<212> TYPE: PRT
<213> ORGANISM: Artificial Sequence
<220> FEATURE:
<223> OTHER INFORMATION: cancer/testis antigen 1B (NY-ESO 1/ LAGE-2)
      tumor antigen

<400> SEQUENCE: 91

Arg Leu Leu Glu Phe Tyr Leu Ala Met Pro Phe Ala
1               5                   10

<210> SEQ ID NO 92
<211> LENGTH: 13
<212> TYPE: PRT
<213> ORGANISM: Artificial Sequence
<220> FEATURE:
<223> OTHER INFORMATION: cancer/testis antigen 1B (NY-ESO 1/ LAGE-2)
      tumor antigen

<400> SEQUENCE: 92

Pro Phe Ala Thr Pro Met Glu Ala Glu Leu Ala Arg Arg
1               5                   10

<210> SEQ ID NO 93
<211> LENGTH: 20
<212> TYPE: PRT
<213> ORGANISM: Artificial Sequence
<220> FEATURE:
<223> OTHER INFORMATION: cancer/testis antigen 1B (NY-ESO 1/ LAGE-2)
      tumor antigen

<400> SEQUENCE: 93

```
Pro Gly Val Leu Leu Lys Glu Phe Thr Val Ser Gly Asn Ile Leu Thr
1               5                   10                  15

Ile Arg Leu Thr
            20

<210> SEQ ID NO 94
<211> LENGTH: 10
<212> TYPE: PRT
<213> ORGANISM: Artificial Sequence
<220> FEATURE:
<223> OTHER INFORMATION: cancer/testis antigen 1B (NY-ESO 1/ LAGE-2)
      tumor antigen

<400> SEQUENCE: 94

Val Leu Leu Lys Glu Phe Thr Val Ser Gly
1               5                   10

<210> SEQ ID NO 95
<211> LENGTH: 15
<212> TYPE: PRT
<213> ORGANISM: Artificial Sequence
<220> FEATURE:
<223> OTHER INFORMATION: cancer/testis antigen 1B (NY-ESO 1/ LAGE-2)
      tumor antigen

<400> SEQUENCE: 95

Leu Lys Glu Phe Thr Val Ser Gly Asn Ile Leu Thr Ile Arg Leu
1               5                   10                  15

<210> SEQ ID NO 96
<211> LENGTH: 11
<212> TYPE: PRT
<213> ORGANISM: Artificial Sequence
<220> FEATURE:
<223> OTHER INFORMATION: cancer/testis antigen 1B (NY-ESO 1/ LAGE-2)
      tumor antigen

<400> SEQUENCE: 96

Lys Glu Phe Thr Val Ser Gly Asn Ile Leu Thr
1               5                   10

<210> SEQ ID NO 97
<211> LENGTH: 14
<212> TYPE: PRT
<213> ORGANISM: Artificial Sequence
<220> FEATURE:
<223> OTHER INFORMATION: cancer/testis antigen 1B (NY-ESO 1/ LAGE-2)
      tumor antigen

<400> SEQUENCE: 97

Leu Leu Glu Phe Tyr Leu Ala Met Pro Phe Ala Thr Pro Met
1               5                   10

<210> SEQ ID NO 98
<211> LENGTH: 9
<212> TYPE: PRT
<213> ORGANISM: Artificial Sequence
<220> FEATURE:
<223> OTHER INFORMATION: synovial sarcoma, X breakpoint 2 (SSX-2) tumor
      antigen

<400> SEQUENCE: 98

Lys Ala Ser Glu Lys Ile Phe Tyr Val
1               5

<210> SEQ ID NO 99
<211> LENGTH: 16
```

```
<212> TYPE: PRT
<213> ORGANISM: Artificial Sequence
<220> FEATURE:
<223> OTHER INFORMATION: synovial sarcoma, X breakpoint 2 (SSX-2) tumor
      antigen

<400> SEQUENCE: 99

Glu Lys Ile Gln Lys Ala Phe Asp Asp Ile Ala Lys Tyr Phe Ser Lys
1               5                   10                  15

<210> SEQ ID NO 100
<211> LENGTH: 18
<212> TYPE: PRT
<213> ORGANISM: Artificial Sequence
<220> FEATURE:
<223> OTHER INFORMATION: synovial sarcoma, X breakpoint 2 (SSX-2) tumor
      antigen

<400> SEQUENCE: 100

Trp Glu Lys Met Lys Ala Ser Glu Lys Ile Phe Tyr Val Tyr Met Lys
1               5                   10                  15

Arg Lys

<210> SEQ ID NO 101
<211> LENGTH: 15
<212> TYPE: PRT
<213> ORGANISM: Artificial Sequence
<220> FEATURE:
<223> OTHER INFORMATION: synovial sarcoma, X breakpoint 2 (SSX-2) tumor
      antigen

<400> SEQUENCE: 101

Lys Ile Phe Tyr Val Tyr Met Lys Arg Lys Tyr Glu Ala Met Thr
1               5                   10                  15

<210> SEQ ID NO 102
<211> LENGTH: 14
<212> TYPE: PRT
<213> ORGANISM: Artificial Sequence
<220> FEATURE:
<223> OTHER INFORMATION: synovial sarcoma, X breakpoint 2 (SSX-2) tumor
      antigen

<400> SEQUENCE: 102

Lys Ile Phe Tyr Val Tyr Met Lys Arg Lys Tyr Glu Ala Met
1               5                   10

<210> SEQ ID NO 103
<211> LENGTH: 20
<212> TYPE: PRT
<213> ORGANISM: Artificial Sequence
<220> FEATURE:
<223> OTHER INFORMATION: synovial sarcoma, X breakpoint 4 (SSX-4) tumor
      antigen

<400> SEQUENCE: 103

Ile Asn Lys Thr Ser Gly Pro Lys Arg Gly Lys His Ala Trp Thr His
1               5                   10                  15

Arg Leu Arg Glu
            20

<210> SEQ ID NO 104
<211> LENGTH: 20
<212> TYPE: PRT
<213> ORGANISM: Artificial Sequence
<220> FEATURE:
<223> OTHER INFORMATION: synovial sarcoma, X breakpoint 4 (SSX-4) tumor
``` antigen

<400> SEQUENCE: 104

Tyr Phe Ser Lys Lys Glu Trp Glu Lys Met Lys Ser Ser Glu Lys Ile
1               5                   10                  15

Val Tyr Val Tyr
            20

<210> SEQ ID NO 105
<211> LENGTH: 20
<212> TYPE: PRT
<213> ORGANISM: Artificial Sequence
<220> FEATURE:
<223> OTHER INFORMATION: synovial sarcoma, X breakpoint 4 (SSX-4) tumor
      antigen

<400> SEQUENCE: 105

Met Lys Leu Asn Tyr Glu Val Met Thr Lys Leu Gly Phe Lys Val Thr
1               5                   10                  15

Leu Pro Pro Phe
            20

<210> SEQ ID NO 106
<211> LENGTH: 20
<212> TYPE: PRT
<213> ORGANISM: Artificial Sequence
<220> FEATURE:
<223> OTHER INFORMATION: synovial sarcoma, X breakpoint 4 (SSX-4) tumor
      antigen

<400> SEQUENCE: 106

Lys His Ala Trp Thr His Arg Leu Arg Glu Arg Lys Gln Leu Val Val
1               5                   10                  15

Tyr Glu Glu Ile
            20

<210> SEQ ID NO 107
<211> LENGTH: 20
<212> TYPE: PRT
<213> ORGANISM: Artificial Sequence
<220> FEATURE:
<223> OTHER INFORMATION: synovial sarcoma, X breakpoint 4 (SSX-4) tumor
      antigen

<400> SEQUENCE: 107

Leu Gly Phe Lys Val Thr Leu Pro Pro Phe Met Arg Ser Lys Arg Ala
1               5                   10                  15

Ala Asp Phe His
            20

<210> SEQ ID NO 108
<211> LENGTH: 20
<212> TYPE: PRT
<213> ORGANISM: Artificial Sequence
<220> FEATURE:
<223> OTHER INFORMATION: synovial sarcoma, X breakpoint 4 (SSX-4) tumor
      antigen

<400> SEQUENCE: 108

Lys Ser Ser Glu Lys Ile Val Tyr Val Tyr Met Lys Leu Asn Tyr Glu
1               5                   10                  15

Val Met Thr Lys
            20

```
<210> SEQ ID NO 109
<211> LENGTH: 9
<212> TYPE: PRT
<213> ORGANISM: Artificial Sequence
<220> FEATURE:
<223> OTHER INFORMATION: Transient axonal glycoprotein 1 (TAG-1) tumor
      antigen

<400> SEQUENCE: 109

Ser Leu Gly Trp Leu Phe Leu Leu Leu
1               5

<210> SEQ ID NO 110
<211> LENGTH: 9
<212> TYPE: PRT
<213> ORGANISM: Artificial Sequence
<220> FEATURE:
<223> OTHER INFORMATION: Transient axonal glycoprotein 1 (TAG-1) tumor
      antigen

<400> SEQUENCE: 110

Leu Ser Arg Leu Ser Asn Arg Leu Leu
1               5

<210> SEQ ID NO 111
<211> LENGTH: 15
<212> TYPE: PRT
<213> ORGANISM: Artificial Sequence
<220> FEATURE:
<223> OTHER INFORMATION: Taxol-resistant-associated gene 3 (TRAG-3)
      tumor antigen

<400> SEQUENCE: 111

Cys Glu Phe His Ala Cys Trp Pro Ala Phe Thr Val Leu Gly Glu
1               5                   10                  15

<210> SEQ ID NO 112
<211> LENGTH: 8
<212> TYPE: PRT
<213> ORGANISM: Artificial Sequence
<220> FEATURE:
<223> OTHER INFORMATION: Gut carcinoma differentiation antigen

<400> SEQUENCE: 112

Tyr Leu Ser Gly Ala Asn Leu Asn
1               5

<210> SEQ ID NO 113
<211> LENGTH: 9
<212> TYPE: PRT
<213> ORGANISM: Artificial Sequence
<220> FEATURE:
<223> OTHER INFORMATION: Gut carcinoma differentiation antigen

<400> SEQUENCE: 113

Ile Met Ile Gly Val Leu Val Gly Val
1               5

<210> SEQ ID NO 114
<211> LENGTH: 9
<212> TYPE: PRT
<213> ORGANISM: Artificial Sequence
<220> FEATURE:
<223> OTHER INFORMATION: Gut carcinoma differentiation antigen

<400> SEQUENCE: 114

Gly Val Leu Val Gly Val Ala Leu Ile
1               5
```

```
<210> SEQ ID NO 115
<211> LENGTH: 9
<212> TYPE: PRT
<213> ORGANISM: Artificial Sequence
<220> FEATURE:
<223> OTHER INFORMATION: Gut carcinoma differentiation antigen

<400> SEQUENCE: 115

His Leu Phe Gly Tyr Ser Trp Tyr Lys
1               5

<210> SEQ ID NO 116
<211> LENGTH: 10
<212> TYPE: PRT
<213> ORGANISM: Artificial Sequence
<220> FEATURE:
<223> OTHER INFORMATION: Gut carcinoma differentiation antigen

<400> SEQUENCE: 116

Gln Tyr Ser Trp Phe Val Asn Gly Thr Phe
1               5                   10

<210> SEQ ID NO 117
<211> LENGTH: 9
<212> TYPE: PRT
<213> ORGANISM: Artificial Sequence
<220> FEATURE:
<223> OTHER INFORMATION: Gut carcinoma differentiation antigen

<400> SEQUENCE: 117

Thr Tyr Ala Cys Phe Val Ser Asn Leu
1               5

<210> SEQ ID NO 118
<211> LENGTH: 15
<212> TYPE: PRT
<213> ORGANISM: Artificial Sequence
<220> FEATURE:
<223> OTHER INFORMATION: Gut carcinoma differentiation antigen

<400> SEQUENCE: 118

Ala Tyr Val Cys Gly Ile Gln Asn Ser Val Ser Ala Asn Arg Ser
1               5                   10                  15

<210> SEQ ID NO 119
<211> LENGTH: 25
<212> TYPE: PRT
<213> ORGANISM: Artificial Sequence
<220> FEATURE:
<223> OTHER INFORMATION: Gut carcinoma differentiation antigen

<400> SEQUENCE: 119

Asp Thr Gly Phe Tyr Thr Leu His Val Ile Lys Ser Asp Leu Val Asn
1               5                   10                  15

Glu Glu Ala Thr Gly Gln Phe Arg Val
            20                  25

<210> SEQ ID NO 120
<211> LENGTH: 15
<212> TYPE: PRT
<213> ORGANISM: Artificial Sequence
<220> FEATURE:
<223> OTHER INFORMATION: Gut carcinoma differentiation antigen

<400> SEQUENCE: 120
```

```
Tyr Ser Trp Arg Ile Asn Gly Ile Pro Gln Gln His Thr Gln Val
1               5                   10                  15

<210> SEQ ID NO 121
<211> LENGTH: 13
<212> TYPE: PRT
<213> ORGANISM: Artificial Sequence
<220> FEATURE:
<223> OTHER INFORMATION: Gut carcinoma differerntiation antigen

<400> SEQUENCE: 121

Thr Tyr Tyr Arg Pro Gly Val Asn Leu Ser Leu Ser Cys
1               5                   10

<210> SEQ ID NO 122
<211> LENGTH: 13
<212> TYPE: PRT
<213> ORGANISM: Artificial Sequence
<220> FEATURE:
<223> OTHER INFORMATION: Gut carcinoma differentiation antigen

<400> SEQUENCE: 122

Glu Ile Ile Tyr Pro Asn Ala Ser Leu Leu Ile Gln Asn
1               5                   10

<210> SEQ ID NO 123
<211> LENGTH: 15
<212> TYPE: PRT
<213> ORGANISM: Artificial Sequence
<220> FEATURE:
<223> OTHER INFORMATION: Gut carcinoma differentiation antigen

<400> SEQUENCE: 123

Tyr Ala Cys Phe Val Ser Asn Leu Ala Thr Gly Arg Asn Asn Ser
1               5                   10                  15

<210> SEQ ID NO 124
<211> LENGTH: 13
<212> TYPE: PRT
<213> ORGANISM: Artificial Sequence
<220> FEATURE:
<223> OTHER INFORMATION: Gut carcinoma differentiation antigen

<400> SEQUENCE: 124

Leu Trp Trp Val Asn Asn Gln Ser Leu Pro Val Ser Pro
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Gut carcinoma differerntiation antigen

<400> SEQUENCE: 125

Asn Ser Ile Val Lys Ser Ile Thr Val Ser Ala Ser Gly
1               5                   10

<210> SEQ ID NO 126
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 126

Lys Thr Trp Gly Gln Tyr Trp Gln Val
```

```
1               5
```

<210> SEQ ID NO 127
<211> LENGTH: 10
<212> TYPE: PRT
<213> ORGANISM: Artificial Sequence
<220> FEATURE:
<223> OTHER INFORMATION: Melanoma differentiation antigen

<400> SEQUENCE: 127

```
Ala Met Leu Gly Thr His Thr Met Glu Val
1               5                   10
```

<210> SEQ ID NO 128
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 128

```
Ile Thr Asp Gln Val Pro Phe Ser Val
1               5
```

<210> SEQ ID NO 129
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 129

```
Tyr Leu Glu Pro Gly Pro Val Thr Ala
1               5
```

<210> SEQ ID NO 130
<211> LENGTH: 10
<212> TYPE: PRT
<213> ORGANISM: Artificial Sequence
<220> FEATURE:
<223> OTHER INFORMATION: Melanoma differentiation antigen

<400> SEQUENCE: 130

```
Leu Leu Asp Gly Thr Ala Thr Leu Arg Leu
1               5                   10
```

<210> SEQ ID NO 131
<211> LENGTH: 10
<212> TYPE: PRT
<213> ORGANISM: Artificial Sequence
<220> FEATURE:
<223> OTHER INFORMATION: Melanoma differentiation antigen

<400> SEQUENCE: 131

```
Val Leu Tyr Arg Tyr Gly Ser Phe Ser Val
1               5                   10
```

<210> SEQ ID NO 132
<211> LENGTH: 10
<212> TYPE: PRT
<213> ORGANISM: Artificial Sequence
<220> FEATURE:
<223> OTHER INFORMATION: Melanoma differentiation antigen

<400> SEQUENCE: 132

```
Ser Leu Ala Asp Thr Asn Ser Leu Ala Val
1               5                   10
```

<210> SEQ ID NO 133
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 133

Arg Leu Met Lys Gln Asp Phe Ser Val
1               5

<210> SEQ ID NO 134
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 134

Arg Leu Pro Arg Ile Phe Cys Ser Cys
1               5

<210> SEQ ID NO 135
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 135

Leu Ile Tyr Arg Arg Arg Leu Met Lys
1               5

<210> SEQ ID NO 136
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 136

Ala Leu Leu Ala Val Gly Ala Thr Lys
1               5

<210> SEQ ID NO 137
<211> LENGTH: 10
<212> TYPE: PRT
<213> ORGANISM: Artificial Sequence
<220> FEATURE:
<223> OTHER INFORMATION: Melanoma differentiation antigen

<400> SEQUENCE: 137

Ile Ala Leu Asn Phe Pro Gly Ser Gln Lys
1               5                   10

<210> SEQ ID NO 138
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 138

Ala Leu Asn Phe Pro Gly Ser Gln Lys
1               5

<210> SEQ ID NO 139
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 139

Val Tyr Phe Phe Leu Pro Asp His Leu
1               5

<210> SEQ ID NO 140
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 140

Arg Thr Lys Gln Leu Tyr Pro Glu Trp
1               5

<210> SEQ ID NO 141
<211> LENGTH: 10
<212> TYPE: PRT
<213> ORGANISM: Artificial Sequence
<220> FEATURE:
<223> OTHER INFORMATION: Melanoma differentiation antigen

<400> SEQUENCE: 141

His Thr Met Glu Val Thr Val Tyr His Arg
1               5                   10

<210> SEQ ID NO 142
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 142

Ser Ser Pro Gly Cys Gln Pro Pro Ala
1               5

<210> SEQ ID NO 143
<211> LENGTH: 10
<212> TYPE: PRT
<213> ORGANISM: Artificial Sequence
<220> FEATURE:
<223> OTHER INFORMATION: Melanoma differentiation antigen

<400> SEQUENCE: 143

Val Pro Leu Asp Cys Val Leu Tyr Arg Tyr
1               5                   10

<210> SEQ ID NO 144
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 144

Leu Pro His Ser Ser His Trp Leu
1               5

```
<210> SEQ ID NO 145
<211> LENGTH: 8
<212> TYPE: PRT
<213> ORGANISM: Artificial Sequence
<220> FEATURE:
<223> OTHER INFORMATION: Melanoma differentiation antigen

<400> SEQUENCE: 145

Ser Asn Asp Gly Pro Thr Leu Ile
1               5

<210> SEQ ID NO 146
<211> LENGTH: 15
<212> TYPE: PRT
<213> ORGANISM: Artificial Sequence
<220> FEATURE:
<223> OTHER INFORMATION: Melanoma differentiation antigen

<400> SEQUENCE: 146

Gly Arg Ala Met Leu Gly Thr His Thr Met Glu Val Thr Val Tyr
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Melanoma differentiation antigen

<400> SEQUENCE: 147

Trp Asn Arg Gln Leu Tyr Pro Glu Trp Thr Glu Ala Gln Arg Leu Asp
1               5                   10                  15

<210> SEQ ID NO 148
<211> LENGTH: 18
<212> TYPE: PRT
<213> ORGANISM: Artificial Sequence
<220> FEATURE:
<223> OTHER INFORMATION: Melanoma differentiation antigen

<400> SEQUENCE: 148

Thr Thr Glu Trp Val Glu Thr Thr Ala Arg Glu Leu Pro Ile Pro Glu
1               5                   10                  15

Pro Glu

<210> SEQ ID NO 149
<211> LENGTH: 17
<212> TYPE: PRT
<213> ORGANISM: Artificial Sequence
<220> FEATURE:
<223> OTHER INFORMATION: Melanoma differentiation antigen

<400> SEQUENCE: 149

Thr Gly Arg Ala Met Leu Gly Thr His Thr Met Glu Val Thr Val Tyr
1               5                   10                  15

His

<210> SEQ ID NO 150
<211> LENGTH: 15
<212> TYPE: PRT
<213> ORGANISM: Artificial Sequence
<220> FEATURE:
<223> OTHER INFORMATION: Prostate cancer differentiation antigen

<400> SEQUENCE: 150

Ser Val Ser Glu Ser Asp Thr Ile Arg Ser Ile Ser Ile Ala Ser
```

```
1               5                  10                 15
```

<210> SEQ ID NO 151
<211> LENGTH: 15
<212> TYPE: PRT
<213> ORGANISM: Artificial Sequence
<220> FEATURE:
<223> OTHER INFORMATION: Prostate cancer differentiation antigen

<400> SEQUENCE: 151

```
Leu Leu Ala Asn Gly Arg Met Pro Thr Val Leu Gln Cys Val Asn
1               5                  10                 15
```

<210> SEQ ID NO 152
<211> LENGTH: 15
<212> TYPE: PRT
<213> ORGANISM: Artificial Sequence
<220> FEATURE:
<223> OTHER INFORMATION: Prostate cancer differentiation antigen

<400> SEQUENCE: 152

```
Arg Met Pro Thr Val Leu Gln Cys Val Asn Val Ser Val Val Ser
1               5                  10                 15
```

<210> SEQ ID NO 153
<211> LENGTH: 9
<212> TYPE: PRT
<213> ORGANISM: Artificial Sequence
<220> FEATURE:
<223> OTHER INFORMATION: Breast cancer differentiation antigen

<400> SEQUENCE: 153

```
Pro Leu Leu Glu Asn Val Ile Ser Lys
1               5
```

<210> SEQ ID NO 154
<211> LENGTH: 10
<212> TYPE: PRT
<213> ORGANISM: Artificial Sequence
<220> FEATURE:
<223> OTHER INFORMATION: Melanoma differentiation antigen

<400> SEQUENCE: 154

```
Glu Ala Ala Gly Ile Gly Ile Leu Thr Val
1               5                  10
```

<210> SEQ ID NO 155
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 155

```
Ile Leu Thr Val Ile Leu Gly Val Leu
1               5
```

<210> SEQ ID NO 156
<211> LENGTH: 10
<212> TYPE: PRT
<213> ORGANISM: Artificial Sequence
<220> FEATURE:
<223> OTHER INFORMATION: Melanoma differentiation antigen

<400> SEQUENCE: 156

```
Glu Ala Ala Gly Ile Gly Ile Leu Thr Val
1               5                  10
```

```
<210> SEQ ID NO 157
<211> LENGTH: 10
<212> TYPE: PRT
<213> ORGANISM: Artificial Sequence
<220> FEATURE:
<223> OTHER INFORMATION: Melanoma differentiation antigen

<400> SEQUENCE: 157

Ala Glu Glu Ala Ala Gly Ile Gly Ile Leu
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Melanoma differentiation antigen

<400> SEQUENCE: 158

Arg Asn Gly Tyr Arg Ala Leu Met Asp Lys Ser
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Melanoma differentiation antigen

<400> SEQUENCE: 159

Glu Glu Ala Ala Gly Ile Gly Ile Leu Thr Val Ile
1               5                   10

<210> SEQ ID NO 160
<211> LENGTH: 14
<212> TYPE: PRT
<213> ORGANISM: Artificial Sequence
<220> FEATURE:
<223> OTHER INFORMATION: Melanoma differentiation antigen

<400> SEQUENCE: 160

Ala Ala Gly Ile Gly Ile Leu Thr Val Ile Leu Gly Val Leu
1               5                   10

<210> SEQ ID NO 161
<211> LENGTH: 13
<212> TYPE: PRT
<213> ORGANISM: Artificial Sequence
<220> FEATURE:
<223> OTHER INFORMATION: Melanoma differentiation antigen

<400> SEQUENCE: 161

Ala Pro Pro Ala Tyr Glu Lys Leu Pro Ser Ala Glu Gln
1               5                   10

<210> SEQ ID NO 162
<211> LENGTH: 23
<212> TYPE: PRT
<213> ORGANISM: Artificial Sequence
<220> FEATURE:
<223> OTHER INFORMATION: Melanoma differentiation antigen

<400> SEQUENCE: 162

Arg Asn Gly Tyr Arg Ala Leu Met Asp Lys Ser Leu His Val Gly Thr
1               5                   10                  15
```

Gln Cys Ala Leu Thr Arg Arg
            20

<210> SEQ ID NO 163
<211> LENGTH: 20
<212> TYPE: PRT
<213> ORGANISM: Artificial Sequence
<220> FEATURE:
<223> OTHER INFORMATION: Melanoma differentiation antigen

<400> SEQUENCE: 163

Met Pro Arg Glu Asp Ala His Phe Ile Tyr Gly Tyr Pro Lys Lys Gly
1               5                   10                  15

His Gly His Ser
            20

<210> SEQ ID NO 164
<211> LENGTH: 20
<212> TYPE: PRT
<213> ORGANISM: Artificial Sequence
<220> FEATURE:
<223> OTHER INFORMATION: Melanoma differentiation antigen

<400> SEQUENCE: 164

Lys Asn Cys Glu Pro Val Val Pro Asn Ala Pro Pro Ala Tyr Glu Lys
1               5                   10                  15

Leu Ser Ala Glu
            20

<210> SEQ ID NO 165
<211> LENGTH: 9
<212> TYPE: PRT
<213> ORGANISM: Artificial Sequence
<220> FEATURE:
<223> OTHER INFORMATION: Prostate carcinoma differentiation antigen

<400> SEQUENCE: 165

Phe Leu Phe Leu Leu Phe Phe Trp Leu
1               5

<210> SEQ ID NO 166
<211> LENGTH: 9
<212> TYPE: PRT
<213> ORGANISM: Artificial Sequence
<220> FEATURE:
<223> OTHER INFORMATION: Prostate carcinoma differentiation antigen

<400> SEQUENCE: 166

Thr Leu Met Ser Ala Met Thr Asn Leu
1               5

<210> SEQ ID NO 167
<211> LENGTH: 9
<212> TYPE: PRT
<213> ORGANISM: Artificial Sequence
<220> FEATURE:
<223> OTHER INFORMATION: Prostate carcinoma differentiation antigen

<400> SEQUENCE: 167

Ala Leu Asp Val Tyr Asn Gly Leu Leu
1               5

<210> SEQ ID NO 168
<211> LENGTH: 10
<212> TYPE: PRT
<213> ORGANISM: Artificial Sequence

```
<220> FEATURE:
<223> OTHER INFORMATION: Prostate carcinoma differentiation antigen

<400> SEQUENCE: 168

Phe Leu Thr Pro Lys Lys Leu Gln Cys Val
1               5                   10

<210> SEQ ID NO 169
<211> LENGTH: 10
<212> TYPE: PRT
<213> ORGANISM: Artificial Sequence
<220> FEATURE:
<223> OTHER INFORMATION: Prostate carcinoma differentiation antigen

<400> SEQUENCE: 169

Val Ile Ser Asn Asp Val Cys Ala Gln Val
1               5                   10

<210> SEQ ID NO 170
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 170

Met Ser Leu Gln Arg Gln Phe Leu Arg
1               5

<210> SEQ ID NO 171
<211> LENGTH: 21
<212> TYPE: PRT
<213> ORGANISM: Artificial Sequence
<220> FEATURE:
<223> OTHER INFORMATION: Melanoma differentiation antigen

<400> SEQUENCE: 171

Ile Ser Pro Asn Ser Val Phe Ser Gln Trp Arg Val Val Cys Asp Ser
1               5                   10                  15

Leu Glu Asp Tyr Asp
            20

<210> SEQ ID NO 172
<211> LENGTH: 10
<212> TYPE: PRT
<213> ORGANISM: Artificial Sequence
<220> FEATURE:
<223> OTHER INFORMATION: Melanoma differentiation antigen

<400> SEQUENCE: 172

Ser Leu Pro Tyr Trp Asn Phe Ala Thr Gly
1               5                   10

<210> SEQ ID NO 173
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 173

Ser Val Tyr Asp Phe Phe Val Trp Leu
1               5

<210> SEQ ID NO 174
<211> LENGTH: 9
```

```
<212> TYPE: PRT
<213> ORGANISM: Artificial Sequence
<220> FEATURE:
<223> OTHER INFORMATION: Melanoma differentiation antigen

<400> SEQUENCE: 174

Thr Leu Asp Ser Gln Val Met Ser Leu
1               5

<210> SEQ ID NO 175
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 175

Leu Leu Gly Pro Gly Arg Pro Tyr Arg
1               5

<210> SEQ ID NO 176
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 176

Ala Asn Asp Pro Ile Phe Val Val Leu
1               5

<210> SEQ ID NO 177
<211> LENGTH: 15
<212> TYPE: PRT
<213> ORGANISM: Artificial Sequence
<220> FEATURE:
<223> OTHER INFORMATION: Melanoma differentiation antigen

<400> SEQUENCE: 177

Gln Cys Thr Glu Val Arg Ala Asp Thr Arg Pro Trp Ser Gly Pro
1               5                   10                  15

<210> SEQ ID NO 178
<211> LENGTH: 10
<212> TYPE: PRT
<213> ORGANISM: Artificial Sequence
<220> FEATURE:
<223> OTHER INFORMATION: Melanoma differentiation antigen

<400> SEQUENCE: 178

Ala Leu Pro Tyr Trp Asn Phe Ala Thr Gly
1               5                   10

<210> SEQ ID NO 179
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 179

Lys Cys Asp Ile Cys Thr Asp Glu Tyr
1               5

<210> SEQ ID NO 180
<211> LENGTH: 11
<212> TYPE: PRT
```

-continued

```
<213> ORGANISM: Artificial Sequence
<220> FEATURE:
<223> OTHER INFORMATION: Melanoma differentiation antigen

<400> SEQUENCE: 180

Ser Ser Asp Tyr Val Ile Pro Ile Gly Thr Tyr
1               5                   10

<210> SEQ ID NO 181
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 181

Met Leu Leu Ala Val Leu Tyr Cys Leu
1               5

<210> SEQ ID NO 182
<211> LENGTH: 10
<212> TYPE: PRT
<213> ORGANISM: Artificial Sequence
<220> FEATURE:
<223> OTHER INFORMATION: Melanoma differentiation antigen

<400> SEQUENCE: 182

Cys Leu Leu Trp Ser Phe Gln Thr Ser Ala
1               5                   10

<210> SEQ ID NO 183
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 183

Tyr Met Asp Gly Thr Met Ser Gln Val
1               5

<210> SEQ ID NO 184
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 184

Ala Phe Leu Pro Trp His Arg Leu Phe
1               5

<210> SEQ ID NO 185
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 185

Gln Cys Ser Gly Asn Phe Met Gly Phe
1               5

<210> SEQ ID NO 186
<211> LENGTH: 12
<212> TYPE: PRT
<213> ORGANISM: Artificial Sequence
```

```
<220> FEATURE:
<223> OTHER INFORMATION: Melanoma differentiation antigen

<400> SEQUENCE: 186

Thr Pro Arg Leu Pro Ser Ser Ala Asp Val Glu Phe
1               5                   10

<210> SEQ ID NO 187
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 187

Leu Pro Ser Ser Ala Asp Val Glu Phe
1               5

<210> SEQ ID NO 188
<211> LENGTH: 10
<212> TYPE: PRT
<213> ORGANISM: Artificial Sequence
<220> FEATURE:
<223> OTHER INFORMATION: Melanoma differentiation antigen

<400> SEQUENCE: 188

Leu His His Ala Phe Val Asp Ser Ile Phe
1               5                   10

<210> SEQ ID NO 189
<211> LENGTH: 9
<212> TYPE: PRT
<213> ORGANISM: Artificial Sequence
<220> FEATURE:
<223> OTHER INFORMATION: Melanoma differentiation antigen

<400> SEQUENCE: 189

Ser Glu Ile Trp Arg Asp Ile Asp Phe
1               5

<210> SEQ ID NO 190
<211> LENGTH: 15
<212> TYPE: PRT
<213> ORGANISM: Artificial Sequence
<220> FEATURE:
<223> OTHER INFORMATION: Melanoma differentiation antigen

<400> SEQUENCE: 190

Gln Asn Ile Leu Leu Ser Asn Ala Pro Leu Gly Pro Gln Phe Pro
1               5                   10                  15

<210> SEQ ID NO 191
<211> LENGTH: 13
<212> TYPE: PRT
<213> ORGANISM: Artificial Sequence
<220> FEATURE:
<223> OTHER INFORMATION: Melanoma differentiation antigen

<400> SEQUENCE: 191

Ser Tyr Leu Gln Asp Ser Asp Pro Asp Ser Phe Gln Asp
1               5                   10

<210> SEQ ID NO 192
<211> LENGTH: 21
<212> TYPE: PRT
<213> ORGANISM: Artificial Sequence
<220> FEATURE:
```

<223> OTHER INFORMATION: Melanoma differentiationt antigen

<400> SEQUENCE: 192

Phe Leu Leu His His Ala Phe Val Asp Ser Ile Phe Glu Gln Trp Leu
1               5                   10                  15
Gln Arg His Arg Pro
            20

<210> SEQ ID NO 193
<211> LENGTH: 9
<212> TYPE: PRT
<213> ORGANISM: Artificial Sequence
<220> FEATURE:
<223> OTHER INFORMATION: Ubiquitous (low level) overexpressed antigen

<400> SEQUENCE: 193

Phe Met Val Glu Asp Glu Thr Val Leu
1               5

<210> SEQ ID NO 194
<211> LENGTH: 10
<212> TYPE: PRT
<213> ORGANISM: Artificial Sequence
<220> FEATURE:
<223> OTHER INFORMATION: Ubiquitous (low level) overexpressed antigen

<400> SEQUENCE: 194

Phe Ile Asn Asp Glu Ile Phe Val Glu Leu
1               5                   10

<210> SEQ ID NO 195
<211> LENGTH: 9
<212> TYPE: PRT
<213> ORGANISM: Artificial Sequence
<220> FEATURE:
<223> OTHER INFORMATION: Ubiquitous (low level) overexpressed antigen

<400> SEQUENCE: 195

Lys Tyr Asp Cys Phe Leu His Pro Phe
1               5

<210> SEQ ID NO 196
<211> LENGTH: 9
<212> TYPE: PRT
<213> ORGANISM: Artificial Sequence
<220> FEATURE:
<223> OTHER INFORMATION: Ubiquitous (low level) overexpressed antigen

<400> SEQUENCE: 196

Lys Tyr Val Gly Ile Glu Arg Glu Met
1               5

<210> SEQ ID NO 197
<211> LENGTH: 9
<212> TYPE: PRT
<213> ORGANISM: Artificial Sequence
<220> FEATURE:
<223> OTHER INFORMATION: Ubiquitous (low level) overexpressed antigen

<400> SEQUENCE: 197

Lys Ile Phe Gly Ser Leu Ala Phe Leu
1               5

<210> SEQ ID NO 198
<211> LENGTH: 9
<212> TYPE: PRT

<213> ORGANISM: Artificial Sequence
<220> FEATURE:
<223> OTHER INFORMATION: Ubiquitous (low level) overexpressed antigen

<400> SEQUENCE: 198

Ile Ile Ser Ala Val Val Gly Ile Leu
1               5

<210> SEQ ID NO 199
<211> LENGTH: 9
<212> TYPE: PRT
<213> ORGANISM: Artificial Sequence
<220> FEATURE:
<223> OTHER INFORMATION: Ubiquitous (low level) overexpressed antigen

<400> SEQUENCE: 199

Ala Leu Cys Arg Trp Gly Leu Leu Leu
1               5

<210> SEQ ID NO 200
<211> LENGTH: 9
<212> TYPE: PRT
<213> ORGANISM: Artificial Sequence
<220> FEATURE:
<223> OTHER INFORMATION: Ubiquitous (low level) overexpressed antigen

<400> SEQUENCE: 200

Ile Leu His Asn Gly Ala Tyr Ser Leu
1               5

<210> SEQ ID NO 201
<211> LENGTH: 9
<212> TYPE: PRT
<213> ORGANISM: Artificial Sequence
<220> FEATURE:
<223> OTHER INFORMATION: Ubiquitous (low level) overexpressed antigen

<400> SEQUENCE: 201

Arg Leu Leu Gln Glu Thr Glu Leu Val
1               5

<210> SEQ ID NO 202
<211> LENGTH: 9
<212> TYPE: PRT
<213> ORGANISM: Artificial Sequence
<220> FEATURE:
<223> OTHER INFORMATION: Ubiquitious (low level) overexpressed antigen

<400> SEQUENCE: 202

Val Val Leu Gly Val Val Phe Gly Ile
1               5

<210> SEQ ID NO 203
<211> LENGTH: 10
<212> TYPE: PRT
<213> ORGANISM: Artificial Sequence
<220> FEATURE:
<223> OTHER INFORMATION: Ubiquitous (low level) overexpressed antigen

<400> SEQUENCE: 203

Tyr Met Ile Met Val Lys Cys Trp Met Ile
1               5                   10

<210> SEQ ID NO 204
<211> LENGTH: 9
<212> TYPE: PRT
<213> ORGANISM: Artificial Sequence

```
<220> FEATURE:
<223> OTHER INFORMATION: Ubiquitous (low level) overexpressed antigen

<400> SEQUENCE: 204

His Leu Tyr Gln Gly Cys Gln Val Val
1               5

<210> SEQ ID NO 205
<211> LENGTH: 10
<212> TYPE: PRT
<213> ORGANISM: Artificial Sequence
<220> FEATURE:
<223> OTHER INFORMATION: Ubiquitous (low level) overexpressed antigen

<400> SEQUENCE: 205

Tyr Leu Val Pro Gln Gln Gly Phe Phe Cys
1               5                   10

<210> SEQ ID NO 206
<211> LENGTH: 9
<212> TYPE: PRT
<213> ORGANISM: Artificial Sequence
<220> FEATURE:
<223> OTHER INFORMATION: Ubiquitous (low level) overexpressed antigen

<400> SEQUENCE: 206

Pro Leu Gln Pro Glu Gln Leu Gln Val
1               5

<210> SEQ ID NO 207
<211> LENGTH: 9
<212> TYPE: PRT
<213> ORGANISM: Artificial Sequence
<220> FEATURE:
<223> OTHER INFORMATION: Ubiquitous (low level) overexpressed antigen

<400> SEQUENCE: 207

Thr Leu Glu Glu Ile Thr Gly Tyr Leu
1               5

<210> SEQ ID NO 208
<211> LENGTH: 9
<212> TYPE: PRT
<213> ORGANISM: Artificial Sequence
<220> FEATURE:
<223> OTHER INFORMATION: Ubiquitous (low level) overexpressed antigen

<400> SEQUENCE: 208

Ala Leu Ile His His Asn Thr His Leu
1               5

<210> SEQ ID NO 209
<211> LENGTH: 9
<212> TYPE: PRT
<213> ORGANISM: Artificial Sequence
<220> FEATURE:
<223> OTHER INFORMATION: Ubiquitous (low level) overexpressed antigen

<400> SEQUENCE: 209

Pro Leu Thr Ser Ile Ile Ser Ala Val
1               5

<210> SEQ ID NO 210
<211> LENGTH: 9
<212> TYPE: PRT
<213> ORGANISM: Artificial Sequence
<220> FEATURE:
```

```
<223> OTHER INFORMATION: Ubiquitous (low level) overexpressed antigen

<400> SEQUENCE: 210

Val Leu Arg Glu Asn Thr Ser Pro Lys
1               5

<210> SEQ ID NO 211
<211> LENGTH: 9
<212> TYPE: PRT
<213> ORGANISM: Artificial Sequence
<220> FEATURE:
<223> OTHER INFORMATION: Ubiquitous (low level) overexpressed antigen

<400> SEQUENCE: 211

Thr Tyr Leu Pro Thr Asn Ala Ser Leu
1               5

<210> SEQ ID NO 212
<211> LENGTH: 9
<212> TYPE: PRT
<213> ORGANISM: Artificial Sequence
<220> FEATURE:
<223> OTHER INFORMATION: Liver overexpressed antigen

<400> SEQUENCE: 212

Gly Val Ala Leu Gln Thr Met Lys Gln
1               5

<210> SEQ ID NO 213
<211> LENGTH: 9
<212> TYPE: PRT
<213> ORGANISM: Artificial Sequence
<220> FEATURE:
<223> OTHER INFORMATION: Liver overexpressed antigen

<400> SEQUENCE: 213

Phe Met Asn Lys Phe Ile Tyr Glu Ile
1               5

<210> SEQ ID NO 214
<211> LENGTH: 10
<212> TYPE: PRT
<213> ORGANISM: Artificial Sequence
<220> FEATURE:
<223> OTHER INFORMATION: Liver overexpressed antigen

<400> SEQUENCE: 214

Gln Leu Ala Val Ser Val Ile Leu Arg Val
1               5                   10

<210> SEQ ID NO 215
<211> LENGTH: 9
<212> TYPE: PRT
<213> ORGANISM: Artificial Sequence
<220> FEATURE:
<223> OTHER INFORMATION: Glandular epithelia overexpressed antigen

<400> SEQUENCE: 215

Ser Thr Ala Pro Pro Val His Asn Val
1               5

<210> SEQ ID NO 216
<211> LENGTH: 9
<212> TYPE: PRT
<213> ORGANISM: Artificial Sequence
<220> FEATURE:
<223> OTHER INFORMATION: Glandular epithelia overexpressed antigen
```

<400> SEQUENCE: 216

Leu Leu Leu Leu Thr Val Leu Thr Val
1               5

<210> SEQ ID NO 217
<211> LENGTH: 12
<212> TYPE: PRT
<213> ORGANISM: Artificial Sequence
<220> FEATURE:
<223> OTHER INFORMATION: Glandular epithelia overexpressed antigen

<400> SEQUENCE: 217

Pro Gly Ser Thr Ala Pro Pro Ala His Gly Val Thr
1               5                   10

<210> SEQ ID NO 218
<211> LENGTH: 9
<212> TYPE: PRT
<213> ORGANISM: Artificial Sequence
<220> FEATURE:
<223> OTHER INFORMATION: Ubiquitous (low level) overexpressed antigen

<400> SEQUENCE: 218

Leu Leu Gly Arg Asn Ser Phe Glu Val
1               5

<210> SEQ ID NO 219
<211> LENGTH: 9
<212> TYPE: PRT
<213> ORGANISM: Artificial Sequence
<220> FEATURE:
<223> OTHER INFORMATION: Ubiquitous (low level) overexpressed antigen

<400> SEQUENCE: 219

Arg Met Pro Glu Ala Ala Pro Pro Val
1               5

<210> SEQ ID NO 220
<211> LENGTH: 9
<212> TYPE: PRT
<213> ORGANISM: Artificial Sequence
<220> FEATURE:
<223> OTHER INFORMATION: Ubiquitous (low level) overexpressed antigen

<400> SEQUENCE: 220

Ser Gln Lys Thr Tyr Gln Gly Ser Tyr
1               5

<210> SEQ ID NO 221
<211> LENGTH: 13
<212> TYPE: PRT
<213> ORGANISM: Artificial Sequence
<220> FEATURE:
<223> OTHER INFORMATION: Ubiquitous (low level) overexpressed antigen

<400> SEQUENCE: 221

Pro Gly Thr Arg Val Arg Ala Met Ala Ile Tyr Lys Gln
1               5                   10

<210> SEQ ID NO 222
<211> LENGTH: 12
<212> TYPE: PRT
<213> ORGANISM: Artificial Sequence
<220> FEATURE:
<223> OTHER INFORMATION: Ubiquitous (low level) overexpressed antigen -continued

<400> SEQUENCE: 222

His Leu Ile Arg Val Glu Gly Asn Leu Arg Val Glu
1               5                   10

<210> SEQ ID NO 223
<211> LENGTH: 9
<212> TYPE: PRT
<213> ORGANISM: Artificial Sequence
<220> FEATURE:
<223> OTHER INFORMATION: Testis, ovary, endometrium, adrenals
      overexpressed antigen

<400> SEQUENCE: 223

Val Leu Asp Gly Leu Asp Val Leu Leu
1               5

<210> SEQ ID NO 224
<211> LENGTH: 10
<212> TYPE: PRT
<213> ORGANISM: Artificial Sequence
<220> FEATURE:
<223> OTHER INFORMATION: Testis, ovary, endometrium, adrenals
      overexpressed antigen

<400> SEQUENCE: 224

Ser Leu Tyr Ser Phe Pro Glu Pro Glu Ala
1               5                   10

<210> SEQ ID NO 225
<211> LENGTH: 10
<212> TYPE: PRT
<213> ORGANISM: Artificial Sequence
<220> FEATURE:
<223> OTHER INFORMATION: Testis, ovary, endometrium, adrenals
      overexpressed antigen

<400> SEQUENCE: 225

Ala Leu Tyr Val Asp Ser Leu Phe Phe Leu
1               5                   10

<210> SEQ ID NO 226
<211> LENGTH: 9
<212> TYPE: PRT
<213> ORGANISM: Artificial Sequence
<220> FEATURE:
<223> OTHER INFORMATION: Testis, ovary, endometrium, adrenals
      overexpressed antigen

<400> SEQUENCE: 226

Ser Leu Leu Gln His Leu Ile Gly Leu
1               5

<210> SEQ ID NO 227
<211> LENGTH: 9
<212> TYPE: PRT
<213> ORGANISM: Artificial Sequence
<220> FEATURE:
<223> OTHER INFORMATION: Testis, ovary, endometrium, adrenals
      overexpressed antigen

<400> SEQUENCE: 227

Leu Tyr Val Asp Ser Leu Phe Phe Leu
1               5

<210> SEQ ID NO 228
<211> LENGTH: 9
<212> TYPE: PRT

```
<213> ORGANISM: Artificial Sequence
<220> FEATURE:
<223> OTHER INFORMATION: Prostate, Central Nervous System, liver
      overexpressed antigen

<400> SEQUENCE: 228

Asn Tyr Ala Arg Thr Glu Asp Phe Phe
1               5

<210> SEQ ID NO 229
<211> LENGTH: 9
<212> TYPE: PRT
<213> ORGANISM: Artificial Sequence
<220> FEATURE:
<223> OTHER INFORMATION: retina overexpressed antigen

<400> SEQUENCE: 229

Leu Lys Leu Ser Gly Val Val Arg Leu
1               5

<210> SEQ ID NO 230
<211> LENGTH: 10
<212> TYPE: PRT
<213> ORGANISM: Artificial Sequence
<220> FEATURE:
<223> OTHER INFORMATION: retina overexpressed antigen

<400> SEQUENCE: 230

Pro Leu Pro Pro Ala Arg Asn Gly Gly Leu
1               5                   10

<210> SEQ ID NO 231
<211> LENGTH: 10
<212> TYPE: PRT
<213> ORGANISM: Artificial Sequence
<220> FEATURE:
<223> OTHER INFORMATION: retina overexpressed antigen

<400> SEQUENCE: 231

Ser Pro Ser Ser Asn Arg Ile Arg Asn Thr
1               5                   10

<210> SEQ ID NO 232
<211> LENGTH: 9
<212> TYPE: PRT
<213> ORGANISM: Artificial Sequence
<220> FEATURE:
<223> OTHER INFORMATION: heart, skeletal muscle, pericytes
      overexpressed antigen

<400> SEQUENCE: 232

Leu Ala Ala Leu Pro His Ser Cys Leu
1               5

<210> SEQ ID NO 233
<211> LENGTH: 10
<212> TYPE: PRT
<213> ORGANISM: Artificial Sequence
<220> FEATURE:
<223> OTHER INFORMATION: heart, skeletal muscle, pericytes
      overexpressed antigen

<400> SEQUENCE: 233

Gly Leu Ala Ser Phe Lys Ser Phe Leu Lys
1               5                   10

<210> SEQ ID NO 234
```

```
<211> LENGTH: 10
<212> TYPE: PRT
<213> ORGANISM: Artificial Sequence
<220> FEATURE:
<223> OTHER INFORMATION: heart, skeletal muscle, pericytes
      overexpressed antigen

<400> SEQUENCE: 234

Ala Leu Trp Pro Trp Leu Leu Met Ala Thr
1               5                   10

<210> SEQ ID NO 235
<211> LENGTH: 9
<212> TYPE: PRT
<213> ORGANISM: Artificial Sequence
<220> FEATURE:
<223> OTHER INFORMATION: heart, skeletal muscle, pericytes
      overexpressed antigen

<400> SEQUENCE: 235

Asn Ser Gln Pro Val Trp Leu Cys Leu
1               5

<210> SEQ ID NO 236
<211> LENGTH: 9
<212> TYPE: PRT
<213> ORGANISM: Artificial Sequence
<220> FEATURE:
<223> OTHER INFORMATION: Ubiquitous (low level) overexpressed antigen

<400> SEQUENCE: 236

Ala Trp Ile Ser Lys Pro Pro Gly Val
1               5

<210> SEQ ID NO 237
<211> LENGTH: 10
<212> TYPE: PRT
<213> ORGANISM: Artificial Sequence
<220> FEATURE:
<223> OTHER INFORMATION: Ubiquitous (low level) overexpressed antigen

<400> SEQUENCE: 237

Ser Ala Trp Ile Ser Lys Pro Pro Gly Val
1               5                   10

<210> SEQ ID NO 238
<211> LENGTH: 9
<212> TYPE: PRT
<213> ORGANISM: Artificial Sequence
<220> FEATURE:
<223> OTHER INFORMATION: prostate overexpressed antigen

<400> SEQUENCE: 238

Met Ile Ala Val Phe Leu Pro Ile Val
1               5

<210> SEQ ID NO 239
<211> LENGTH: 15
<212> TYPE: PRT
<213> ORGANISM: Artificial Sequence
<220> FEATURE:
<223> OTHER INFORMATION: Ubiquitous (low level) overexpressed antigen

<400> SEQUENCE: 239

His Gln Gln Tyr Phe Tyr Lys Ile Pro Ile Leu Val Ile Asn Lys
1               5                   10                  15
```

```
<210> SEQ ID NO 240
<211> LENGTH: 9
<212> TYPE: PRT
<213> ORGANISM: Artificial Sequence
<220> FEATURE:
<223> OTHER INFORMATION: testis, thymus, bone marrow, lymph nodes
      overexpressed antigen

<400> SEQUENCE: 240

Ile Leu Ala Lys Phe Leu His Trp Leu
1               5

<210> SEQ ID NO 241
<211> LENGTH: 9
<212> TYPE: PRT
<213> ORGANISM: Artificial Sequence
<220> FEATURE:
<223> OTHER INFORMATION: testis, thymus, bone marrow, lymph nodes
      overexpressed antigen

<400> SEQUENCE: 241

Arg Leu Val Asp Asp Phe Leu Leu Val
1               5

<210> SEQ ID NO 242
<211> LENGTH: 15
<212> TYPE: PRT
<213> ORGANISM: Artificial Sequence
<220> FEATURE:
<223> OTHER INFORMATION: testis, thymus, bone marrow, lymph nodes
      overexpressed antigen

<400> SEQUENCE: 242

Arg Pro Gly Leu Leu Gly Ala Ser Val Leu Gly Leu Asp Asp Ile
1               5                   10                  15

<210> SEQ ID NO 243
<211> LENGTH: 15
<212> TYPE: PRT
<213> ORGANISM: Artificial Sequence
<220> FEATURE:
<223> OTHER INFORMATION: testis, thymus, bone marrow, lymph nodes
      overexpressed antigen

<400> SEQUENCE: 243

Leu Thr Asp Leu Gln Pro Tyr Met Arg Gln Phe Val Ala His Leu
1               5                   10                  15

<210> SEQ ID NO 244
<211> LENGTH: 11
<212> TYPE: PRT
<213> ORGANISM: Artificial Sequence
<220> FEATURE:
<223> OTHER INFORMATION: testis, ovary, bone marrow, spleen
      overexpressed antigen

<400> SEQUENCE: 244

Thr Ser Glu Lys Arg Pro Phe Met Cys Ala Tyr
1               5                   10

<210> SEQ ID NO 245
<211> LENGTH: 9
<212> TYPE: PRT
<213> ORGANISM: Artificial Sequence
<220> FEATURE:
<223> OTHER INFORMATION: testis, ovary, bone marrow, spleen
      overexpressed antigen

<400> SEQUENCE: 245
```

```
Cys Met Thr Trp Asn Gln Met Asn Leu
1               5

<210> SEQ ID NO 246
<211> LENGTH: 11
<212> TYPE: PRT
<213> ORGANISM: Artificial Sequence
<220> FEATURE:
<223> OTHER INFORMATION: testis, ovary, bone marrow, spleen
      overexpressed antigen

<400> SEQUENCE: 246

Leu Ser His Leu Gln Met His Ser Arg Lys His
1               5                   10

<210> SEQ ID NO 247
<211> LENGTH: 16
<212> TYPE: PRT
<213> ORGANISM: Artificial Sequence
<220> FEATURE:
<223> OTHER INFORMATION: testis, ovary, bone marrow, spleen
      overexpressed antigen

<400> SEQUENCE: 247

Lys Arg Tyr Phe Lys Leu Ser His Leu Gln Met His Ser Arg Lys His
1               5                   10                  15

<210> SEQ ID NO 248
<211> LENGTH: 9
<212> TYPE: PRT
<213> ORGANISM: Artificial Sequence
<220> FEATURE:
<223> OTHER INFORMATION: Skin, lung, small intestine overexpressed
      antigen

<400> SEQUENCE: 248

Thr Leu Ala Asp Phe Asp Pro Arg Val
1               5

<210> SEQ ID NO 249
<211> LENGTH: 9
<212> TYPE: PRT
<213> ORGANISM: Artificial Sequence
<220> FEATURE:
<223> OTHER INFORMATION: Ubiquitous, low level overexpressed antigen

<400> SEQUENCE: 249

Thr Leu Ala Asp Phe Asp Pro Arg Val
1               5

<210> SEQ ID NO 250
<211> LENGTH: 10
<212> TYPE: PRT
<213> ORGANISM: Artificial Sequence
<220> FEATURE:
<223> OTHER INFORMATION: Reactive astrocytes, macrophages, chondrocytes,
      neutrophils synovial cells overexpressed antigen

<400> SEQUENCE: 250

Ser Ile Met Thr Tyr Asp Phe His Gly Ala
1               5                   10

<210> SEQ ID NO 251
<211> LENGTH: 11
<212> TYPE: PRT
<213> ORGANISM: Artificial Sequence
<220> FEATURE:
```

```
<223> OTHER INFORMATION: Ubiquitous (at mRNA level) overexpressed
      antigen

<400> SEQUENCE: 251

Ala Leu Ser Pro Ala Ser Ser Arg Ser Val
1               5                   10

<210> SEQ ID NO 252
<211> LENGTH: 9
<212> TYPE: PRT
<213> ORGANISM: Artificial Sequence
<220> FEATURE:
<223> OTHER INFORMATION: Ubiquitous, low level overexpressed antigen

<400> SEQUENCE: 252

Glu Tyr Arg Gly Phe Thr Gln Asp Phe
1               5

<210> SEQ ID NO 253
<211> LENGTH: 10
<212> TYPE: PRT
<213> ORGANISM: Artificial Sequence
<220> FEATURE:
<223> OTHER INFORMATION: Ubiquitous, low level overexpressed antigen

<400> SEQUENCE: 253

Val Tyr Asp Tyr Asn Cys His Val Asp Leu
1               5                   10

<210> SEQ ID NO 254
<211> LENGTH: 9
<212> TYPE: PRT
<213> ORGANISM: Artificial Sequence
<220> FEATURE:
<223> OTHER INFORMATION: Lung epithelial cells, fibroblasts
      overexpressed antigen

<400> SEQUENCE: 254

Ala Leu Pro Phe Gly Phe Ile Leu Val
1               5

<210> SEQ ID NO 255
<211> LENGTH: 9
<212> TYPE: PRT
<213> ORGANISM: Artificial Sequence
<220> FEATURE:
<223> OTHER INFORMATION: Lung, kidney, spleen overexpressed antigen

<400> SEQUENCE: 255

Thr Ile Met Ala Phe Arg Trp Val Thr
1               5

<210> SEQ ID NO 256
<211> LENGTH: 9
<212> TYPE: PRT
<213> ORGANISM: Artificial Sequence
<220> FEATURE:
<223> OTHER INFORMATION: Lassa Virus overexpressed antigen

<400> SEQUENCE: 256

Gly Leu Val Gly Leu Val Thr Phe Leu
1               5

<210> SEQ ID NO 257
<211> LENGTH: 9
<212> TYPE: PRT
<213> ORGANISM: Artificial Sequence
```

```
<220> FEATURE:
<223> OTHER INFORMATION: Lassa Virus overexpressed antigen

<400> SEQUENCE: 257

Ser Leu Tyr Lys Gly Val Tyr Glu Leu
1               5

<210> SEQ ID NO 258
<211> LENGTH: 9
<212> TYPE: PRT
<213> ORGANISM: Artificial Sequence
<220> FEATURE:
<223> OTHER INFORMATION: Lassa Virus overexpressed antigen

<400> SEQUENCE: 258

Tyr Leu Ile Ser Ile Phe Leu His Leu
1               5

<210> SEQ ID NO 259
<211> LENGTH: 15
<212> TYPE: PRT
<213> ORGANISM: Artificial Sequence
<220> FEATURE:
<223> OTHER INFORMATION: Lassa Virus overexpressed antigen

<400> SEQUENCE: 259

Asn Ser Phe Tyr Tyr Met Lys Gly Gly Val Asn Thr Phe Leu Ile
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: Lassa Virus overexpressed antigen

<400> SEQUENCE: 260

Ser Lys Thr His Leu Asn Phe Glu Arg Ser Leu Lys Ala Phe Phe
1               5                   10                  15

<210> SEQ ID NO 261
<211> LENGTH: 8
<212> TYPE: PRT
<213> ORGANISM: Artificial Sequence
<220> FEATURE:
<223> OTHER INFORMATION: Human Papillomavirus (HPV 16) overexpressed
      antigen

<400> SEQUENCE: 261

Thr Leu Gly Ile Val Glx Pro Ile
1               5

<210> SEQ ID NO 262
<211> LENGTH: 10
<212> TYPE: PRT
<213> ORGANISM: Artificial Sequence
<220> FEATURE:
<223> OTHER INFORMATION: Human Papillomavirus (HPV 16) overexpressed
      antigen

<400> SEQUENCE: 262

Tyr Met Leu Asp Leu Gln Pro Glu Thr Thr
1               5                   10

<210> SEQ ID NO 263
<211> LENGTH: 11
<212> TYPE: PRT
```

```
<213> ORGANISM: Artificial Sequence
<220> FEATURE:
<223> OTHER INFORMATION: Human Papillomavirus (HPV 16) overexpressed
      antigen

<400> SEQUENCE: 263

Cys Cys Lys Cys Asp Ser Thr Leu Arg Leu Cys
1               5                   10

<210> SEQ ID NO 264
<211> LENGTH: 8
<212> TYPE: PRT
<213> ORGANISM: Artificial Sequence
<220> FEATURE:
<223> OTHER INFORMATION: Mycobacterium tuberculosis overexpressed
      antigen

<400> SEQUENCE: 264

Ala Glu Met Lys Thr Asp Ala Ala
1               5

<210> SEQ ID NO 265
<211> LENGTH: 9
<212> TYPE: PRT
<213> ORGANISM: Artificial Sequence
<220> FEATURE:
<223> OTHER INFORMATION: Mycobacterium tuberculosis overexpressed
      antigen

<400> SEQUENCE: 265

Asn Ile Arg Gln Ala Gly Val Gln Tyr
1               5

<210> SEQ ID NO 266
<211> LENGTH: 25
<212> TYPE: PRT
<213> ORGANISM: Artificial Sequence
<220> FEATURE:
<223> OTHER INFORMATION: Mycobacterium tuberculosis overexpressed
      antigen

<400> SEQUENCE: 266

Met Lys Leu Thr Thr Met Ile Lys Thr Ala Val Ala Val Val Ala Met
1               5                   10                  15

Ala Ala Ile Ala Thr Phe Ala Ala Pro
            20                  25

<210> SEQ ID NO 267
<211> LENGTH: 11
<212> TYPE: PRT
<213> ORGANISM: Artificial Sequence
<220> FEATURE:
<223> OTHER INFORMATION: Mycobacterium tuberculosis overexpressed
      antigen

<400> SEQUENCE: 267

Lys Thr Ile Ala Tyr Asp Glu Glu Ala Arg Arg
1               5                   10

<210> SEQ ID NO 268
<211> LENGTH: 9
<212> TYPE: PRT
<213> ORGANISM: Artificial Sequence
<220> FEATURE:
<223> OTHER INFORMATION: Chlamydia trachomatis overexpressed antigen

<400> SEQUENCE: 268
```

```
Arg Leu Asn Met Phe Thr Pro Tyr Ile
1               5

<210> SEQ ID NO 269
<211> LENGTH: 21
<212> TYPE: PRT
<213> ORGANISM: Artificial Sequence
<220> FEATURE:
<223> OTHER INFORMATION: Clostridium tetani overexpressed antigen

<400> SEQUENCE: 269

Phe Asn Asn Phe Thr Val Ser Phe Trp Leu Arg Val Pro Lys Val Ser
1               5                   10                  15

Ala Ser His Leu Glu
            20

<210> SEQ ID NO 270
<211> LENGTH: 15
<212> TYPE: PRT
<213> ORGANISM: Artificial Sequence
<220> FEATURE:
<223> OTHER INFORMATION: Human Immunodeficiency Virus (HIV)
      overexpressed antigen

<400> SEQUENCE: 270

Thr Glu Lys Leu Trp Val Thr Val Tyr Tyr Gly Val Pro Val Trp
1               5                   10                  15

<210> SEQ ID NO 271
<211> LENGTH: 11
<212> TYPE: PRT
<213> ORGANISM: Artificial Sequence
<220> FEATURE:
<223> OTHER INFORMATION: Human Immunodeficiency Virus (HIV)
      overexpressed antigen

<400> SEQUENCE: 271

Lys Arg Gln Glu Ile Leu Asp Leu Trp Val Tyr
1               5                   10

<210> SEQ ID NO 272
<211> LENGTH: 10
<212> TYPE: PRT
<213> ORGANISM: Artificial Sequence
<220> FEATURE:
<223> OTHER INFORMATION: Human Immunodeficiency Virus (HIV)
      overexpressed antigen

<400> SEQUENCE: 272

Thr Ser Thr Leu Gln Glu Gln Ile Ala Trp
1               5                   10
```

MULTI-EPITOPIC VACCINE

CROSS-REFERENCE TO RELATED APPLICATION

This application claims the benefit of U.S. Provisional Patent Application 61/451,615, filed Mar. 11, 2011, the disclosure of which is hereby incorporated by reference in its entirety, including all figures, tables, amino acid sequences and polynucleotide sequences.

The Sequence Listing for this application is labeled "SeqList-replace.txt" which was created on May 25, 2014 and is 73 KB. The entire contents of the sequence listing is incorporated herein by reference in its entirety.

FIELD OF THE INVENTION

The present invention relates to a multi-epitopic vaccine and its use in immunotherapy including prevention and/or treatment of cancers or infectious diseases.

BACKGROUND OF THE INVENTION

Immunotherapy is gaining importance for the treatment and prevention of various human diseases, including infectious diseases and cancers.

Regarding immunotherapy in cancers, with the recent FDA approval of the Sipuleucel-T vaccine for prostate cancer, the feasibility of active immunization for the treatment of established cancer has been demonstrated.

It is now established that the immune system can recognize and to some extent eliminate tumor cells through different cells subsets including CD8 cytotoxic T lymphocytes (CTLs). Modulating the immune system in order to track and specifically destroy the tumor cells is a promising therapeutic approach (also called anti-tumoral immunotherapy) for treating patients.

Tumor-associated antigens recognized by CTLs are 8 to 11 residue peptides called $CD8^+$ epitopes which are bound to MHC class I molecules and displayed at the tumor cell surface. In the last decade, an increasing number of these peptides derived from the processing of tumor proteins have been identified and classified as tumor specific antigens (TSA) or tumor-associated antigens (TAAs). The main goal of current research on immunotherapy approaches is to elicit potent anti-tumor immunity after therapeutic vaccination against these antigens. Approaches widely developed and transferred to clinical trials include peptide vaccination and adoptive immunotherapy with ex-vivo loaded dendritic cells (DCs).

However, the clinical successes of these approaches have been modest. Among other reasons, this failure can be explained both by the very immunosuppressive properties of the tumor microenvironment and by the different immune escape mechanisms developed by the tumor cells including the loss of individual antigens.

Recently, the key role of another subset of T cells, called $CD4^+$ helper T cells (Th), has been described in anti-tumor immunity. Indeed, it has been reported that this CD4 compartment plays a crucial role in mounting an efficient anti-tumoral immune response (Bos and Sherman, 2010, *Cancer Res.* 70:8368-8377). As for CD8 T cells, Th cells are also involved in the maintenance of long-lasting cellular immunity (immunological memory), and tumor infiltration by Th cells is an essential step for the recruitment and function of CTLs.

Tumor-associated antigens recognized by Th cells are typically 12-25 residue peptides (although some are much longer) called $CD4^+$ epitopes which are bound to MHC class II molecules and displayed at the tumor cell surface.

The use of protein rather than peptides to induce anti-tumor immunity would allow multi-epitopic ($CD8^+$ and $CD4^+$ epitopes) antigen delivery to antigen presenting cells (APCs) such as dendritic cells (DCs). However, protein uptake by APCs is limited and frequently results in presentation of only CD4 epitopes by MHC class II molecules. This is because protein antigens taken up from the extracellular milieu do not efficiently enter the cytoplasm from where their constituent peptide epitopes can bind to MHC class I molecules being assembled in the endoplasmic reticulum (a process called cross-presentation). Therefore, there is a need to develop new approaches to increase the efficiency of protein uptake by DCs, and to facilitate presentation of both CD4 and CD8 epitopes.

Different vectors have been developed and evaluated to deliver different MHC class I restricted epitopes; these include viral vectors (Durantez et al., 2009, *Scand. J. Immunol* 69.80-89; Mateo et al., 1999, *J. Immunol.* 163:4058-4063; Tine et al., 2005, *Vaccine* 23:1085-1091), cDNA-based vaccine (Ishioka et al., 1999, *J. Immunol.* 162:3915-3925; Scardino et al, 2007, *Cancer Res.* 67:7028-7036) and mRNA electroporated dendritic cells (Waeckerle-Men et al., 2006, *Cancer Immunol. Immunother.* 55:1524-1533).

In addition to minimizing immune escape, targeting multiple epitopes allows a greater proportion of tumor cells in a heterogeneous tumor (i.e. different individual tumor cells expressing different antigens within same tumor) to be attacked. Some progress has been made for vaccinia virus vectors encoding multiple epitopes associated with infectious diseases (Thomson et al., 1996, *J. Immunol.* 157:822-826; Thomson et al., 1995, *Proc. Natl. Acad. Sci. USA.* 92:5845-5849; Anton et al., 1997, *J. Immunol.* 158:2535-2542). However, several limitations have been noted. The first is that vaccinia virus vectors encoded antigens are preferentially presented by MHC class I restricted molecules; second, there is a limitation of the size of insert; third, there is rapid degradation of the encoded antigens, and finally there are many regulatory hurdles for clinical translation.

An alternative approach that has several inherent advantages is a multi-epitope vaccine based on protein rather than on a viral or DNA based vaccine. This offers the major advantage of long-lasting MHC presentation of the cargo antigens to T lymphocytes (van Montfoort et al., 2009, *Proc. Natl. Acad. Sci. USA.* 106:6730-6735), but low immunogenicity of the vector—allowing for multiple vaccinations.

In the past decade, protein transduction domains (PTDs) are emerging as promising vectors to deliver different therapeutic targets, including proteins. PTDs are peptide sequences facilitating efficient protein translocation across biological membranes, independently of transporters or specific receptors. PTDs also offer the advantage of cost-efficient production. Since the discovery 20 years ago of the membrane translocating property of human immunodeficiency virus transactivating regulatory protein (HIV TAT), several PTDs have been identified including penetratin (Antennapedia homeodomain), VP22 (Herpes simplex virus) and the synthetic polyarginine (polyR). Different cargoes have been linked to PTD with the perspective of novel vaccine design. These include tumor-associated antigen for cancer immunotherapy.

The most widely studied PTD, TAT, was fused to different antigens and used to transduce dendritic cells (in virtually all studies) before testing immunogenicity in vivo (Brooks et al., 2010, *Biochimica et Biophysica Acta* 1805:25-34). In all these studies, a CTL-mediated immune response (i.e. mediated by CD8 T cells and restricted by MHC class I) was demonstrated after loading the DCs with the TAT-fusion protein, in contrast to the protein alone, and in some cases, CD4 T cells were also implicated. Moreover, vaccination with TAT fused to TRP2 resulted in long-term protection as shown in tumor-free mice re-challenged with the tumor, suggesting a superior memory response. However, there are several potential drawbacks concerning TAT. The first is that the use of TAT based vaccines directly in vivo without prior transduction of DCs remains largely unexplored. The second is that the nature of the cargo transported into the cell by TAT influences intracellular localisation; large TAT-fusion proteins can remain entrapped in endosomes where they are degraded, which is predicted to limit access to the cross-presentation pathway resulting in poor stimulation of CD8 T cells (Tünnemann et al., 2006, FASEB J., 20: 1775-1784).

Therefore, there is still a need for developing anti-tumor and anti-pathogen vaccines able to induce strong and broad T-cell responses specific for multiple epitopes of a given antigen, involving both CD4$^+$ and CD8$^+$ cells, preferably applicable to a broad range of patients, and that have the potential for direct injection into patients, without requiring DCs. The present invention solves this problem by providing a PTD fusion protein allowing efficient delivery and presentation of multiple CD4$^+$- and CD8$^+$-restricted epitopes. The multi-epitopic PTD fusion protein of the invention, thus, is useful in immunotherapy for treating and/or preventing cancers or infectious diseases.

SUMMARY OF THE INVENTION

A first aspect of the invention provides an isolated polypeptide comprising:
(i) a protein transduction domain consisting of ZEBRA or a fragment thereof that retains the capacity of internalization,
(ii) at least one CD4$^+$ epitope; and
(iii) at least one CD8$^+$ epitope.

A second aspect of the invention provides an isolated polynucleotide encoding a polypeptide of the invention, a recombinant vector comprising said polynucleotide, as well as a host cell comprising said recombinant vector.

A third aspect of the invention provides antigen presenting cells loaded with a polypeptide of the invention.

A fourth aspect of the invention provides a vaccine composition comprising a polypeptide of the invention or antigen presenting cells of the invention, for preventing, treating, or stabilizing cancers or infectious diseases.

A fifth aspect of the invention provides a use of a polypeptide of the invention or the use of antigen presenting cells loaded with a polypeptide of the invention in the manufacture of a medicament.

A sixth aspect of the invention provides a method of preventing, treating or stabilizing a cancer or an infectious disease in a subject said method comprising administering in a subject in need thereof a therapeutically effective amount of a polypeptide of the invention or antigen presenting cells of the invention, and at least one pharmaceutically acceptable carrier.

A seventh aspect of the invention provides a method for eliciting or improving, in a subject, an immunologic response against multiple epitopes that is dependent on CD4$^+$ helper T cells and CD8$^+$ cytotoxic T cells, wherein said method comprises administering either a polypeptide of the invention or antigen presenting cells of the invention to said subject.

An eighth aspect of the invention provides a method for eliciting or improving, in a subject, an immunologic response against multiple epitopes that is restricted by multiple MHC class I molecules and multiple MHC class II molecules, wherein said method comprises administering either a polypeptide of the invention or antigen presenting cells of the invention to said subject.

Construct 1: ZEBRA-β-lactamase: encodes β-lactamase from *E. Coli* deleted for the secretion signal (residues 1-23) and residue 24 His was changed to Asp to create an optimal Kozak sequence.

Construct 2: ZEBRA-OVA: encodes a truncated form of the chicken ovalbumin ($OVA_{234-386}$). This construction contains both CD8 epitope $OVA_{257-264}$ and CD4 epitope $OVA_{323-339}$.

Construct 3: ZEBRA-MultiE: encodes a chimeric protein with three CD8 epitopes from the ovalbumin $OVA_{257-264}$, from lymphocytic choriomengitis virus glycoprotein $LCMV\text{-}GP_{33-41}$ and from the murine tumor-associated antigen $GP100_{25-33}$ and two CD4 epitopes: $OVA_{323-339}$ and $LCMV\text{-}GP_{61-80}$. The spacers between each epitope are the natural flanking 4 amino acid residues.

Figure 2:
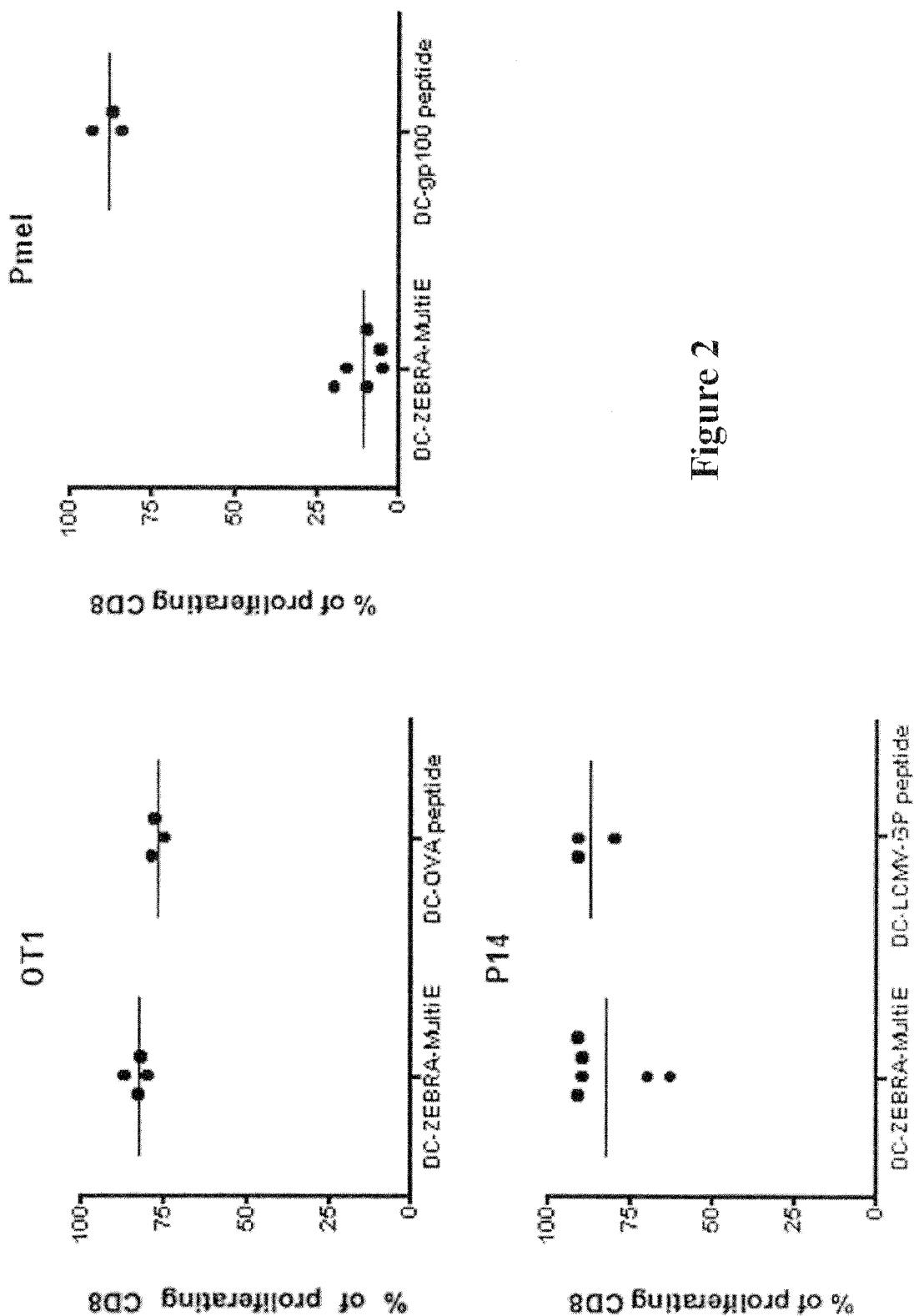

FIG. 2 shows CD8$^+$ multi-epitopic presentation after ZEBRA-multiE fusion protein loading into DCs.

Bone marrow dendritic cells from C57BL/6 mice were loaded with 0.3 μM ZEBRA-MultiE during 4 h and matured overnight with a cocktail containing IFNα, IFNγ, IL-4 and PolyIC. CFSE stained CD8 T cells from either OT-1, Pmel or P14 mice were added at a ratio 10:1. After 5 days of proliferation, dilution of CFSE was monitored by flow cytometry.

Figure 3:
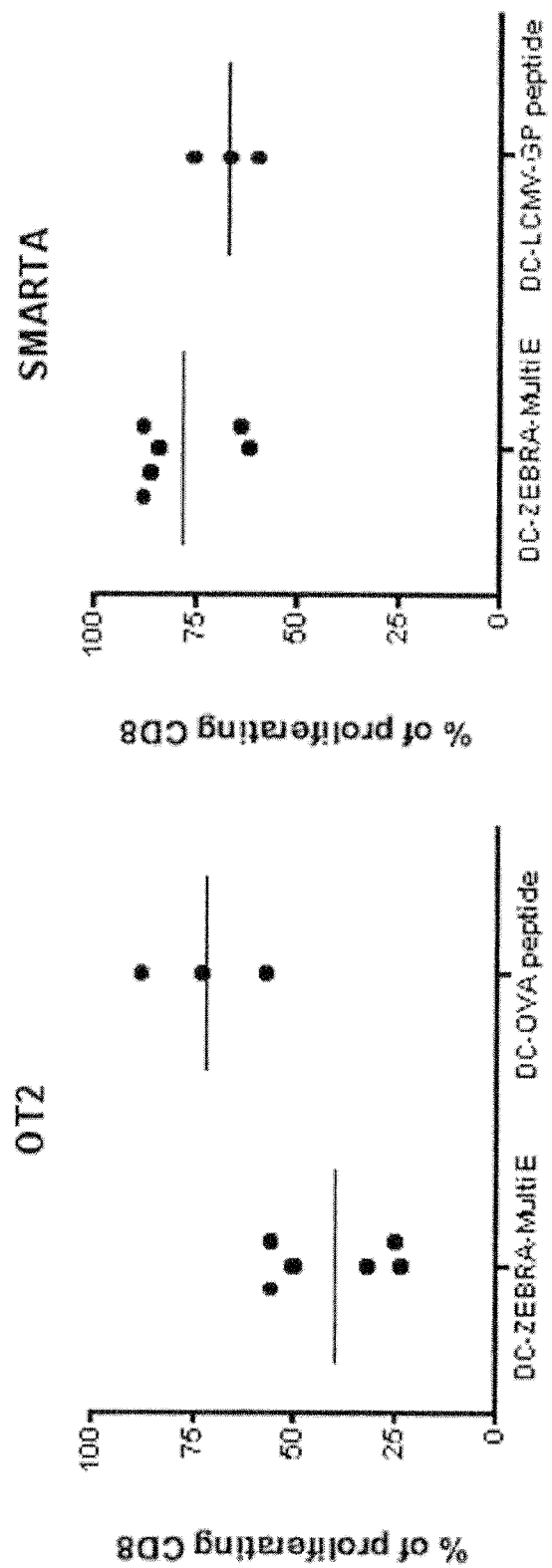

FIG. 3 shows CD4$^+$ multi-epitopic presentation after ZEBRA-multiE fusion protein loading into DCs.

Bone marrow dendritic cells from C57BL/6 mice were loaded with 0.3 μM ZEBRA-MultiE during 4 h and matured overnight with a cocktail containing IFNα, IFNγ, IL-4 and PolyIC. CFSE stained CD4 T cells from either OT-2 or SMARTA mice were added at a ratio 10:1. After 5 days of proliferation, dilution of CFSE was monitored by flow cytometry.

Figure 4:
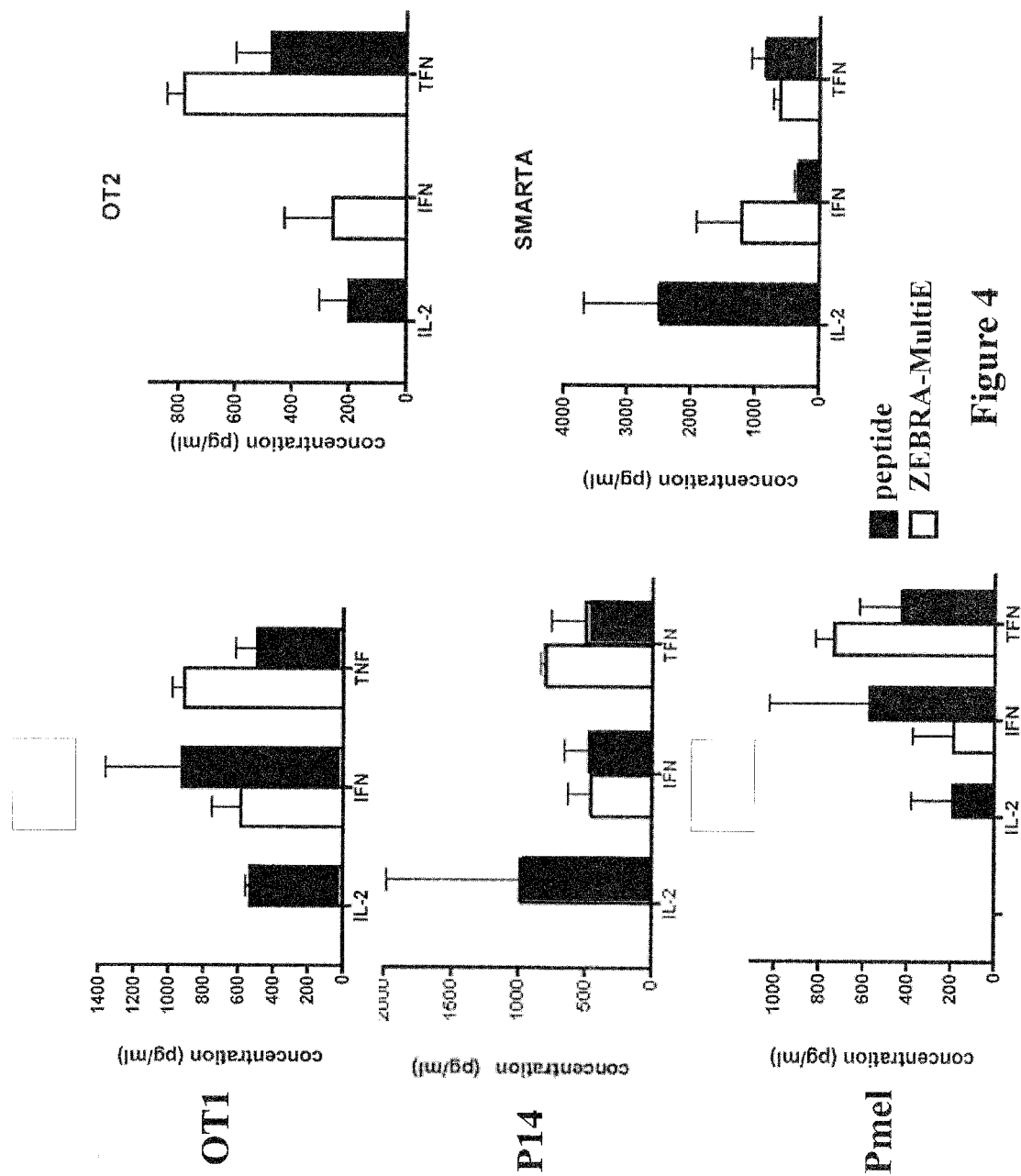

FIG. 4 shows effector function of T cells primed in vitro by DCs loaded with ZEBRA-MultiE fusion protein.

Bone marrow dendritic cells from C57BL/6 mice were loaded with 0.3 μM ZEBRA-MultiE during 4 h and matured overnight with a cocktail containing IFNα, IFNγ, IL-4 and PolyIC. CFSE stained CD8 T cells from either OT-1, Pmel or P14 mice and CD4 T cells from either OT-2 or SMARTA mice were added at a ratio 10:1. After 5 days of proliferation, the supernatant was tested for cytokine expression using the Multiplex cytokine detection kits (BD Biosciences Pharmingen, San Diego, Calif.) and analyzed by flow cytometry.

Figure 5:
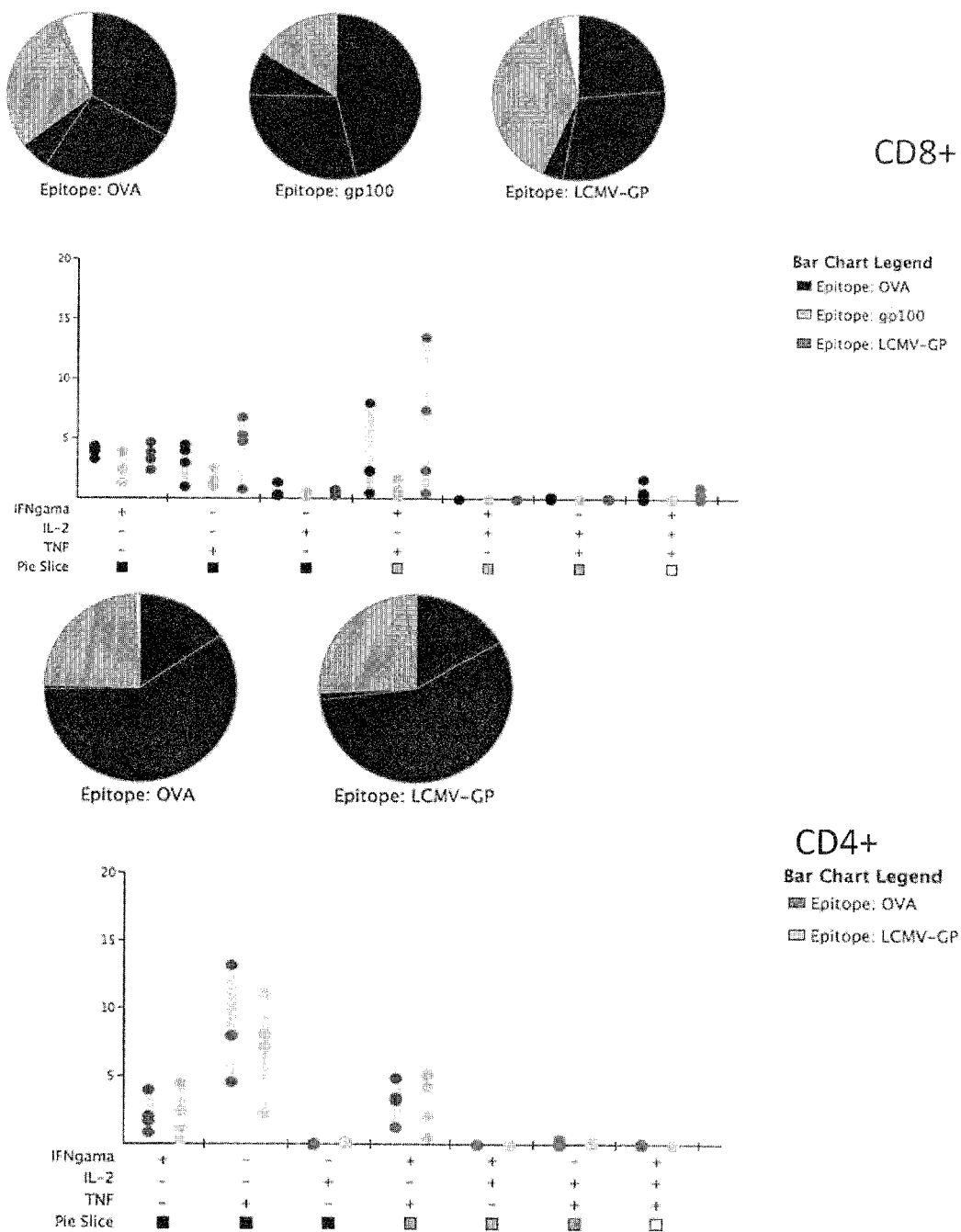

FIG. 5 shows the results of vaccination of mice with DCs loaded with ZEBRA-MultiE fusion protein.

C57BL/6 mice were vaccinated subcutaneously twice with a 14 days of interval with 1×10$^6$ mature dendritic cells loaded with ZEBRA-MultiE. 7 days after the last vaccination, splenocytes were recovered and re-stimulated during 7 days with 10 of the respective peptides. The T cells were re-stimulated with 10 μM of the respective peptide during 4 h and intracellular staining for IFNγ, TNFα and IL-2 was performed and analyzed by flow cytometry. Multi-functional analysis was performed with SPICE (Roeder et al, 2011, *Cytometry*, 79A: 167-174). The figures show the percentage of positive cells gated on CD8+ or CD4+ T cells, respectively.

Figure 6:
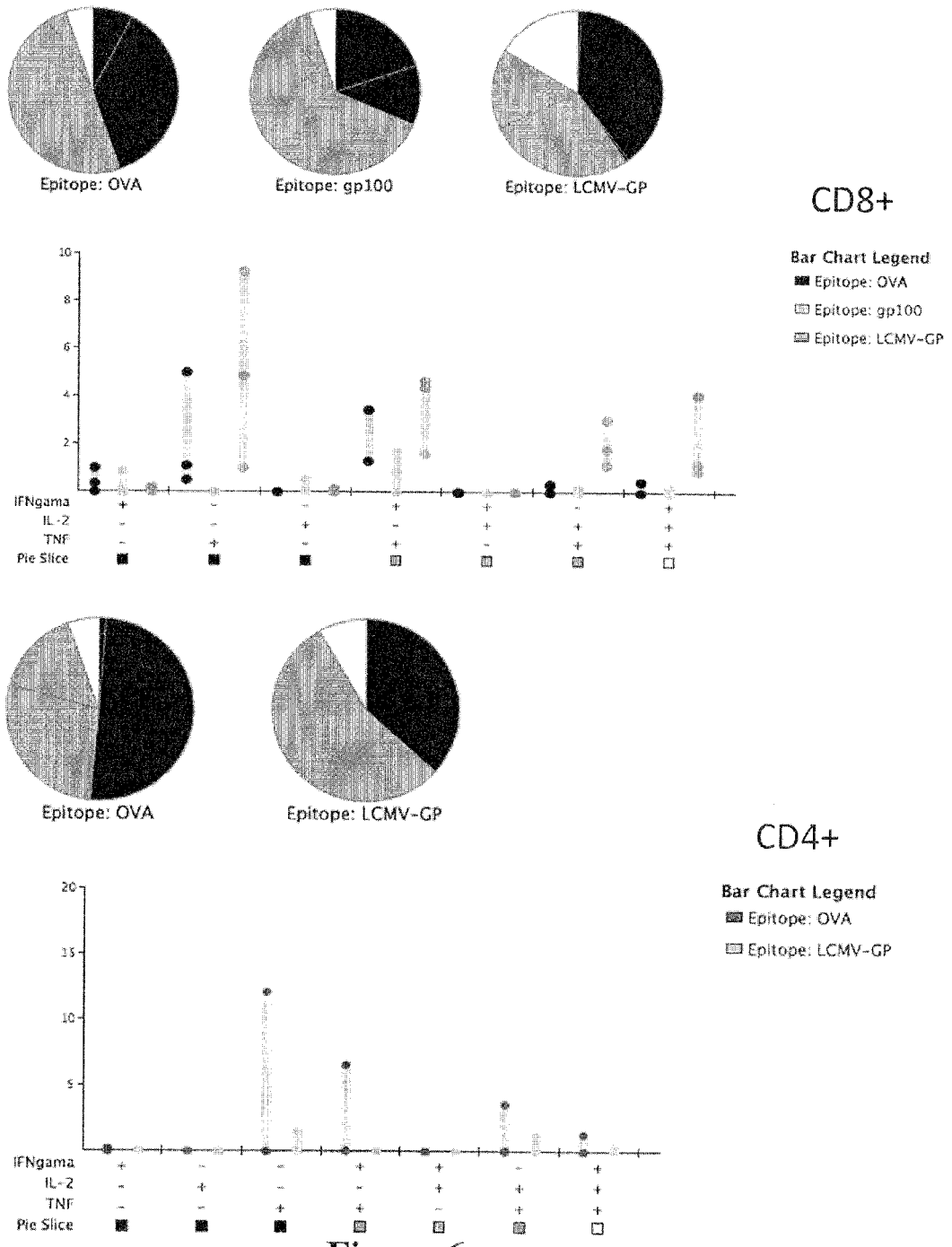

FIG. 6 shows the results of vaccination of mice with ZEBRA-MultiE fusion protein.

C57BL/6 mice were vaccinated subcutaneously twice with a 14 days of interval with 2×6 µg ZEBRA-MultiE and 100 µg PolyIC. 7 days after the last vaccination, splenocytes were recovered and re-stimulated during 7 days with 10 µM of the respective peptides. The T cells were re-stimulated with 10 µM of the respective peptide during 4 h and intracellular staining for IFNγ, TNFα and IL-2 was performed and analyzed by flow cytometry. Multi-functional analysis was performed with SPICE.

Figure 7:
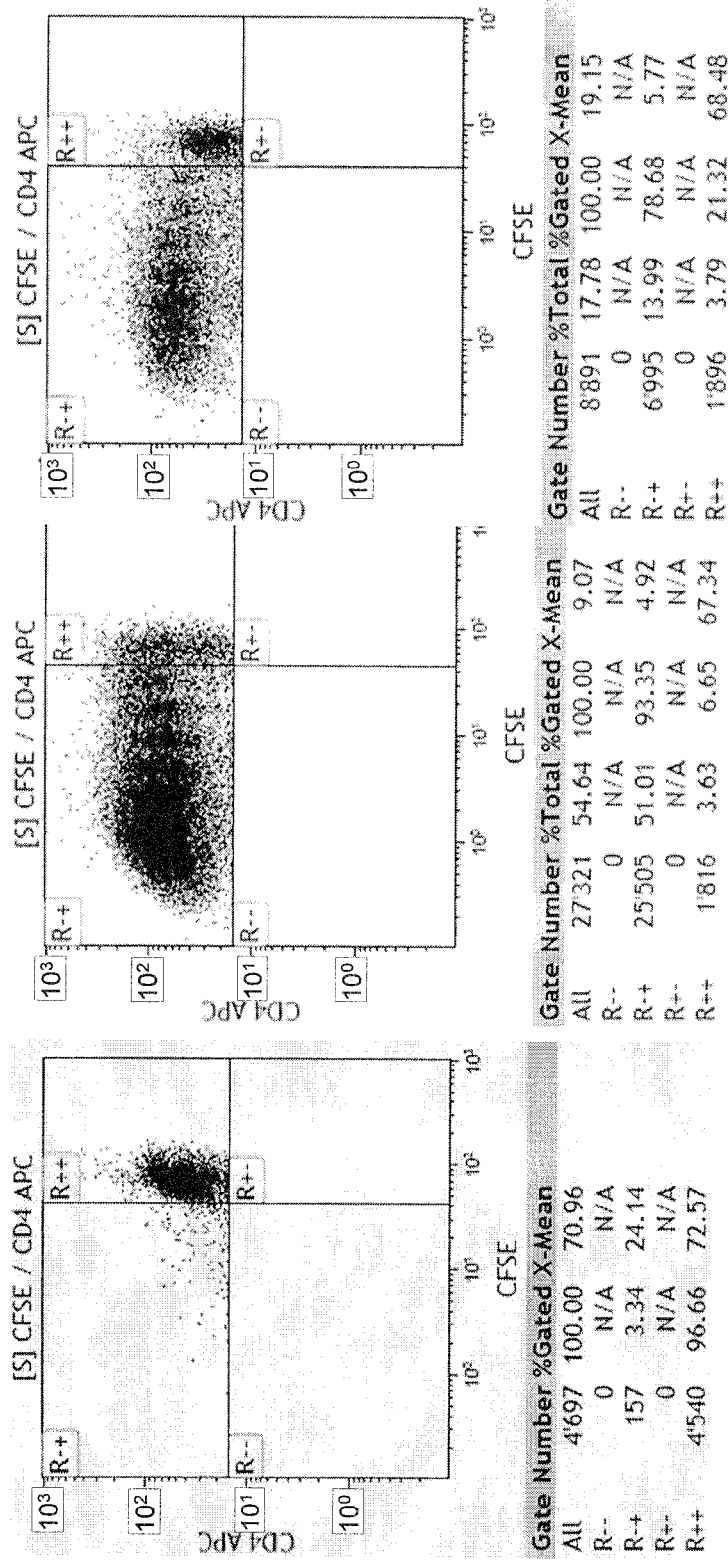

FIG. 7 shows that Zebra-MultiE can be processed and presented by dendritic cells with different MHC molecules.

Bone marrow derived dendritic cells from mice on BALB/c background were loaded for 4 h with 0.3 µM Zebra-MultiE and matured overnight with poly ICLC (Hiltonol®). Zebra-MultiE loaded and matured dendritic cells were co-incubated with CFSE stained splenocytes from DO11.10 TCR transgenic mice in which all of the CD4+ T cells are specific for the immunodominant ovalbumin epitope $OVA_{257-264}$. Negative control: splenocytes were incubated with non-loaded dendritic cells. Positive control: dendritic cells were pulsed with peptide. After five days of culture, T cell proliferation by CFSE dilution was monitored by flow cytometry.

Figure 8:
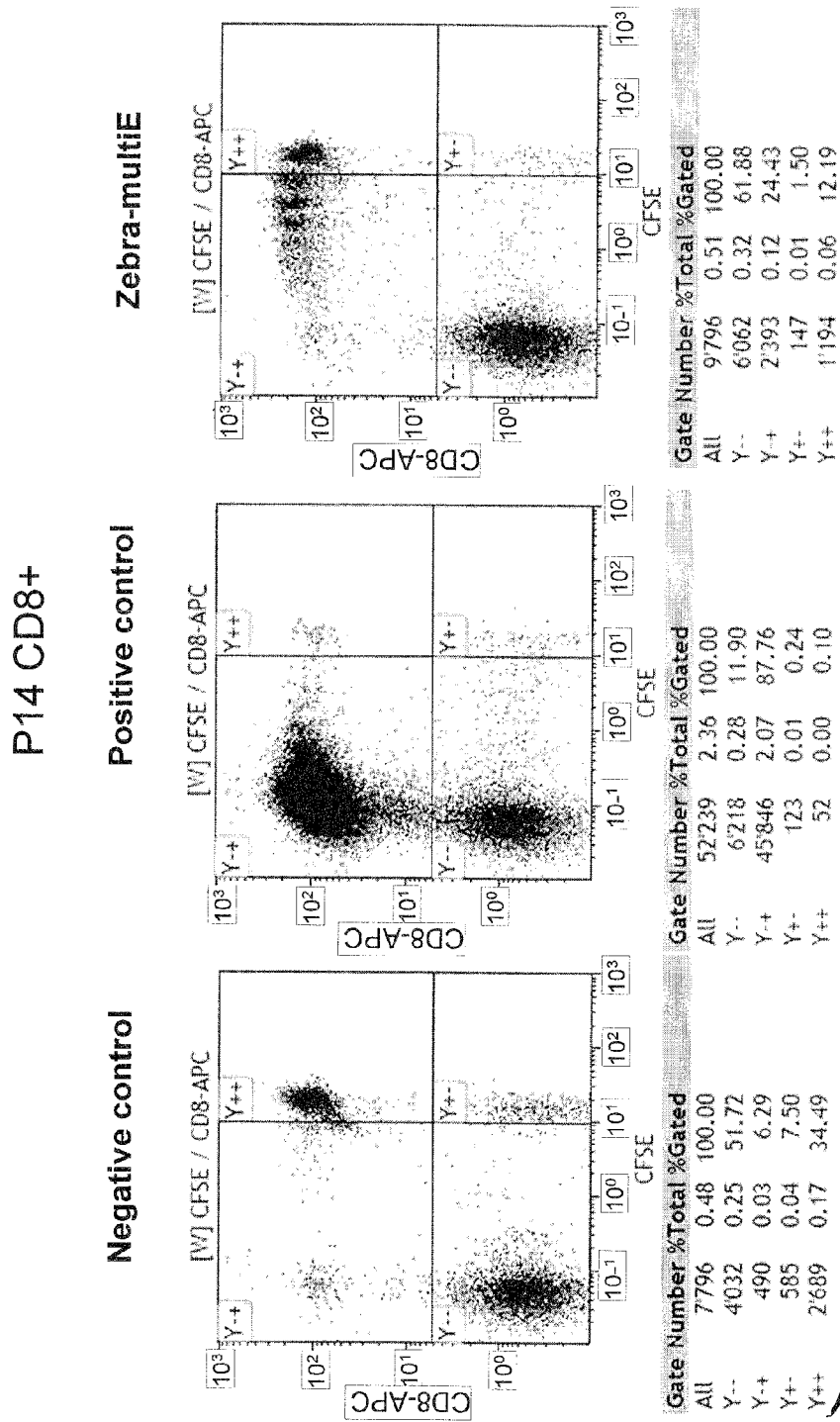
Figure 8:
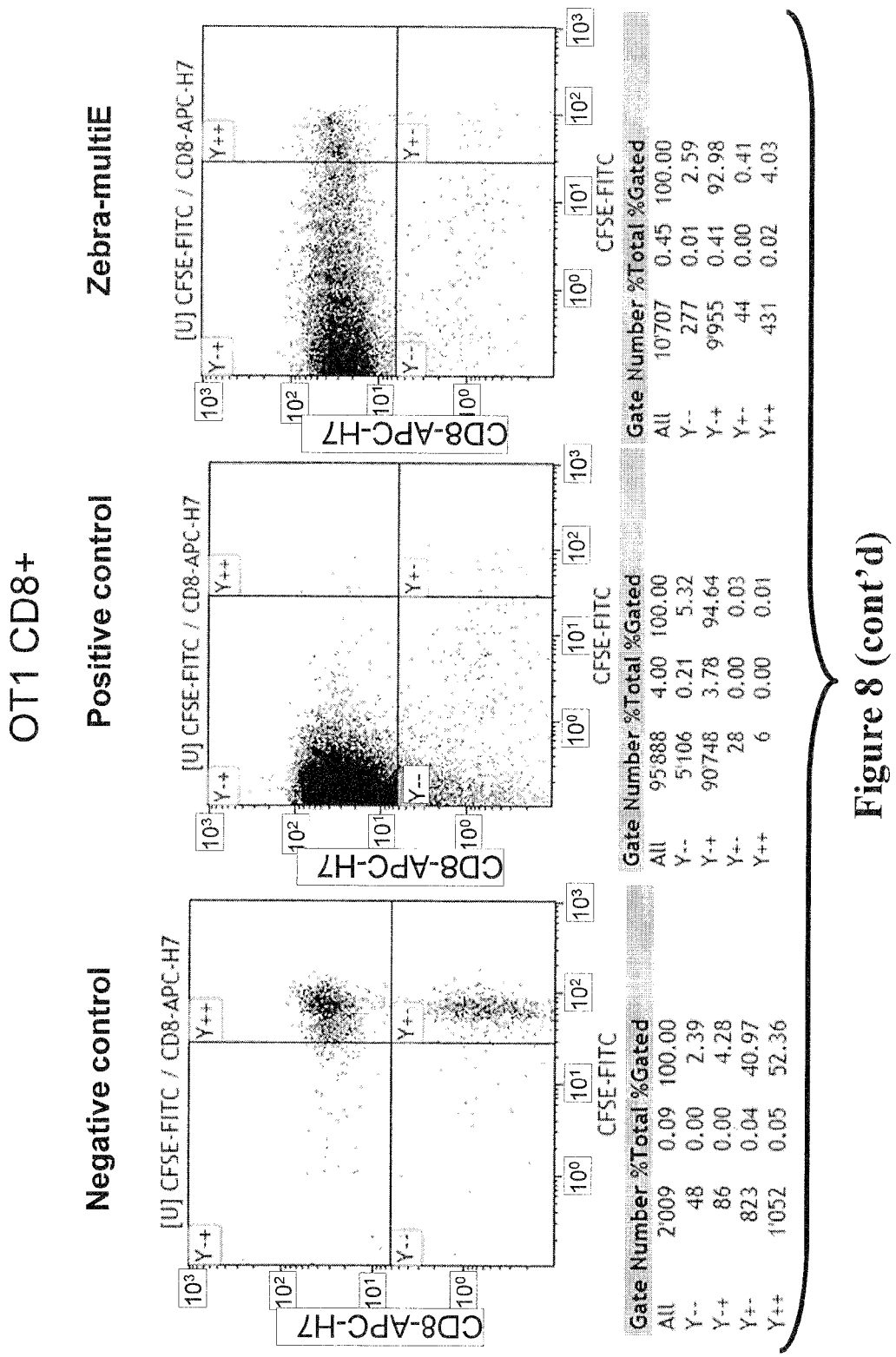

FIG. 8 shows that Zebra-MultiE translocates into endogenous dendritic cells in vivo, is processed leading to cross-presentation on MHC class I molecules.

C57BL/6 mice were vaccinated with PBS (negative control), 200 µg peptides and 100 µg anti-CD40 subcutaneously and 50 µg Poly ICLC (Hiltonol®) intramuscularly (positive control) or 10 µg ZEBRA-MultiE protein and 100 µg anti-CD40 subcutaneously and 50 µg Poly ICLC (Hiltonol®) intramuscularly. The same day, 1.5×10⁶ CFSE stained splenocytes from either P14 or OT1 TCR transgenic mice were adoptively transferred by intravenous injection. Four days after vaccination/adoptive transfer, the mice were sacrificed and proliferation of adoptively transferred T cell from draining lymph nodes was assessed by CFSE dilution.

Figure 9:
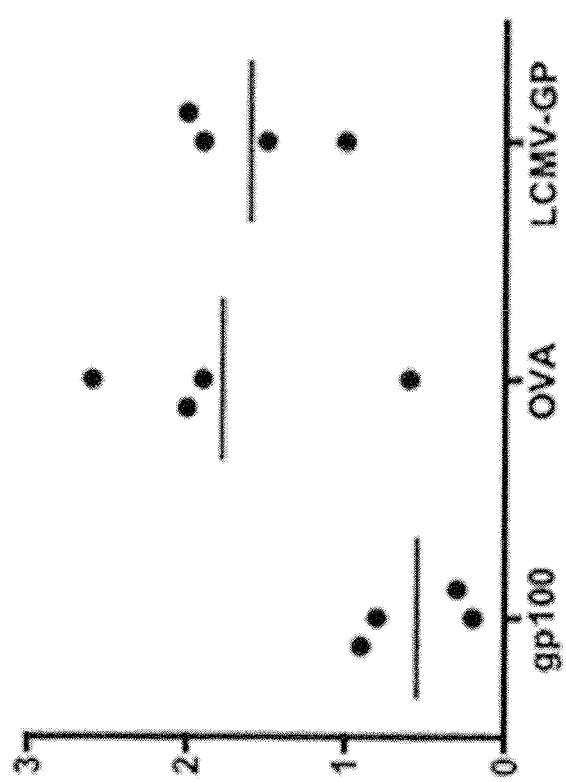

FIG. 9 shows that vaccination of mouse with ZEBRA-MultiE can induce polyclonal immune responses.

C57BL/6 mice were vaccinated twice at 14-days of interval by subcutaneous injection of 10 µg ZEBRA-MultiE protein and 100 µg anti-CD40 and intramuscular injection of 50 µg Poly ICLC (Hiltonol®). Seven days after the boost, the mice were sacrificed and the percentages of CD8+ T cells specific for either $OVA_{323-339}$, $LCMV-GP_{33-41}$, or $GP100_{25-33}$ were assessed in the draining lymph nodes by tetramer staining.

DETAILED DESCRIPTION OF THE INVENTION

The term "ZEBRA" (also known as Zta, Z, EB1, or BZLF1) generally means the basic-leucine zipper (bZIP) transcriptional activator of the Epstein-Barr virus (EBV). It also includes, herewith, a truncated form thereof retaining the capacity for internalization, such as the minimal domain (MD) currently known as spanning from residue 170 to residue 220 of ZEBRA (Rothe et al., 2010, *J. Biol. Chem.* 285: 20224-20233), as well as any fragment of the minimal domain mentioned above such as a fragment comprising or consisting of amino acid sequence SEQ ID NO: 8, or any peptide with a similar amino acid sequence as ZEBRA or ZEBRA fragment, provided said fragment or similar peptide still retains the capacity of internalization. The amino acid sequence of ZEBRA is disclosed under NCBI accession number YP_401673.

The term "epitope", also known as "antigenic determinant", is the part of an antigen that is recognized by the immune system, specifically by antibodies, B cells, or T cells. In the present application, the term "epitope" is mainly used to designate T cell epitopes, which are presented on the surface of an antigen-presenting cell, where they are bound to Major Histocompatibility Complex (MHC). T cell epitopes presented by MHC class I molecules are typically, but not exclusively, peptides between 8 and 11 amino acids in length, whereas MHC class II molecules present longer peptides, generally, but not exclusively, between 12 and 25 amino acids in length.

The term "CD4+ epitope" or "CD4+-restricted epitope" designates, herewith, an epitope recognized by a CD4+ T cell, said epitope consisting of an antigen fragment lying in the groove of a MHC class II molecule.

"CD8+ epitope" or "CD8+-restricted epitope" designates, herewith, an epitope recognized by a CD8+ T cell, said epitope consisting of an antigen fragment lying in the groove of a MHC class I molecule.

"MHC class I" designates one of the two primary classes of the Major Histocompatibility Complex molecules. The MHC class I (also noted "MHC I") molecules are found on every nucleated cell of the body. The function of MHC class I is to display an epitope to cytotoxic cells (CTLs). In humans, MHC class I molecules consist of two polypeptide chains, α- and β2-microglobulin (b2m). Only the α chain is polymorphic and encoded by a HLA gene, while the b2m subunit is not polymorphic and encoded by the Beta-2 microglobulin gene.

"MHC class II" designates the other primary class of the Major Histocompatibility Complex molecules. The MHC class II (also noted "MHC II") molecules are found only on a few specialized cell types, including macrophages, dendritic cells and B cells, all of which are professional antigen-presenting cells (APCs).

"Tumor epitope" means, herewith, an epitope from a tumor-associated antigen or from a tumor-specific antigen. Examples of tumor-associated and tumor-specific epitopes are provided in Tables 1-4.

"Pathogen epitope" means, herewith, an epitope from an antigenic protein from a pathogen including viruses, bacteria, fungi, protozoa and multicellular parasites. Antigenic proteins from pathogens include, herewith, proteins from pathogens responsible of diseases which can be a target for vaccination including, for instance, Amoebiasis, Anthrax, Buruli Ulcer (*Mycobacterium ulcerans*), Caliciviruses associated diarrhoea, *Campylobacter* diarrhoea, Cervical Cancer (Human papillomavirus), *Chlamydia trachomatis* associated genital diseases, Cholera, Crimean-Congo haemorrhagic fever, Dengue Fever, Diphtheria, Ebola haemorrhagic fever, Enterotoxigenic *Escherichia coli* (ETEC) diarrhoea, Gastric Cancer (*Helicobacter pylori*), Gonorrhea, Group A *Streptococcus* associated diseases, Group B *Streptococcus* associated diseases, *Haemophilus influenzae* B pneumonia and invasive disease, Hepatitis A, Hepatitis B, Hepatitis C, Hepatitis E diarrhoea, Herpes simplex type 2 genital ulcers, HIV/AIDS, Hookworm Disease, Influenza, Japanese encephalitis, Lassa Fever, Leishmaniasis, Leptospirosi, Liver cancer (Hepatitis B), Liver Cancer (Hepatitis C), Lyme Disease, Malaria, Marburg haemorrhagic fever, Measles, Mumps, Nasopharyngeal cancer (Epstein-Barr virus), *Neisseria meningitidis* Meningitis, Parainfluenza associated pneumonia, Pertussis, Plague, Poliomyelitis, Rabies, Respiratory syncytial virus (RSV) pneumonia, Rift Valley fever, Rotavirus diarrhoea, Rubella, Schistosomiasis, Severe Acute Respiratory Syndrome (SARS), Shigellosis, Smallpox, *Staphylococcus aureus* associated diseases, Stomach Cancer (*Helicobacter pylori*), *Streptococcus pneumoniae* and invasive disease, Tetanus, Tick-borne encephalitis, Trachoma, Tuberculosis, Tularaemia, Typhoid fever, West-Nile virus associated disease, Yellow fever.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it such as a preventive early asymptomatic intervention; (b) inhibiting the disease, i.e., arresting its development; or relieving the disease, i.e., causing regression of the disease and/or its symptoms or conditions such as improvement or remediation of damage. In particular, the methods, uses, formulations and compositions according to the invention are useful in the treatment of cancers or infectious diseases and/or in the prevention of evolution of cancers into an advanced or metastatic stage in patients with early stage cancer, thereby improving the staging of the cancer.

When applied to cancers, prevention of a disease or disorder includes the prevention of the appearance or development of a cancer in an individual identified as at risk of developing said cancer, for instance due to past occurrence of said cancer in the circle of the individual's relatives, and prevention of infection with tumor promoting pathogens such as, for example, Epstein-Barr virus (EBV), Human papillomavirus (HPV), Hepatitis B virus (HBV), Hepatitis C virus (HCV), Human Herpes virus 8 (HHV8), human T-cell leukemia virus type 1 (HTLV-1), Merkel cell polyomavirus (MCV) and *Helicobacter pylori*.

Also covered by the terms "prevention/treatment" of a cancer is the stabilization of an already diagnosed cancer in an individual. By "stabilization", it is meant the prevention of evolution of cancer into advanced or metastatic stage in patients with early stage cancer.

The term "subject" as used herein refers to mammals. For examples, mammals contemplated by the present invention include human, primates, domesticated animals such as cattle, sheep, pigs, horses, laboratory rodents and the like.

The term "effective amount" as used herein refers to an amount of at least one polypeptide, cells loaded with said polypeptide, composition or pharmaceutical formulation thereof according to the invention, that elicits the biological or medicinal response in a tissue, system, animal or human that is being sought. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active polypeptide sufficient to reduce the progression of the disease, notably to reduce or inhibit the tumor growth or infection and thereby elicit the response being sought (i.e. an "inhibition effective amount").

The term "efficacy" of a treatment according to the invention can be measured based on changes in the course of disease in response to a use or a method according to the invention. For example, the efficacy of a treatment of cancer can be measured by a reduction of tumor volume, and/or an increase of progression free survival time, and/or a decreased risk of relapse post-resection for primary cancer. More specifically for cancer treated by immunotherapy, assessment of efficacy can be by the spectrum of clinical patterns of antitumor response for immunotherapeutic agents through novel immune-related response criteria (irRC), which are adapted from Response Evaluation Criteria in Solid Tumors (RECIST) and World Health Organization (WHO) criteria (*J. Natl. Cancer Inst.* 2010, 102(18): 1388-1397). The efficacy of prevention of infectious disease is ultimately assessed by epidemiological studies in human populations, which often correlates with titres of neutralizing antibodies in sera, and induction of multifunctional pathogen specific T cell responses. Preclinical assessment can include resistance to infection after challenge with infectious pathogen. Treatment of an infectious disease can be measured by inhibition of the pathogen's growth or elimination of the pathogen (and, thus, absence of detection of the pathogen), correlating with pathogen specific antibodies and/or T cell immune responses.

The term "pharmaceutical formulation" refers to preparations which are in such a form as to permit biological activity of the active ingredient(s) to be unequivocally effective and which contain no additional component which would be toxic to subjects to which the said formulation would be administered.

Polypeptides According to the Invention

In a first embodiment, it is provided an isolated polypeptide comprising:
(i) a protein transduction domain consisting of ZEBRA or a fragment thereof that retains the capacity of internalization,
(ii) at least one, preferably at least two, CD4$^+$ epitope(s); and
(iii) at least one, preferably at least two, CD8$^+$ epitope(s).

In the polypeptide according to the invention, "ZEBRA" covers the basic-leucine zipper (bZIP) transcriptional activator of the Epstein-Barr virus (EBV), as well as a truncated form thereof retaining the capacity of internalization, such as the ZEBRA fragment comprising or consisting of amino acid sequence SEQ ID NO: 8, or any peptide with an identical or similar amino acid sequence, provided said ZEBRA fragment or identical or similar peptide retains the capacity of internalization of the protein comprising it.

Internalization of the fusion protein of the invention comprising ZEBRA or ZEBRA fragment can be checked by standard methods known to one skilled in the art, including flow cytometry or fluorescence microscopy of live and fixed cells, immunocytochemistry of cells transduced with said fusion protein, and Western blot.

In a preferred aspect, the polypeptide of the invention comprises a ZEBRA fragment comprising or consisting of SEQ ID NO: 8 or any peptide having at least 80%, at least 90%, at least 95%, at least 96%, at least 97%, at least 98%, or at least 99% identity with SEQ ID NO: 8.

The percentage of identity between two amino acid sequences or two nucleic acid sequences can be determined by visual inspection and/or mathematical calculation, or more easily by comparing sequence information using a computer program such as Clustal package version 1.83.

Therefore, according to one aspect of the invention, the ZEBRA protein or fragment thereof that is comprised in the polypeptide of the invention comprises an amino acid sequence having at least one conservatively substituted amino acid from the native sequence, meaning that a given amino acid residue is replaced by a residue having similar physiochemical characteristics. Generally, substitutions for one or more amino acids present in the native amino acid sequence should be made conservatively. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity properties, are well known (Kyte and Doolittle, 1982, *J. Mol. Biol.* 157(1): 105-132).

The CD4$^+$ epitope(s) comprised in the polypeptide of the invention correspond(s) to antigenic determinant(s) of a tumor-associated antigen, a tumor-specific antigen, or an antigenic protein from a pathogen. The CD4$^+$ epitopes comprised in the polypeptide of the invention generally, and preferably, consist of about 12-25 amino acids. They can also consist of about 8-25 amino acids or about 6-100 amino acids.

The CD8$^+$ epitope(s) comprised in the polypeptide of the invention correspond(s) to antigenic determinant(s) of an antigen such as a tumor-associated antigen, a tumor-specific antigen, or an antigenic protein from a pathogen. The CD8$^+$ epitopes comprised in the polypeptide of the invention generally, and preferably, consist of about 8-11 amino acids. They may also consist of about 8-15 amino acids or about 6-100 amino acids.

It will be clear for one skilled in the art that each of the epitopes comprised in the polypeptide of the invention can be either directly linked to each other or linked via spacers consisting of a few amino acids present between two successive epitopes.

In a specific aspect of the invention, two successive epitopes comprised in the polypeptide of the invention are linked to each other by spacers consisting of the natural flanking regions of said epitopes. Preferably, the spacer used to link a first epitope to a second epitope consists of about 8 amino acids corresponding to about 4 amino acids of the flanking region of the first epitope, followed by about 4 amino acids of the flanking region of the second epitope.

In a particular aspect of the invention, the CD4$^+$ and CD8$^+$ epitopes are antigenic determinants from a tumor-associated antigen or a tumor-specific antigen.

Exemplary tumor-associated antigens may be selected from the group of Melan A, MART-1, melanoma antigen family (MAGE-A1, MAGE-A2, MAGE-A3, MAGE-A4, MAGE-A6, MAGE-A9, MAGE-A10, MAGE-A12, MAGE-C1, MAGE-C2), cancer/testis antigen family (LAGE-1, LAGE2), synovial sarcoma X breakpoint 2 (SSX-2), synovial sarcoma X breakpoint 4 (SSX-4), Transient axonal glycoprotein family (TAG-1, TAG-2, TAG-72), Taxol-resistant-associated gene 3 (TRAG-3), gp100, gp75, v-erb-b2 erythroblastic leukemia viral oncogene homolog 2/glioblastoma oncogene homolog (HER-2/neu), prostate specific antigen (PSA), mucin 1 (MUC-1), mucin 16 (CA-125), tumor protein p53, mammaglobin-A, acid phosphatase prostate (PAP), tyrosine-related protein 2 (TRP-2), tyrosinase, kallikrein 4, carcinoembryonic antigen-related cell adhesion molecule 5 (CEA), preferentially expressed antigen in melanoma (PRAME), hydrolase prostate-specific membrane antigen 1 (PSMA), renal tumor antigen (RAGE-1), regulator of G-protein signaling 5 (RGS5), ring finger protein 43 (RNF43), sex determining region Y-box 10 (SOX-10), six transmembrane epithelial antigen of the prostate 1 (STEAP1), Wils tumor 1 (WT1), B melanoma antigen (BAGE-1), G antigen family (GAGE 1, 2, 8, 3, 4, 5, 6, 7), mannosyl (alpha-1,6-)-glycoprotein beta-1,6-N-acetyl-glucosaminyltransferase (GnTV), sarcoma antigen 1 (SAGE), sperm autoantigenic protein 17 (SP17), dopachrome tautomerase (TRP2), X antigen family, member 1B (XAGE-1b), KK-LC-1, KM-HN-1, ankyrin repeat domain 30A (NY-BR-1), G protein-coupled receptor 143 (OA1), RAB38 member RAS oncogene family, cyclin D1, vascular endothelial growth factor A (VEGF), fibroblast growth factor 5 (FGF5), Stn, KSA (17-1A), RAS, EGF-R, GD2, GM2, GD3, Anti-Id, CD20, CD19, CD22, CD36, Aberrant class II, B1, CD25, or BPV, EPH receptor A2 (EphA2), IL-13 receptor α2 chain (IL13Rα2), chitinase 3-like 1 (CHI3L1,YKL40), ADP-Ribosylation factor 4-like (ARF4L), UDP-Gal:βGlcNAc β1,3-galactosyltransferase polypeptide 3 (GALT3), squamous cell carcinoma antigen recognized by T cells 1 (SART-1), squamous cell carcinoma antigen recognized by T cells 3 (SART-3), Antigen isolated from immunoselected melanoma-2 (AIM-2), type III variant of the epidermal growth factor receptor EGFRvIII, Brevican (BCA), chitinase 3-like 2 (CHI), chondroitin sulfate proteoglycan 4, fatty acid binding protein 7, insulin-like growth factor 2 mRNA binding protein 3, neuroligin 4, X-linked, neuronal cell adhesion molecule, protein tyrosine phosphatase receptor-type, Z polypeptide 1, tenascin C, surviving, met proto-oncogene.

However, any epitope of any cancer- or tumor-associated antigen, as well as any epitope of any tumor-specific antigen, may be used.

Examples of tumor-associated antigens, tumor-specific antigens, and epitopes thereof, which can be comprised in the polypeptides of the invention are disclosed in Tables 1-4. This list is not limitative. Underlined are HLA alleles of MHC class II.

TABLE 1

"Tumor-specific antigens resulting from mutations": antigens that are unique to the tumor of an individual patient or restricted to very few patients

| Cancer | Antigen | HLA allele | Epitope | |
|---|---|---|---|---|
| chronic myeloid leukemia | breakpoint cluster region-c (BCR)-abl oncogene 1, (ABL) fusion protein (b3a2) | A2<br>B8<br>DR4<br>DR9 | SSKALQRPV<br>GFKQSSKAL<br>ATGFKQSSKALQRPVAS<br>ATGFKQSSKALQRPVAS | (SEQ ID NO: 9)<br>(SEQ ID NO: 10)<br>(SEQ ID NO: 11)<br>(SEQ ID NO: 11) |
| acute lymphoblastic leukemia | ets variant 6 (ETV6) runt-related transcription factor 1 (AML1) fusion protein | A2<br>DP5<br>DP17 | RIAECILGM<br>IGRIAECILGMNPSR<br>IGRIAECILGMNPSR | (SEQ ID NO: 12)<br>(SEQ ID NO: 13)<br>(SEQ ID NO: 13) |
| glioma | type III variant of the epidermal growth factor receptor EGFRvIII | A2 | LEEKKGNYV | (SEQ ID NO: 14) |

TABLE 2

"Shared tumor-specific antigens": Antigens that are shared between many tumors but not present in normal tissues

| Antigen | HLA allele | Epitope | |
|---|---|---|---|
| coiled-coil domain containing 110 (KM-HN-1) | A24 | NYNNFYRFL | (SEQ ID NO: 15) |
| | A24 | EYSKECLKEF | (SEQ ID NO: 16) |
| | A24 | EYLSLSDKI | (SEQ ID NO: 17) |
| cancer/testis antigen 2 (LAGE-1) | A2 | MLMAQEALAFL | (SEQ ID NO: 18) |
| | A2 | SLLMWITQC | (SEQ ID NO: 19) |
| | A31 | LAAQERRVPR | (SEQ ID NO: 20) |
| | A68 | ELVRRILSR | (SEQ ID NO: 21) |
| | B7 | APRGVRMAV | (SEQ ID NO: 22) |
| | DP4 | SLLMWITQCFLPVF | (SEQ ID NO: 23) |
| | DR3 | QGAMLAAQERRVPRAAEVPR | (SEQ ID NO: 24) |
| | DR4 | AADHRQLQLSISSCLQQL | (SEQ ID NO: 25) |
| | DR11 | CLSRRPWKRSWSAGSCPGMPHL | (SEQ ID NO: 26) |
| | DR12 | CLSRRPWKRSWSAGSCPGMPHL | (SEQ ID NO: 26) |
| | DR13 | ILSRDAAPLPRPG | (SEQ ID NO: 27) |
| | DR15 | AGATGGRGPRGAGA | (SEQ ID NO: 28) |
| melanoma antigen family A, 1 (MAGE-A1) | A1 | EADPTGHSY | (SEQ ID NO: 29) |
| | A2 | KVLEYVIKV | (SEQ ID NO: 30) |
| | A3 | SLFRAVITK | (SEQ ID NO: 31) |
| | A68 | EVDGREHSA | (SEQ ID NO: 32) |
| | B7 | RVRFFFPSL | (SEQ ID NO: 33) |
| | B35 | EADPTGHSY | (SEQ ID NO: 29) |
| | B37 | REPVTKAEML | (SEQ ID NO: 34) |
| | B53 | DPARYEFLW | (SEQ ID NO: 35) |
| | B57 | ITKKVADLVGF | (SEQ ID NO: 36) |
| | Cw2 | SAFPTTINF | (SEQ ID NO: 37) |
| | Cw3 | SAYGEPRKL | (SEQ ID NO: 38) |
| | Cw16 | SAYGEPRKL | (SEQ ID NO: 38) |
| | DP4 | TSCILESLFRAVITK | (SEQ ID NO: 39) |
| | DP4 | PRALAETSYVKVLEY | (SEQ ID NO: 40) |
| | DR13 | FLLLKYRAREPVTKAE | (SEQ ID NO: 41) |
| | DR15 | EYVIKVSARVRF | (SEQ ID NO: 42) |
| melanoma antigen family A, 2 (MAGE-A2) | A2 | YLQLVFGIEV | (SEQ ID NO: 43) |
| | A24 | EYLQLVFGI | (SEQ ID NO: 44) |
| | B37 | REPVTKAEML | (SEQ ID NO: 34) |
| | Cw7 | EGDCAPEEK | (SEQ ID NO: 45) |
| | DR13 | LLKYRAREPVTKAE | (SEQ ID NO: 46) |
| melanoma antigen family A, 3 (MAGE-A3) | A1 | EVDPIGHLY | (SEQ ID NO: 47) |
| | A2 | FLWGPRALV | (SEQ ID NO: 48) |
| | A2 | KVAELVHFL | (SEQ ID NO: 49) |
| | A24 | TFPDLESEF | (SEQ ID NO: 50) |
| | A24 | VAELVHFLL | (SEQ ID NO: 51) |
| | B18 | MEVDPIGHLY | (SEQ ID NO: 52) |
| | B35 | EVDPIGHLY | (SEQ ID NO: 47) |
| | B37 | REPVTKAEML | (SEQ ID NO: 34) |
| | B40 | AELVHFLLL | (SEQ ID NO: 53) |
| | B44 | MEVDPIGHLY | (SEQ ID NO: 52) |
| | B52 | WQYFFPVIF | (SEQ ID NO: 54) |
| | Cw7 | EGDCAPEEK | (SEQ ID NO: 45) |
| | DP4 | KKLLTQHFVQENYLEY | (SEQ ID NO: 55) |
| | DQ6 | KKLLTQHFVQENYLEY | (SEQ ID NO: 55) |
| | DR1 | ACYEFLWGPRALVETS | (SEQ ID NO: 56) |
| | DR4 | RKVAELVHFLLLKYR | (SEQ ID NO: 57) |
| | DR4 | VIFSKASSSLQL | (SEQ ID NO: 58) |
| | DR7 | VIFSKASSSLQL | (SEQ ID NO: 58) |
| | DR7 | VFGIELMEVDPIGHL | (SEQ ID NO: 59) |
| | DR11 | GDNQIMPKAGLLIIV | (SEQ ID NO: 60) |
| | DR11 | TSYVKVLHHMVKISG | (SEQ ID NO: 61) |
| | DR13 | RKVAELVHFLLLKYRA | (SEQ ID NO: 62) |
| | DR13 | FLLLKYRAREPVTKAE | (SEQ ID NO: 41) |
| melanoma antigen family A, 4 (MAGE-A4) | A1 | EVDPASNTY | (SEQ ID NO: 63) |
| | A2 | GVYDGREHTV | (SEQ ID NO: 64) |
| | A24 | NYKRCFPVI | (SEQ ID NO: 65) |
| | B37 | SESLKMIF | (SEQ ID NO: 66) |
| melanoma antigen family A, 6 (MAGE-A6) | A34 | MVKISGGPR | (SEQ ID NO: 67) |
| | B35 | EVDPIGHVY | (SEQ ID NO: 68) |
| | B37 | REPVTKAEML | (SEQ ID NO: 34) |
| | Cw7 | EGDCAPEEK | (SEQ ID NO: 45) |

TABLE 2-continued

"Shared tumor-specific antigens": Antigens that are shared between many tumors but not present in normal tissues

| Antigen | HLA allele | Epitope | |
|---|---|---|---|
| | Cw16 | ISGGPRISY | (SEQ ID NO: 69) |
| | DR13 | LLKYRAREPVTKAE | (SEQ ID NO: 46) |
| melanoma antigen family A, 9 (MAGE-A9) | A2 | ALSVMGVYV | (SEQ ID NO: 70) |
| melanoma antigen family A, 10 (MAGE-A10) | A2 | GLYDGMEHL | (SEQ ID NO: 71) |
| | B53 | DPARYEFLW | (SEQ ID NO: 35) |
| melanoma antigen family A, 12 (MAGE-A12) | A2 | FLWGPRALV | (SEQ ID NO: 48) |
| | Cw7 | VRIGHLYIL | (SEQ ID NO: 72) |
| | Cw7 | EGDCAPEEK | (SEQ ID NO: 45) |
| | DP4 | REPFTKAEMLGSVIR | (SEQ ID NO: 73) |
| | DR13 | AELVHFLLLKYRAR | (SEQ ID NO: 74) |
| melanoma antigen family C, 1 (MAGE-C1) | DQ6 | SSALLSIFQSSPE | (SEQ ID NO: 75) |
| | DQ6 | SFSYTLLSL | (SEQ ID NO: 76) |
| | DR15 | VSSFFSYTL | (SEQ ID NO: 77) |
| melanoma antigen family C, 2 (MAGE-C2) | A2 | LLFGLALIEV | (SEQ ID NO: 78) |
| | A2 | ALKDVEERV | (SEQ ID NO: 79) |
| | B44 | SESIKKKVL | (SEQ ID NO: 80) |
| cancer/testis antigen 1B (NY-ESO 1/ LAGE-2) | A2 | SLLMWITQC | (SEQ ID NO: 19) |
| | A2 | MLMAQEALAFL | (SEQ ID NO: 18) |
| | A31 | ASGPGGGAPR | (SEQ ID NO: 81) |
| | A31 | LAAQERRVPR | (SEQ ID NO: 20) |
| | A68 | TVSGNILTIR | (SEQ ID NO: 82) |
| | B7 | APRGPHGGAASGL | (SEQ ID NO: 83) |
| | B35 | MPFATPMEA | (SEQ ID NO: 84) |
| | B49 | KEFTVSGNILTI | (SEQ ID NO: 85) |
| | B51 | MPFATPMEA | (SEQ ID NO: 84) |
| | Cw3 | LAMPFATPM | (SEQ ID NO: 86) |
| | Cw6 | ARGPESRLL | (SEQ ID NO: 87) |
| | DP4 | SLLMWITQCFLPVF | (SEQ ID NO: 23) |
| | DP4 | LLEFYLAMPFATPMEAELARRSLAQ | (SEQ ID NO: 88) |
| | DR1 | LLEFYLAMPFATPMEAELARRSLAQ | (SEQ ID NO: 88) |
| | DR1 | EFYLAMPFATPM | (SEQ ID NO: 89) |
| | DR1 | PGVLLKEFTVSGNILTIRLTAADHR | (SEQ ID NO: 90) |
| | DR2 | RLLEFYLAMPFA | (SEQ ID NO: 91) |
| | DR3 | QGAMLAAQERRVPRAAEVPR | (SEQ ID NO: 24) |
| | DR4 | PFATPMEAELARR | (SEQ ID NO: 92) |
| | DR4 | PGVLLKEFTVSGNILTIRLT | (SEQ ID NO: 93) |
| | DR4 | VLLKEFTVSG | (SEQ ID NO: 94) |
| | DR4 | AADHRQLQLSISSCLQQL | (SEQ ID NO: 25) |
| | DR4 | LLEFYLAMPFATPMEAELARRSLAQ | (SEQ ID NO: 88) |
| | DR52b | LKEFTVSGNILTIRL | (SEQ ID NO: 95) |
| | DR7 | PGVLLKEFTVSGNILTIRLTAADHR | (SEQ ID NO: 90) |
| | DR7 | LLEFYLAMPFATPMEAELARRSLAQ | (SEQ ID NO: 88) |
| | DR8 | KEFTVSGNILT | (SEQ ID NO: 96) |
| | DR9 | LLEFYLAMPFATPM | (SEQ ID NO: 97) |
| | DR15 | AGATGGRGPRGAGA | (SEQ ID NO: 28) |
| synovial sarcoma, X breakpoint 2 (SSX-2) | A2 | KASEKIFYV | (SEQ ID NO: 98) |
| | DP1 | EKIQKAFDDIAKYFSK | (SEQ ID NO: 99) |
| | DR3 | WEKMKASEKIFYVYMKRK | (SEQ ID NO: 100) |
| | DR4 | KIFYVYMKRKYEAMT | (SEQ ID NO: 101) |
| | DR11 | KIFYVYMKRKYEAM | (SEQ ID NO: 102) |
| synovial sarcoma, X breakpoint 4 (SSX-4) | DP10 | INKTSGPKRGKHAWTHRLRE | (SEQ ID NO: 103) |
| | DR3 | YFSKKEWEKMKSSEKIVYVY | (SEQ ID NO: 104) |
| | DR8 | MKLNYEVMTKLGFKVTLPPF | (SEQ ID NO: 105) |
| | DR8 | KHAWTHRLRERKQLVVYEEI | (SEQ ID NO: 106) |
| | DR11 | LGFKVTLPPFMRSKRAADFH | (SEQ ID NO: 107) |
| | DR15 | KSSEKIVYVYMKLNYEVMTK | (SEQ ID NO: 108) |
| | DR52 | KHAWTHRLRERKQLVVYEEI | (SEQ ID NO: 106) |
| Transient axonal glycoprotein 1 (TAG-1) | A2 | SLGWLFLLL | (SEQ ID NO: 109) |
| | B8 | LSRLSNRLL | (SEQ ID NO: 110) |

TABLE 2-continued

"Shared tumor-specific antigens": Antigens that are shared between many tumors but not present in normal tissues

| Antigen | HLA allele | Epitope | |
|---|---|---|---|
| Taxol-resistant-associated gene 3 (TRAG-3) | DR1 | CEFHACWPAFTVLGE | (SEQ ID NO: 111) |
| | DR4 | CEFHACWPAFTVLGE | (SEQ ID NO: 111) |
| | DR7 | CEFHACWPAFTVLGE | (SEQ ID NO: 111) |

TABLE 3

"Differentiation antigens": Antigens that are shared between many tumors, and are also expressed in the normal tissue of origin of the malignancy

| Cancer | Antigen | HLA allele | Epitope | |
|---|---|---|---|---|
| Gut carcinoma | carcinoembryonic antigen-related cell adhesion molecule 5 (CEA) | A2 | YLSGANLN | (SEQ ID NO: 112) |
| | | A2 | IMIGVLVGV | (SEQ ID NO: 113) |
| | | A2 | GVLVGVALI | (SEQ ID NO: 114) |
| | | A3 | HLFGYSWYK | (SEQ ID NO: 115) |
| | | A24 | QYSWFVNGTF | (SEQ ID NO: 116) |
| | | A24 | TYACFVSNL | (SEQ ID NO: 117) |
| | | DR3 | AYVCGIQNSVSANRS | (SEQ ID NO: 118) |
| | | DR4 | DTGFYTLHVIKSDLVNEEATGQFRV | (SEQ ID NO: 119) |
| | | DR4 | YSWRINGIPQQHTQV | (SEQ ID NO: 120) |
| | | DR7 | TYYRPGVNLSLSC | (SEQ ID NO: 121) |
| | | DR7 | EIIYPNASLLIQN | (SEQ ID NO: 122) |
| | | DR9 | YACFVSNLATGRNNS | (SEQ ID NO: 123) |
| | | DR11 | LWWVNNQSLPVSP | (SEQ ID NO: 124) |
| | | DR13 | LWWVNNQSLPVSP | (SEQ ID NO: 124) |
| | | DR14 | LWWVNNQSLPVSP | (SEQ ID NO: 124) |
| | | DR14 | EIIYPNASLLIQN | (SEQ ID NO: 122) |
| | | DR14 | NSIVKSITVSASG | (SEQ ID NO: 125) |
| Melanoma | gp100/Pme17 | A2 | KTWGQYWQV | (SEQ ID NO: 126) |
| | | A2 | (A)MLGTHTMEV | (SEQ ID NO: 127) |
| | | A2 | ITDQVPFSV | (SEQ ID NO: 128) |
| | | A2 | YLEPGPVTA | (SEQ ID NO: 129) |
| | | A2 | LLDGTATLRL | (SEQ ID NO: 130) |
| | | A2 | VLYRYGSFSV | (SEQ ID NO: 131) |
| | | A2 | SLADTNSLAV | (SEQ ID NO: 132) |
| | | A2 | RLMKQDFSV | (SEQ ID NO: 133) |
| | | A2 | RLPRIFCSC | (SEQ ID NO: 134) |
| | | A3 | LIYRRRLMK | (SEQ ID NO: 135) |
| | | A3 | ALLAVGATK | (SEQ ID NO: 136) |
| | | A3 | IALNFPGSQK | (SEQ ID NO: 137) |
| | | A3 | ALNFPGSQK | (SEQ ID NO: 138) |
| | | A11 | ALNFPGSQK | (SEQ ID NO: 138) |
| | | A24 | VYFFLPDHL | (SEQ ID NO: 139) |
| | | A32 | RTKQLYPEW | (SEQ ID NO: 140) |
| | | A68 | HTMEVTVYHR | (SEQ ID NO: 141) |
| | | B7 | SSPGCQPPA | (SEQ ID NO: 142) |
| | | B35 | VPLDCVLYRY | (SEQ ID NO: 143) |
| | | B35 | LPHSSSHWL | (SEQ ID NO: 144) |
| | | Cw8 | SNDGPTLI | (SEQ ID NO: 145) |
| | | DQ6 | GRAMLGTHTMEVTVY | (SEQ ID NO: 146) |
| | | DR4 | WNRQLYPEWTEAQRLD | (SEQ ID NO: 147) |
| | | DR7 | TTEWVETTARELPIPEPE | (SEQ ID NO: 148) |
| | | DR7 | TGRAMLGTHTMEVTVYH | (SEQ ID NO: 149) |
| | | DR53 | GRAMLGTHTMEVTVY | (SEQ ID NO: 146) |
| Prostate cancer | Kallikrein 4 | DP4 | SVSESDTIRSISIAS | (SEQ ID NO: 150) |
| | | DP4 | LLANGRMPTVLQCVN | (SEQ ID NO: 151) |
| | | DR7 | RMPTVLQCVNVSVVS | (SEQ ID NO: 152) |
| Breast cancer | Mammaglobin-A | A3 | PLLENVISK | (SEQ ID NO: 153) |
| melanoma | Melan-A/MART-1 | A2 | (E)AAGIGILTV | (SEQ ID NO: 154) |
| | | A2 | ILTVILGVL | (SEQ ID NO: 155) |
| | | B35 | EAAGIGILTV | (SEQ ID NO: 156) |
| | | B45 | AEEAAGIGIL(T) | (SEQ ID NO: 157) |
| | | Cw7 | RNGYRALMDKS | (SEQ ID NO: 158) |

TABLE 3-continued

"Differentiation antigens": Antigens that are shared between many tumors, and are also expressed in the normal tissue of origin of the malignancy

| Cancer | Antigen | HLA allele | Epitope | |
|---|---|---|---|---|
| | | DQ6 | EEAAGIGILTVI | (SEQ ID NO: 159) |
| | | DR1 | AAGIGILTVILGVL | (SEQ ID NO: 160) |
| | | DR1 | APPAYEKLpSAEQ (phosphopeptide) | (SEQ ID NO: 161) |
| | | DR3 | EEAAGIGILTVI | (SEQ ID NO: 159) |
| | | DR4 | RNGYRALMDKSLHVGTQCALTRR | (SEQ ID NO: 162) |
| | | DR11 | MPREDAHFIYGYPKKGHGHS | (SEQ ID NO: 163) |
| | | DR52 | KNCEPVVPNAPPAYEKLSAE | (SEQ ID NO: 164) |
| Prostate carcinoma | acid phosphatase, prostate (PAP) | A2 | FLFLLFFWL | (SEQ ID NO: 165) |
| | | A2 | TLMSAMTNL | (SEQ ID NO: 166) |
| | | A2 | ALDVYNGLL | (SEQ ID NO: 167) |
| Prostate carcinoma | prostate specific antigen (PSA) | A2 | FLTPKKLQCV | (SEQ ID NO: 168) |
| | | A2 | VISNDVCAQV | (SEQ ID NO: 169) |
| Melanoma | tyrosinase-related protein 1 (TRP-1/gp75) | A31 | MSLQRQFLR | (SEQ ID NO: 170) |
| | | DR4 | ISPNSVFSQWRVVCDSLEDYD | (SEQ ID NO: 171) |
| | | DR15 | SLPYWNFATG | (SEQ ID NO: 172) |
| Melanoma | tyrosinase-related protein 2 (TRP-2) | A2 | SVYDFFVWL | (SEQ ID NO: 173) |
| | | A2 | TLDSQVMSL | (SEQ ID NO: 174) |
| | | A31 | LLGPGRPYR | (SEQ ID NO: 175) |
| | | A33 | LLGPGRPYR | (SEQ ID NO: 175) |
| | | Cw8 | ANDPIFVVL | (SEQ ID NO: 176) |
| | | DR3 | QCTEVRADTRPWSGP | (SEQ ID NO: 177) |
| | | DR15 | ALPYWNFATG | (SEQ ID NO: 178) |
| Melanoma | tyrosinase | A1 | KCDICTDEY | (SEQ ID NO: 179) |
| | | A1 | SSDYVIPIGTY | (SEQ ID NO: 180) |
| | | A2 | MLLAVLYCL | (SEQ ID NO: 181) |
| | | A2 | CLLWSFQTSA | (SEQ ID NO: 182) |
| | | A2 | YMDGTMSQV | (SEQ ID NO: 183) |
| | | A24 | AFLPWHRLF | (SEQ ID NO: 184) |
| | | A26 | QCSGNFMGF | (SEQ ID NO: 185) |
| | | B35 | TPRLPSSADVEF | (SEQ ID NO: 186) |
| | | B35 | LPSSADVEF | (SEQ ID NO: 187) |
| | | B38 | LHHAFVDSIF | (SEQ ID NO: 188) |
| | | B44 | SEIWRDIDF | (SEQ ID NO: 189) |
| | | DR4 | QNILLSNAPLGPQFP | (SEQ ID NO: 190) |
| | | DR4 | SYLQDSDPDSFQD | (SEQ ID NO: 191) |
| | | DR15 | FLLHHAFVDSIFEQWLQRHRP | (SEQ ID NO: 192) |

TABLE 4

"Overexpressed antigens": Antigens that are shared between many tumors, overexpressed in tumors and are also expressed in a wide variety of normal tissues

| Normal tissue expression | Antigen | HLA alleles | epitopes | |
|---|---|---|---|---|
| Ubiquitous (low level) | enhancer of zeste homolog 2 (EZH-2) | A2 | FMVEDETVL | (SEQ ID NO: 193) |
| | | A2 | FINDEIFVEL | (SEQ ID NO: 194) |
| | | A24 | KYDCFLHPF | (SEQ ID NO: 195) |
| | | A24 | KYVGIEREM | (SEQ ID NO: 196) |
| Ubiquitous (low level) | v-erb-b2 erythroblastic leukemia viral oncogene homolog 2, neuro/glioblastoma derived oncogene homolog (HER-2/neu) | A2 | KIFGSLAFL | (SEQ ID NO: 197) |
| | | A2 | IISAVVGIL | (SEQ ID NO: 198) |
| | | A2 | ALCRWGLLL | (SEQ ID NO: 199) |
| | | A2 | ILHNGAYSL | (SEQ ID NO: 200) |
| | | A2 | RLLQETELV | (SEQ ID NO: 201) |
| | | A2 | VVLGVVFGI | (SEQ ID NO: 202) |
| | | A2 | YMIMVKCWMI | (SEQ ID NO: 203) |
| | | A2 | HLYQGCQVV | (SEQ ID NO: 204) |
| | | A2 | YLVPQQGFFC | (SEQ ID NO: 205) |
| | | A2 | PLQPEQLQV | (SEQ ID NO: 206) |
| | | A2 | TLEEITGYL | (SEQ ID NO: 207) |
| | | A2 | ALIHHNTHL | (SEQ ID NO: 208) |
| | | A2 | PLTSIISAV | (SEQ ID NO: 209) |

TABLE 4-continued

"Overexpressed antigens": Antigens that are shared between many tumors, overexpressed in tumors and are also expressed in a wide variety of normal tissues

| Normal tissue expression | Antigen | HLA alleles | epitopes | |
|---|---|---|---|---|
| | | A3 | VLRENTSPK | (SEQ ID NO: 210) |
| | | A24 | TYLPTNASL | (SEQ ID NO: 211) |
| liver | alpha-foetoprotein | A2 | GVALQTMKQ | (SEQ ID NO: 212) |
| | | A2 | FMNKFIYEI | (SEQ ID NO: 213) |
| | | DR13 | QLAVSVILRV | (SEQ ID NO: 214) |
| glandular epithelia | mucin 1, cell surface associated (MUC-1) | A2 | STAPPVHNV | (SEQ ID NO: 215) |
| | | A2 | LLLLTVLTV | (SEQ ID NO: 216) |
| | | DR3 | PGSTAPPAHGVT | (SEQ ID NO: 217) |
| Ubiquitous (low level) | tumor protein p53 (p53) | A2 | LLGRNSFEV | (SEQ ID NO: 218) |
| | | A2 | RMPEAAPPV | (SEQ ID NO: 219) |
| | | B46 | SQKTYQGSY | (SEQ ID NO: 220) |
| | | DP5 | PGTRVRAMAIYKQ | (SEQ ID NO: 221) |
| | | DR14 | HLIRVEGNLRVE | (SEQ ID NO: 222) |
| Testis, ovary, endometrium, adrenals | preferentially expressed antigen in melanoma (PRAME) | A2 | VLDGLDVLL | (SEQ ID NO: 223) |
| | | A2 | SLYSFPEPEA | (SEQ ID NO: 224) |
| | | A2 | ALYVDSLFFL | (SEQ ID NO: 225) |
| | | A2 | SLLQHLIGL | (SEQ ID NO: 226) |
| | | A24 | LYVDSLFFL | (SEQ ID NO: 227) |
| Prostate, Central Nervous System, liver | hydrolase (prostate-specific membrane antigen) 1 (PSMA) | A24 | NYARTEDFF | (SEQ ID NO: 228) |
| retina | renal tumor antigen (RAGE-1) | A2 | LKLSGVVRL | (SEQ ID NO: 229) |
| | | A2 | PLPPARNGGL | (SEQ ID NO: 230) |
| | | B7 | SPSSNRIRNT | (SEQ ID NO: 231) |
| heart, skeletal muscle, pericytes | regulator of G-protein signaling 5 (RGS5) | A2 | LAALPHSCL | (SEQ ID NO: 232) |
| | | A3 | GLASFKSFLK | (SEQ ID NO: 233) |
| | ring finger protein 43 (RNF43) | A2 | ALWPWLLMA(T) | (SEQ ID NO: 234) |
| | | A24 | NSQPVWLCL | (SEQ ID NO: 235) |
| Ubiquitous (low level) | sex determining region Y)-box 10 (SOX-10) | A2 | AWISKPPGV | (SEQ ID NO: 236) |
| | | A2 | SAWISKPPGV | (SEQ ID NO: 237) |
| prostate | six transmembrane epithelial antigen of the prostate 1 (STEAP1) | A2 | MIAVFLPIV | (SEQ ID NO: 238) |
| | | A2 | HQQYFYKIPILVINK | (SEQ ID NO: 239) |
| testis, thymus, bone marrow, lymph nodes | Telomerase | A2 | ILAKFLHWL | (SEQ ID NO: 240) |
| | | A2 | RLVDDFLLV | (SEQ ID NO: 241) |
| | | DR7 | RPGLLGASVLGLDDI | (SEQ ID NO: 242) |
| | | DR11 | LTDLQPYMRQFVAHL | (SEQ ID NO: 243) |
| testis, ovary, bone marrow, spleen | Wils tumor 1 (WT1) | A1 | TSEKRPFMCAY | (SEQ ID NO: 244) |
| | | A24 | CMTWNQMNL | (SEQ ID NO: 245) |
| | | DP5 | LSHLQMHSRKH | (SEQ ID NO: 246) |
| | | DR4 | KRYFKLSHLQMHSRKH | (SEQ ID NO: 247) |
| Skin, lung, small intestine | EPH receptor A2 (EphA2) | A2 | TLADFDPRV | (SEQ ID NO: 248) |
| Ubiquitous, low level | sex-determining region Y-box protein 2 (SOX2) | A2 | ALSPASSSRSV | (SEQ ID NO: 249) |
| Reactive astrocytes, macrophages, chondrocytes, neutrophils synovial cells | chitinase 3-like 1 (CHI3L1, YKL40) | A2 | SIMTYDFHGA | (SEQ ID NO: 250) |
| Ubiquitous (at mRNA level) | adenosine diphosphate-ribosylation factor 4-like (ARF4L) protein | A2 | FLPHFQALHV | (SEQ ID NO: 251) |

TABLE 4-continued

"Overexpressed antigens": Antigens that are shared between many tumors, overexpressed in tumors and are also expressed in a wide variety of normal tissues

| Normal tissue expression | Antigen | HLA alleles | epitopes | |
|---|---|---|---|---|
| Ubiquitous, low level | squamous cell carcinoma antigen recognized by T cells 1 (SART-1) | A24 | EYRGFTQDF | (SEQ ID NO: 252) |
| Ubiquitous, low level | squamous cell carcinoma antigen recognized by T cells 3 (SART-3) | A24 | VYDYNCHVDL | (SEQ ID NO: 253) |
| Lung epithelial cells, fibroblasts | IL-13 receptor α2 chain | A2 | ALPFGFILV | (SEQ ID NO: 254) |
| Lung, kidney, spleen | UDP-Gal:βGlcNAc β1,3-galactosyltransferase, polypeptide 3 (GALT3) | A2 | TIMAFRWVT | (SEQ ID NO: 255) |

Note
that the epitopes of the 8 last antigens of Table 4 have been described in glioma.

In another aspect of the invention, the CD4+ and CD8+ epitopes are antigenic determinants from a pathogen antigenic protein.

Examples of viral antigens can be selected from the group consisting of viral meningitis, tuberculosis, encephalitis, dengue or smallpox, or it can be an antigen of a virus selected from the group consisting of smallpox virus, hepatitis type A, hepatitis type B, hepatitis type C, influenza, varicella, adenovirus, herpes simplex type I (HSV-I), herpes simplex type U (HSV-II), rinderpest, rhinovirus, echovirus, rotavirus, respiratory syncytial virus, human papilloma virus (including HPV 16 and HPV 18), papova virus, cytomegalovirus, echinovirus, arbovirus, hantavirus, coxsackie virus, mumps virus, measles virus, rubella virus, polio virus, human immunodeficiency virus (HIV), human immunodeficiency virus type I (HIV-I), human immunodeficiency virus type II (HIV-II), rabies virus, Human T-lymphotropic virus-1 (HTLV-1), Kaposi's sarcoma herpesvirus (KSHV), Merkel cell polyomavirus (MCV), and Epstein Barr virus. In certain embodiments, the HIV vaccine comprises the GPI antigen or a portion or mutant thereof.

Examples of bacterial antigens can be selected from the group consisting of antigens of *Helicobacter pylori, Chlamydia pneumoniae, Chlamydia trachomatis, Ureaplasma urealyticum, Mycoplasma pneumoniae, Staphylococcus* spp., *Staphylococcus aureus, Streptococcus* spp., *Streptococcus pyogenes, Streptococcus pneumoniae, Streptococcus viridans, Enterococcus faecalis, Neisseria meningitidis, Neisseria gonorrhoeae, Bacillus anthracis, Salmonella* spp., *Salmonella typhi, Vibrio cholera, Pasteurella pestis, Pseudomonas aeruginosa, Campylobacter* spp., *Campylobacter jejuni, Clostridium* spp., *Clostridium difficile, Mycobacterium* spp., *Mycobacterium tuberculosis, Treponema* spp., *Borrelia* spp., *Borrelia burgdorferi, Leptospria* spp., *Hemophilus ducreyi, Corynebacterium diphtheria, Bordetella pertussis, Bordetella parapertussis, Bordetella bronchiseptica, hemophilus influenza, Escherichia coli, Shigella* spp., *Erlichia* spp., *Rickettsia* spp. and combinations thereof.

Examples of protozoal antigens can be selected from the group consisting of antigens of *leishmania, kokzidioa*, and *trypanosoma*.

TABLE 5

Examples of epitopes from antigenic protein from pathogens which can be comprised in the polypeptide of the invention

| Pathogen | Antigen | HLA allele | Epitope | |
|---|---|---|---|---|
| Lassa Virus | GPC | A2 | GLVGLVTFL | (SEQ ID NO: 256) |
| | | A2 | SLYKGVYEL | (SEQ ID NO: 257) |
| | | A2 | YLISIFLHL | (SEQ ID NO: 258) |
| | | DRB1*0101 | NSFYYMKGGVNTFLI | (SEQ ID NO: 259) |
| | | DRB1*0101 | SKTHLNFERSLKAFF | (SEQ ID NO: 260) |
| Human Papillomavirus (HPV 16) | E7 | A2 | TLGIVZPI | (SEQ ID NO: 261) |
| | E7 | A2 | YMLDLQPETT | (SEQ ID NO: 262) |
| | E7 | DR17 | CCKCDSTLRLC | (SEQ ID NO: 263) |
| Mycobacterium tuberculosis | CFP10 | B4501 | AEMKTDAA | (SEQ ID NO: 264) |
| | CFP10 | B1502 | NIRQAGVQY | (SEQ ID NO: 265) |
| | MPT63 | DR# | MKLTTMIKTAVVAMAAIATFAAP | (SEQ ID NO: 266) |
| | HSP 65 | DRB1*0301 | KTIAYDEEARR | (SEQ ID NO: 267) |

TABLE 5-continued

Examples of epitopes from antigenic protein from pathogens which can be comprised in the polypeptide of the invention

| Pathogen | Antigen | HLA allele | Epitope | |
|---|---|---|---|---|
| Chlamydia trachomatis | MOMP | A2 | RLNMFTPYI | (SEQ ID NO: 268) |
| Clostridium tetani | Tetanus toxin | DP1*0401 | FNNFTVSFWLRVPKVSASHLE | (SEQ ID NO: 269) |
| Human Immunodeficiency Virus (HIV) | GP | DP1*0401 | TEKLWVTVYYGVPVW | (SEQ ID NO: 270) |
| | Nef | Cw *0701 | KRQEILDLWVY | (SEQ ID NO: 271) |
| | p24 | B*57/5801 | TSTLQEQIAW | (SEQ ID NO: 272) |

Promiscuous binding to multiple DR alleles

In a further aspect, the polypeptide of the invention comprises at least two CD4+ epitopes and/or at least two CD8+ epitopes.

In humans, the epitopes that are presented to CD8+ T cells are bound to highly polymorphic MHC class I molecules, specifically the alleles of HLA-A (>400 alleles), HLA-B (>700 alleles), and HLA-C (>200 alleles). The polymorphic MHC class II isotypes responsible for binding peptides recognized by CD4+ T cells are HLA-DR (DRA 3 alleles, DRB>500 alleles), HLA-DP (DPA>20 alleles, DPB>100 allotypes) and HLA-DQ (DQA>30 alleles, DQB>60 alleles). Although the HLA genes are extremely polymorphic, the same alleles are frequently associated in the same individual, and within an ethnic group, diversity is more restricted.

Therefore, in order to cover a broad range of epitopes presented in a broad context of MHC molecules representative of a given population, and, thus, to render the polypeptides of the invention useful for patients of disparate MHC alleles, it is preferable that the polypeptides of the invention comprise multiple epitopes restricted by multiple MHC class I or class II molecules of said population.

Preferably, when two or more CD4+ epitopes are comprised in the polypeptide of the invention, said CD4+ epitopes are restricted by at least two MHC class II molecules of the patient population.

Preferably, when two or more CD8+ epitopes are comprised in the polypeptide of the invention, said CD8+ epitopes are restricted by at least two MHC class I molecules of the patient population.

More preferably, when two or more CD4+ epitopes and two or more CD8+ epitopes are comprised in the polypeptides of the invention, said CD4+ epitopes are restricted by at least two MHC class II molecules and said CD8+ epitopes are restricted by at least two MHC class I molecules of the patient population.

There is no upper limit as to how many epitopes can be included in the polypeptide of the invention except for practical feasibility. In a specific aspect, the polypeptide of the invention comprises about 10 epitopes, or any number comprised between 10 to 100 epitopes, preferably 10, 11, 12, 13, 14, 15, 16, 17, 18, 19, 20, 25, 30, 40, 50, 60, 70, 80, 90 or 100 epitopes.

Polynucleotides Encoding the Polypeptides of the Invention

According to another embodiment, it is provided an isolated polynucleotide encoding a polypeptide comprising:
(i) a protein transduction domain consisting of ZEBRA or a fragment thereof that retains the capacity of internalization,
(ii) at least one, preferably at least two, CD4+ epitope(s); and
(iii) at least one, preferably at least two, CD8+ epitope(s).

In a preferred aspect of the polynucleotide of the invention, the protein transduction domain comprises a nucleotide sequence having at least 80%, at least 90%, at least 95%, at least 96%, at least 97%, at least 98%, or at least 99% identity with SEQ ID NO: 7.

In an even more preferred aspect of the polynucleotide of the invention, the protein transduction domain comprises or consists of the nucleotide sequence SEQ ID NO: 7.

Production and Purification of the Polypeptides of the Invention

In another embodiment, it is provided a recombinant vector comprising a polynucleotide according to the invention.

Numerous expression systems can be used, including without limitation chromosomes, episomes, and derived viruses. More particularly, the recombinant vectors used can be derived from bacterial plasmids, transposons, yeast episomes, insertion elements, yeast chromosome elements, viruses such as baculovirus, papilloma viruses such as SV40, vaccinia viruses, adenoviruses, fox pox viruses, pseudorabies viruses, retroviruses.

These recombinant vectors can equally be cosmid or phagemid derivatives. The nucleotide sequence can be inserted in the recombinant expression vector by methods well known to a person skilled in the art such as, for example, those that are described in MOLECULAR CLONING: A LABORATORY MANUAL, Sambrook et al., 4th Ed., Cold Spring Harbor Laboratory Press, Cold Spring Harbor, N.Y., 2001.

The recombinant vector can include nucleotide sequences that control the regulation of the polynucleotide expression as well as nucleotide sequences permitting the expression and the transcription of a polynucleotide of the invention and the translation of a polypeptide of the invention, these sequences being selected according to the host cells that are used.

Thus, for example, an appropriate secretion signal can be integrated in the recombinant vector so that the polypeptide, encoded by the polynucleotide of the invention, will be directed towards the lumen of the endoplasmic reticulum, towards the periplasmic space, on the membrane or towards the extracellular environment. The choice of an appropriate secretion signal may facilitate subsequent protein purification.

In a further embodiment, it is provided a host cell comprising a recombinant vector according to the invention.

The introduction of the recombinant vector in a host cell can be carried out according to methods that are well known to a person skilled in the art, such as those described in BASIC METHODS IN MOLECULAR BIOLOGY, Davis et al., 2nd ed., McGraw-Hill Professional Publishing, 1995, and MOLECULAR CLONING: A LABORATORY MANUAL, supra, such as transfection by calcium phosphate, transfection by DEAE dextran, transfection, microinjection, transfection by cationic lipids, electroporation, transduction or infection.

The host cell can be, for example, bacterial cells such as *E. coli*, cells of fungi such as yeast cells and cells of *Aspergillus, Streptomyces*, insect cells, Chinese Hamster Ovary cells (CHO), C127 mouse cell line, BHK cell line of Syrian hamster cells, Human Embryonic Kidney 293 (HEK 293) cells.

The host cells can be used, for example, to express a polypeptide of the invention. After purification by standard methods, the polypeptide of the invention can be used in a method described hereinafter.

It is a further object of the invention to provide a method for preparing a polypeptide according to the invention, comprising cultivating a host cell as mentioned above in a culture medium and separating said polypeptide from the culture medium or separating said polypeptide from the host cell lysate after host cell lysis.

Antigen-Presenting Cells Loaded with the Polypeptide of the Invention

In another embodiment, it is provided antigen-presenting cells loaded with the polypeptides of the invention.

In an aspect of the invention, the antigen presenting cells are selected among dendritic cells, macrophages and B-cells. Dendritic cells, in particular dendritic cells (conventional and plasmacytoid) from the patient to be treated, are preferred.

Methods to extract antigen-presenting cells, in particular dendritic cells, from the patient are known to the skilled person. They include harvesting monocytes or hematopoietic stem cells from bone marrow, cord blood, or peripheral blood. They also include the use of embryonic stem (ES) cells and induced pluripotent stem cells (iPS). Antigen presenting cells, in particular dendritic cells or their precursors, can be enriched by methods including elutriation and magnetic bead based separation, which may involve enrichment for $CD14^+$ precursor cells.

Methods to load the polypeptide of the invention into the above-mentioned antigen presenting cells and further prepare such cells before administration to the patient are known to one skilled in the art. Preparation of dendritic cells can include their culture or differentiation using cytokines that may include GM-CSF and IL-4. Dendritic cell lines may also be employed. Loading of the polypeptide of the invention to the dendritic cells can involve co-incubation of the polypeptide of the invention with the cells in culture, making use of the intrinsic properties of the invention (i.e. the protein transduction domain). Further culture of the dendritic cells thus loaded to induce efficient maturation can include addition of cytokines including IL-1β, IL-6, TNFα, PGE2, IFNα, and adjuvants which may include poly-IC.

It is also an object of the invention to provide a method for preparing antigen presenting cells as mentioned above, comprising transducing antigen presenting cells with a polypeptide of the invention, cultivating said cells in a culture medium and separating said cells from the culture medium.

Compositions According to the Invention

The invention provides pharmaceutical compositions, in particular vaccine compositions, and methods for treating a subject, preferably a mammalian subject, and most preferably a human patient who is suffering from a medical disorder, and in particular a disorder that can be treated by immunotherapy such as cancers, infectious diseases, autoimmunity disorders and transplant rejections.

Pharmaceutical compositions, in particular vaccine compositions, or formulations according to the invention may be administered as a pharmaceutical formulation which can contain a polypeptide according to the invention in any form described herein.

Pharmaceutical compositions, in particular vaccine compositions, or formulations according to the invention may also be administered as a pharmaceutical formulation which can contain antigen presenting cells loaded with a polypeptide according to the invention in any form described herein.

The compositions according to the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous and intradermal) use by injection or continuous infusion. Injectable compositions are typically based upon injectable sterile saline or phosphate-buffered saline or other injectable carriers known in the art. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Examples of suitable adjuvants include MPL® (Corixa), aluminum-based minerals including aluminum compounds (generically called Alum), ASO1-4, MF59, CalciumPhosphate, Liposomes, Iscom, polyinosinic:polycytidylic acid (polyIC), including its stabilized form poly-ICLC (Hiltonol), CpG oligodeoxynucleotides, Granulocyte-macrophage colony-stimulating factor (GM-CSF), lipopolysaccharide (LPS), Montanide, PLG, Flagellin, QS21, RC529, IC31, Imiquimod, Resiquimod, ISS, and Fibroblast-stimulating lipopeptide (FSL1).

Compositions of the invention may be liquid formulations including, but not limited to, aqueous or oily suspensions, solutions, emulsions, syrups, and elixirs. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®.

Compositions of the invention may also be formulated as a depot preparation, which may be administered by implantation or by intramuscular injection.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

The compounds of this invention can also be administered in sustained release forms or from sustained release drug delivery systems.

According to a particular embodiment, compositions according to the invention are for subcutaneous use.

In another particular aspect, the compositions according to the invention are adapted for delivery by repeated administration.

Further materials as well as formulation processing techniques and the like are set out in *Part 5 of Remington's Pharmaceutical Sciences*, 21$^{st}$ Edition, 2005, Lippincott Williams & Wilkins, which is incorporated herein by reference.

Another object of the invention is to provide a method of preparing a pharmaceutical composition according to the invention comprising the step of mixing a polypeptide according to the invention or antigen-presenting cells loaded with a polypeptide of the invention, and a pharmaceutically acceptable carrier.

The polypeptides according to the invention, antigen-presenting cells loaded with the polypeptides of the invention, compositions according to the invention, formulations thereof or a method according to the invention are useful in the prevention and/or treatment of a disease or a disorder, in particular those that can be treated or prevented by immunotherapy such as cancers and infectious diseases.

Another object of the invention is a vaccination kit for treating, preventing or stabilizing a cancer or an infectious disease, comprising the pharmaceutical composition according to the invention and instructions for use of said pharmaceutical composition.

Methods and Uses According to the Invention

According to one embodiment, it is provided a method for eliciting or improving, in a subject, an immunologic response against multiple epitopes that is dependent on CD4$^+$ helper T cells and CD8$^+$ cytotoxic T cells, wherein said method comprises administering a polypeptide of the invention to said subject.

According to another embodiment, it is provided a method for eliciting or improving, in a subject, an immunologic response against multiple epitopes that is dependent on CD4$^+$ helper T cells and CD8$^+$ cytotoxic T cells, wherein said method comprises administering antigen-presenting cells loaded with a polypeptide of the invention to said subject.

An immunologic response that is dependent on CD4$^+$ and CD8$^+$ response can be determined by evaluating an inflammatory response, a pro-inflammatory cytokine response, including an increase in the expression of one or more of IFN-γ, TNF-α and IL-2 mRNA or protein relative to the level before administration of the compounds of the invention. It can also be measured by an increase in the frequency or absolute number of antigen-specific T cells after administration of the compounds of the invention, measured by HLA-peptide multimer staining, ELISPOT assays, and delayed type hypersensitivity tests. It can also be indirectly measured by an increase in antigen-specific serum antibodies that are dependent on antigen-specific T helper cells.

According to another embodiment, it is provided a method for eliciting or improving, in a subject, an immunologic response against multiple epitopes that is restricted by multiple MHC class I molecules and multiple MHC class II molecules, wherein said method comprises administering a polypeptide of the invention.

According to another aspect, it is provided a method for eliciting or improving, in a subject, an immunologic response against multiple epitopes that is restricted by multiple MHC class I molecules and multiple MHC class II molecules, wherein said method comprises administering antigen presenting cells of the invention to said subject.

A method for eliciting or improving, in a subject, an immunologic response against multiple epitopes that is restricted by multiple MHC class I molecules and multiple MHC class II molecules can be determined by evaluating a cytokine response, including an increase in the expression of one or more of IFN-γ, TNF-α and IL-2 mRNA or protein relative to the level before administration of the compounds of the invention, after in vitro stimulation of T cells with individual peptides binding to discrete MHC class I and class II molecules on antigen presenting cells. Restriction to different MHC molecules can also be validated by using antigen presenting cells expressing different MHC molecules, or by using MHC blocking antibodies. It can also be measured by an increase in the frequency or absolute number of antigen-specific T cells after administration of the compounds of the invention, measured by HLA-peptide multimer staining, which uses multimers assembled with discrete MHC molecules.

In a preferred aspect of the methods for eliciting or improving an immunologic response against multiple epitopes according to the invention, the immune response is directed against multiple epitopes of a tumor-associated antigen or a tumor-specific antigen. In another preferred aspect, the immune response is directed against multiple epitopes of an antigenic protein from a pathogen.

Another embodiment of the invention provides the use of a polypeptide of the invention or the use of antigen-presenting cells loaded with a polypeptide of the invention for the preparation of a medicament for the prevention, treatment or stabilization of a disease or disorder, such as those which can be treated by immunotherapy, including cancers, infectious diseases, autoimmunity disorders and transplant rejections.

According to another aspect, the invention provides a method of preventing, treating or repressing a disease or disorder such as those which can be treated by immunotherapy, including cancers, infectious diseases, autoimmunity disorders and transplant rejections, wherein said method comprises administering a polypeptide of the invention, antigen presenting cells of the invention, or a pharmaceutical formulation thereof, to said subject.

In a preferred, uses and methods of the invention comprises administration of a polypeptide according to the invention.

Preferred cancers for the uses and methods of the invention include brain cancer, prostate cancer, breast cancer, ovarian cancer, esophageal cancer, lung cancer, liver cancer, kidney cancer, melanoma, gut carcinoma, lung carcinoma, head and neck squamous cell carcinoma, chronic myeloid leukemia, colorectal carcinoma, gastric carcinoma, endometrial carcinoma, myeloid leukemia, lung squamous cell carcinoma, acute lymphoblastic leukemia, acute myelogenous leukemia, bladder tumor, promyelocytic leukemia, non-small cell lung carcinoma, sarcoma.

The cancer may be a solid tumor, blood cancer, or lymphatic cancer. The cancer may be benign or metastatic.

More preferred cancers are brain tumors, in particular gliomas including glioblastoma multiforme (GBM).

Preferred infectious diseases for the uses and methods of the invention include diseases caused by viruses, bacteria, fungi, protozoa and multicellular parasites. They include, for instance, Amoebiasis, Anthrax, Buruli Ulcer (*Mycobacterium ulcerans*), Caliciviruses associated diarrhoea, *Campylobacter* diarrhoea, Cervical Cancer (Human papillomavirus), *Chlamydia trachomatis* associated genital diseases, Cholera, Crimean-Congo haemorrhagic fever, Dengue Fever, Diphtheria, Ebola haemorrhagic fever, Enterotoxigenic *Escherichia coli* (ETEC) diarrhoea, Gastric Cancer (*Helicobacter pylori*), Gonorrhea, Group A *Streptococcus* associated diseases, Group B *Streptococcus* associated diseases, *Haemophilus influenzae* B pneumonia and invasive disease, Hepatitis A, Hepatitis B, Hepatitis C, Hepatitis E diarrhoea, Herpes simplex type 2 genital ulcers, HIV/AIDS, Hookworm Disease, Influenza, Japanese encephalitis, Lassa Fever, Leishmaniasis, Leptospirosi, Liver cancer (Hepatitis B), Liver Cancer (Hepatitis C), Lyme Disease, Malaria, Marburg haemorrhagic fever, Measles, Mumps, Nasopharyngeal cancer (Epstein-Barr virus), *Neisseria meningitidis* Meningitis, Parainfluenza associated pneumonia, Pertussis, Plague, Poliomyelitis, Rabies, Respiratory syncytial virus (RSV) pneumonia, Rift Valley fever, Rotavirus diarrhoea, Rubella, Schistosomiasis, Severe Acute Respiratory Syndrome (SARS), Shigellosis, Smallpox, *Staphylococcus aureus* associated diseases, Stomach Cancer (*Helicobacter pylori*), *Streptococcus pneumoniae* and invasive disease, Tetanus, Tick-borne encephalitis, Trachoma, Tuberculosis, Tularaemia, Typhoid fever, West-Nile virus associated disease, Yellow fever.

In a preferred aspect of the use and method of the invention, the antigen presenting cells are dendritic cells, more preferably dendritic cells from the subject to be treated.

Typically, for cancer treatment, the therapeutically effective dose of a polypeptide according to the invention is from about 0.1 mg to 2 mg per injection.

Typically, for cancer treatment, the therapeutically effective dose of an antigen presenting cell loaded with a polypeptide according to the invention is from about 0.2 million cells to 2 million cells per injection.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Mode of Administration

Compounds, compositions, in particular vaccine compositions, and formulations thereof according to this invention may be administered in any manner including orally, parenterally, intravenously, rectally, or combinations thereof. Parenteral administration includes, but is not limited to, intravenous, intra-arterial, intra-peritoneal, subcutaneous, intradermal and intramuscular. The compositions of this invention may also be administered in the form of an implant, which allows slow release of the compositions as well as a slow controlled i.v. infusion.

Preferentially, the compounds, compositions, in particular vaccine compositions, and formulations thereof according to the invention are administered subcutaneously.

In one embodiment of the invention, the administration of the polypeptides, antigen presenting cells and compositions of the invention requires multiple successive injections. Thus, the administration can be repeated at least two times, once as primary immunization injections and, later, as booster injections.

In a preferred embodiment of the invention, the vaccine composition may be administered repeatedly or continuously. The vaccine composition can be administered repeatedly or continuously for a period of at least 1, 2, 3, or 4 weeks; 2, 3, 4, 5, 6, 8, 10, or 12 months; or 2, 3, 4, or 5 years.

Combination

According to a further embodiment, the administration of the pharmaceutical compositions in the methods and uses according to the invention can be carried out alone or in combination with a co-agent useful for treating and/or stabilizing the disease or disorder to be treated or repressed. In the case of treatment, prevention, or stabilization of a cancer, the administration of the pharmaceutical compositions in the methods and uses according to the invention can be carried out in combination with substances used in conventional chemotherapy directed against solid tumors and for control of establishment of metastases or any other molecule that act by triggering programmed cell death e.g. for example a co-agent selected from Tumor Necrosis Family Members including, but not limited, to Fas Ligand and tumor necrosis factor (TNF)-related apoptosis inducing (TRAIL) ligand. According to a further embodiment, the administration of the pharmaceutical compositions in the methods and uses according to the invention can be carried out in parallel of radiotherapy.

The invention encompasses the administration of a polypeptide of the invention, or an antigen-presenting cell of the invention, or a pharmaceutical composition thereof according to the invention, wherein it is administered to a subject prior to, simultaneously or sequentially with other therapeutic regimens or co-agents useful for treating, and/or stabilizing a cancer and/or preventing cancer relapsing (e.g. multiple drug regimens), in a therapeutically effective amount. A polypeptide of the invention, or an antigen-presenting cell of the invention, or a pharmaceutical composition thereof according to the invention that is administered simultaneously with said co-agents can be administered in the same or different composition(s) and by the same or different route(s) of administration.

Said other therapeutic regimens or co-agents may be selected from the group consisting of radiation therapy, chemotherapy, surgery, targeted therapy (including small molecules, peptides and monoclonal antibodies), and anti-angiogenic therapy. Anti-angiogenic therapy is defined herein as the administration of an agent that directly or indirectly targets tumor-associated vasculature.

According to one embodiment, is provided a pharmaceutical formulation comprising a polypeptide of the invention or an antigen-presenting cell of the invention, combined with at least one co-agent useful for treating and/or stabilizing a cancer and/or preventing a cancer relapsing, and at least one pharmaceutically acceptable carrier.

According to another embodiment of the invention, the compounds according to the invention and pharmaceutical formulations thereof can be administered after surgery where solid tumors have been removed as a prophylaxis against relapsing and/or metastases.

Patients

In an embodiment, patients according to the invention are patients suffering from a cancer.

In a particular embodiment, patients according to the invention have been subjected to a chirurgical removal of a tumor.

In another embodiment, patients according to the invention are patients suffering from an infectious disease.

References cited herein are hereby incorporated by reference in their entirety. The present invention is not to be limited in scope by the specific embodiments and drawings described herein, which are intended as single illustrations of individual aspects of the invention, and functionally equivalent methods and components are within the scope of the invention. The examples illustrating the invention are not intended to limit the scope of the invention in any way.

EXAMPLES

The following examples have been conducted to support the effectiveness of the ZEBRA-multiepitopic fusion proteins of the invention in the induction of a cytotoxic T cells and helper T cells dependent immune response.

Example 1

ZEBRA-Fusion Proteins Constructs

Figure 1:
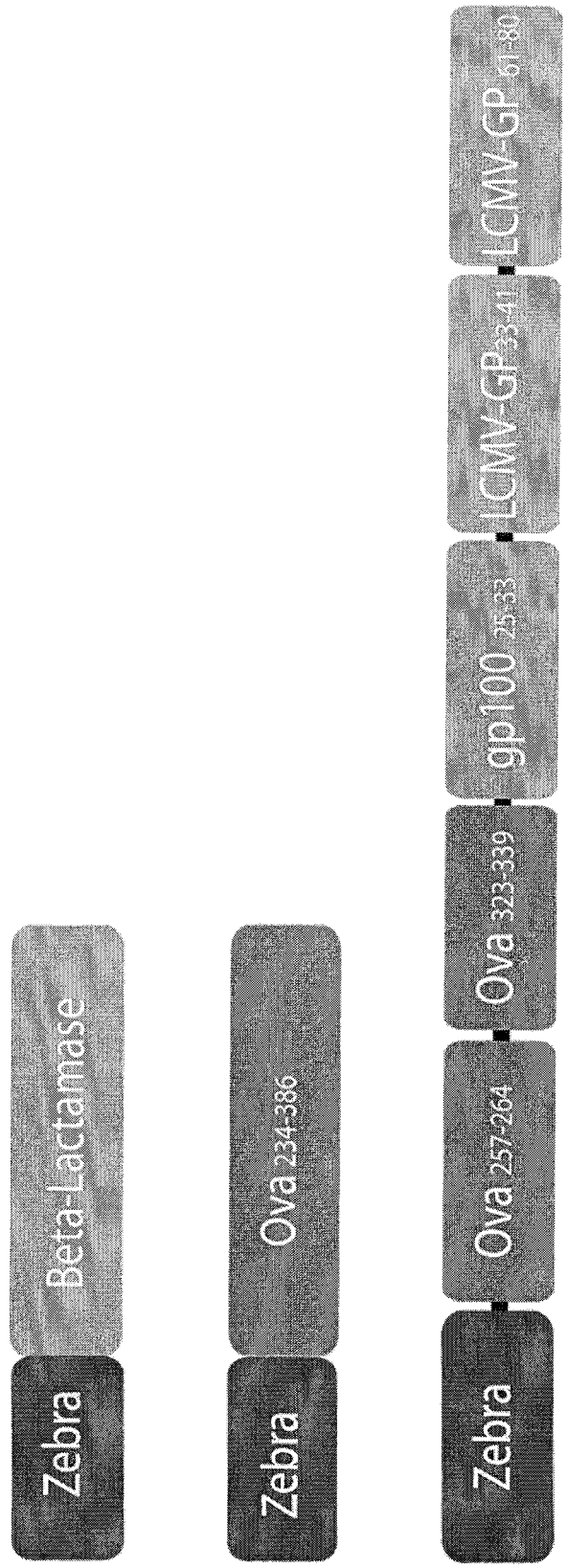
FIG. 1 shows different ZEBRA-fusion proteins used in the experimental section.

Three different constructs (FIG. 1) were engineered and cloned in a modified pET-15b vector deleted for thrombin and stop codons. N-terminal fusion proteins comprising amino acids residues 178-220 of ZEBRA (NCBI Accession Number YP_401673) were made carrying His-Tag allowing protein purification. The amino acid sequence of the ZEBRA fragment comprised in the ZEBRA fusion proteins described in the examples is SEQ ID NO: 8.

Construct 1: ZEBRA-β-lactamase: encodes β-lactamase from E. Coli deleted for the secretion signal (residues 1-23) and residue 24 His was changed to Asp to create an optimal Kozak sequence.

Construct 2: ZEBRA-OVA: encodes a truncated form of the chicken ovalbumin ($OVA_{234-386}$). This construction contains both CD8 epitope $OVA_{257-264}$ and CD4 epitope $OVA_{323-339}$.

Construct 3: ZEBRA-MultiE: encodes a chimeric protein with three CD8 epitopes from the ovalbumin $OVA_{257-264}$, from lymphocytic choriomengitis virus glycoprotein $LCMV-GP_{33-41}$ and from the murine tumor-associated antigen $GP100_{25-33}$ and two CD4 epitopes: $OVA_{323-339}$ and $LCMV-GP_{61-80}$. The spacers between each epitope are the natural flanking 4 amino acids residues.

Example 2

Protein Loading into DCs

A standard and reproducible protein delivery protocol for DCs was established using the quantifiable reporter protein β-lactamase and CCF2-AM its membrane-permeable substrate that allows monitoring of free cytoplasmic protein. Indeed, CCF2-AM is a lipophilic and esterified substrate, which can enter into the cells. Endogenous cytoplasmic esterase rapidly converts CCF2-AM into a negatively charged form (CCF2), which is not able to cross cell membranes, including endosomal membranes. Therefore, the β-lactamase transduced into cells with ZEBRA (construct 1) can cleave the CCF2 that is free in the cytoplasm.

A direct correlation between the protein concentration and time of incubation was observed. With increasing time and protein concentration, higher transduction efficiencies up to 70% were observed. For all the experiments described below a protein concentration of 0.3 µM and a loading time of 4 h were used, reaching transduction efficiencies of 70%. Under these experimental conditions, addition of β-lactamase without ZEBRA did not result in any detectable cleavage of CCF2. This indicated that the protein uptake was in majority mediated by ZEBRA rather than by the phagocytic capacity of dendritic cells.

Example 3

MHC Class I Restricted Presentation after ZEBRA-OVA Fusion Protein Loading into DCs Functional MHC I restricted presentation by DCs after loading with a truncated ovalbumin (OVA) protein (amino acids 234-386) fused to the PTDs (construct 2) was verified. Presentation of the immunodominant $CD8^+$ epitope from ovalbumin (SIINFEKL, $OVA_{257-264}$) was detected with the specific T cells from OT-1 T cell receptor (TCR) transgenic mice in vitro. TCR transgenic mice have all the $CD8^+$ or $CD4^+$ T cells specific for one epitope. The $CD8^+$ TCR transgenic mice used here are OT-1, specific for the $OVA_{257-264}$ epitope.

Bone marrow derived dendritic cells (BMDCs) were loaded with ZEBRA-$OVA_{257-264}$ during 4 h, washed and matured overnight with maturation cocktail containing IFNα, IFNγ, IL-4 and PolyIC (Fujita et al., 2009, Cancer Res. 69:1587-1595). OT-1 cells were stained with the non-toxic dye carboxyfluorescein succinimidyl ester (CFSE). Cell proliferation results in dilution of CFSE, which can be monitored by flow cytometry. CFSE stained OT-1 cells were incubated with matured BMDCs at a ratio 10:1 during 5 day. As positive control, mature BMDCs were pulsed with 10 µM Ova peptide. As negative control, OT-1 T cells were incubated without any stimulation. DCs loaded with ZEBRA-$OVA_{257-264}$ had the same priming capacity as peptide pulsed DCs with 81% and 93% proliferating CD8+ T cells, respectively. The same experiment was performed with BMDCs loaded with ZEBRA-$OVA_{257-264}$ after maturation. BMDCs loaded before or after maturation had the same priming capacity with 69% and 70% proliferating CD8+ respectively, confirming that cross-presentation results from ZEBRA-mediated antigen delivery.

Example 4

MHC Class II Restricted Presentation after ZEBRA-OVA Fusion Protein Loading into DCs The presentation of the OVA-specific CD4 epitope ($OVA_{323-339}$) was monitored with the OT-2 TCR transgenic mice. DCs loaded with ZEBRA-$OVA_{257-264}$ were able to activate OVA-specific $CD4^+$ T-cells.

Example 5

Multi-Epitopic $CD4^+$ and $CD8^+$ Presentation after ZEBRA-MultiE Fusion Protein Loading into DCs Similarly, a chimeric protein (called ZEBRA-MultiE fusion protein corresponding to construct 3) encoding OVA, the tumor-associated antigen gp100 and the viral LCMV-GP peptides was loaded into DCs and MHC I restricted presentation was monitored in vitro with lymphocytes from OT-1 mice, Pmel-1 mice transgenic for the gp100-specific TCR ($GP100_{25-33}$) and P14 mice transgenic for the LCMV-GP-specific TCR ($LCMV-GP_{33-41}$), respectively. MHC II restricted presentation was also monitored with lymphocytes from OT-2 mice and SMARTA mice transgenic for the LCMV-GP-specific TCR ($LCMV-GP_{61-80}$). Multi-epitopic presentation was observed with 3 $CD8^+$ epitopes (FIG. 2) and 2 CD4+ (FIG. 3) epitopes being efficiently presented. The presentation of gp100 was low, but significant. This may reflect the low affinity interaction of murine gp100 with the murine MHC class I molecule H-2D$^b$. The percentage of proliferating T cells after priming with DC loaded with ZEBRA-MultiE is similar to peptide pulsed DCs.

Example 6

Effector Function of T Cells Primed In Vitro by DCs Loaded with ZEBRA-MultiE Fusion Protein The proliferation of T cells described in the previous results indicates T cell activation through engagement of the T cell receptor (TCR) with the epitope-MHC complex. However, full differentiation to functional T cells includes expression of cytokines including IFNγ, TNFα and some IL-2. Moreover CD4 Th cells can polarize into Th1 (IFNγ+ IL-2+ TNFα+) promoting cell-mediated immune responses, or Th2 (IL-4+) promoting antibody mediated immune response. The goal here was to assess the cytokine profiles of CD8+ and CD4+ T cells activated in vitro. The supernatant was analyzed after 5 days of culture (FIG. 4). CD8+ T cells primed with BMDCs loaded with ZEBRA-MultiE were producing IFNγ and TNFα as the same level as the CD8+ T cells primed with peptide pulsed DCs (FIG. 4). No IL-2 was found in the culture supernatant of CD8+ T cells cultivated with ZEBRA-MultiE loaded BMDCs. CD4+ T cells showed a Th1 polarization with secretion of IFNγ and TNFα, and again no IL-2 was found.

To clarify whether the absence of IL-2 in the supernatants reflected consumption by the CD8+ and CD4+ T cells primed with ZEBRA-MultiE loaded BMDCs, intracellular cytokine staining after 4 days of culture was performed. 45% of OT-1 CD8+ T cells were positive for IL-2 expression, and 21% of the P14 CD8+ T cells. Similarly, around 60% of the SMARTA and OT-2 CD4+ T cells were positive for IL-2 expression. It is most likely, that the produced IL-2 is not accumulating in the culture medium but rapidly used by the proliferating T cells. Therefore, in vitro primed T cells by ZEBRA-MultiE loaded BMDCs are able to proliferate as well as producing effector cytokines, including Th1 cytokines that will support cell mediated immunity.

The potential of ZEBRA to deliver antigens in vivo was then evaluated by either vaccinating with ZEBRA-MultiE transduced DC, or directly with the ZEBRA-MultiE fusion protein.

Example 7

Vaccination of Mice with DCs Loaded with ZEBRA-MultiE Fusion Protein

For DC vaccination, mice were vaccinated twice with a 14-days interval with type 1 polarized (Fujita et al., 2009, Cancer Res. 69:1587-1595) BMDC (10$^6$ mature DCs per vaccination) loaded with ZEBRA-MultiE. Seven days after the second vaccination, cells were isolated from lymph node and spleen, restimulated with the peptides contained in MultiE, and intracellular cytokine expression was measured in both CD4 and CD8 T cell populations (FIG. 5). The proportion of CD8+ (top panel) or CD4+ (bottom panel) T cells expressing each cytokine after in vitro restimulation with each peptide epitope is plotted in the bar chart. The multifunctionality of the response (capacity to express 1, 2, or 3 cytokines) is illustrated in the pie chart. Some multifunctionality ($\geq 2$ cytokines) is present for every epitope tested, although the proportions of multifunctional T cells vary according to the epitope.

Example 8

Vaccination of Mice with ZEBRA-MultiE Fusion Protein

Mice were vaccinated subcutaneously twice with a 14-days interval with 6 µg ZEBRA-MultiE and 100 µg PolyIC. Seven days after the second vaccination, cells were isolated from lymph node and spleen, restimulated with the peptides contained in ZEBRA-MultiE, and intracellular cytokine expression was measured in both CD4 and CD8 T cell populations (FIG. 6). The proportion of CD8+ (top panel) or CD4+ (bottom panel) T cells expressing each cytokine after in vitro restimulation with each peptide epitope is plotted in the bar chart. The multifunctionality of the response (capacity to express 1, 2, or 3 cytokines) is illustrated in the pie chart. Interestingly, the proportion of cells showing multifunctionality was higher than with the DC based vaccine, including the number of IL-2 expressing cells. Moreover, since the tested epitopes contained in ZEBRA-MultiE are presented by 3 different H-2 molecules, positive T cell responses to these epitopes validates that a T cell immune response restricted by multiple MHC molecules has been induced. The MHC restriction elements for each epitope are: $OVA_{257-264}$: H-2Kb; $OVA_{323-339}$: H-2-I-Ab; $LCMV-GP_{33-41}$: H-2 Db; $gp100_{25-33}$: H-2Db; $LCMV-GP_{61-80}$: H-2-IAb).

Example 9

ZEBRA-MultiE can be Processed and Presented by Dendritic Cells with Different MHC Molecules Bone marrow derived dendritic cells from mice on BALB/c background were loaded for 4 h with 0.3 µM Zebra-MultiE and matured overnight with poly ICLC (Hiltonol®). Zebra-MultiE loaded and matured dendritic cells were co-incubated with CFSE stained splenocytes from DO11.10 TCR transgenic mice in which all of the CD4+ T cells are specific for the immunodominant ovalbumin epitope $OVA_{257-264}$. As negative control, splenocytes were incubated with non-loaded dendritic cells. For the positive control, the dendritic cells were pulsed with peptide. After five days of culture, T cell proliferation by CFSE dilution was monitored by flow cytometry.

Results of FIG. 7 show that Zebra-MultiE can be processed and presented by dendritic cells with different MHC molecules.

Example 10

ZEBRA-MultiE Translocates into Endogenous Dendritic Cells In Vivo and is Processed, Leading to Cross-Presentation on MHC Class I Molecules C57BL/6 mice were vaccinated with PBS for the negative control, 200 µg peptides and 100 µg anti-CD40 subcutaneously and 50 μg Poly ICLC (Hiltonol®) intramuscularly for the positive control or 10 μg ZEBRA-MultiE protein and 100 μg anti-CD40 subcutaneously and 50 μg Poly ICLC (Hiltonol®) intramuscularly. The same day, 1.5×10⁶ CFSE stained splenocytes from either P14 or OT1 TCR transgenic mice were adoptively transferred by intravenous injection. Four days after vaccination/adoptive transfer, the mice were sacrificed and proliferation of adoptively transferred T cell from draining lymph nodes was assessed by CFSE dilution.

Results of FIG. 8 show that Zebra-MultiE translocates into endogenous dendritic cells in vivo and is processed, leading to cross-presentation on MHC class I molecules.

Example 11

Vaccination of Mouse with ZEBRA-MultiE can Induce Polyclonal Immune Responses

C57BL/6 mice were vaccinated twice at 14-days of interval by subcutaneous injection of 10 μg ZEBRA-MultiE protein and 100 μg anti-CD40 and intramuscular injection of 50 μg Poly ICLC (Hiltonol®). Seven days after the boost, the mice were sacrificed and the percentages of CD8⁺ T cells specific for either OVA$_{323-339}$, LCMV-GP$_{33-41}$, or GP100$_{25-33}$ were assessed in the draining lymph nodes by tetramer staining.

The results of FIG. 9 show that vaccination of mouse with ZEBRA-MultiE can induce polyclonal immune responses.

We claim:

1. An isolated polypeptide comprising:
   (i) at least one CD4+ epitope(s);
   (ii) at least one CD8+ epitope(s), wherein said CD4+ and CD8+ epitopes are selected from the group consisting of epitopes from a tumor-associated antigen, epitopes from a tumor-specific antigen, and epitopes from an antigenic protein from a pathogen; and
   (iii) a protein transduction domain consisting of SEQ ID NO: 8 or a protein transduction domain consisting of amino acids 1 to 43 of SEQ ID NO: 8.

2. The isolated polypeptide according to claim 1, wherein the polypeptide comprises a protein transduction domain consisting of SEQ ID NO: 8, at least one CD4+ epitope(s), and at least one CD8+ epitope(s), wherein said CD4+ and CD8+ epitopes are selected from the group consisting of epitopes from a tumor-associated antigen, epitopes from a tumor-specific antigen, and epitopes from an antigenic protein from a pathogen.

3. The isolated polypeptide according to claim 1, wherein said polypeptide contains at least two CD4+ epitopes and at least two CD8+ epitopes and:
   (i) said at least two CD4+ epitopes are restricted to at least two MHC class II molecules; and
   (ii) said at least two CD8+ epitopes are restricted to at least two MHC class I molecules of the human population.

4. Isolated antigen-presenting cells loaded with the polypeptide according to claim 1.

5. The isolated antigen presenting cells according to claim 4, which are selected from the group consisting of dendritic cells, macrophages and B-cells.

6. A method for preparing antigen presenting cells comprising transducing antigen presenting cells with the polypeptide of claim 1, cultivating said cells in a culture medium and separating said cells from the culture medium.

7. A pharmaceutical composition comprising the polypeptide of claim 1 and a pharmaceutically acceptable carrier.

8. A method of preparing a pharmaceutical composition comprising the step of mixing the polypeptide of claim 1 and a pharmaceutically acceptable carrier.

9. The isolated polypeptide according to claim 1, wherein said $CD4^+$ epitope consists of about 8-25 amino acids and said $CD8^+$ epitope consists of about 8-15 amino acids.

10. The isolated polypeptide according to claim 1, wherein said $CD4^+$ epitope consists of about 12 to about 25 amino acids and said $CD8^+$ epitope consists of about 8 to about 11 amino acids.

11. The isolated polypeptide according to claim 1, wherein the polypeptide comprises a protein transduction domain consisting of amino acids 1 to 43 of SEQ ID NO: 8, at least one $CD4^+$ epitope(s), and at least one $CD8^+$ epitope(s), wherein said $CD4^+$ and $CD8^+$ epitopes are selected from the group consisting of epitopes from a tumor-associated antigen, epitopes from a tumor-specific antigen, and epitopes from an antigenic protein from a pathogen.

12. The isolated polypeptide according to claim 1, wherein the polypeptide consists of (i) at least one $CD4^+$ epitope(s), (ii) at least one $CD8^+$ epitope(s), wherein said $CD4^+$ and $CD8^+$ epitopes are selected from the group consisting of epitopes from a tumor-associated antigen, epitopes from a tumor-specific antigen, and epitopes from an antigenic protein from a pathogen; and (iii) a protein transduction domain consisting of the amino acid sequence SEQ ID NO: 8, or amino acids 1 to 43 of SEQ ID NO: 8.

13. The isolated polypeptide according to claim 12, wherein the polypeptide consists of (i) at least one $CD4^+$ epitope(s), (ii) at least one $CD8^+$ epitope(s), wherein said $CD4^+$ and $CD8^+$ epitopes are selected from the group consisting of epitopes from a tumor-associated antigen, epitopes from a tumor-specific antigen, and epitopes from an antigenic protein from a pathogen; and (iii) a protein transduction domain consisting of amino acids 1 to 43 of SEQ ID NO: 8.

14. The isolated polypeptide according to claim 12, wherein the polypeptide consists of (i) at least one $CD4^+$ epitope(s), (ii) at least one $CD8^+$ epitope(s), wherein said $CD4^+$ and $CD8^+$ epitopes are selected from the group consisting of epitopes from a tumor-associated antigen, epitopes from a tumor-specific antigen, and epitopes from an antigenic protein from a pathogen; and a protein transduction domain consisting of the amino acid sequence SEQ ID NO: 8.

* * * * *